United States Patent
Ichimura et al.

(10) Patent No.: US 6,337,167 B1
(45) Date of Patent: Jan. 8, 2002

(54) BIS(AMINOSTYRYL)BENZENE COMPOUNDS AND SYNTHETIC INTERMEDIATES THEREOF, AND PROCESS FOR PREPARING THE COMPOUNDS AND INTERMEDIATES

(75) Inventors: Mari Ichimura; Shinichiro Tamura; Tadashi Ishibashi; Ichinori Takada, all of Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/455,724

(22) Filed: Dec. 6, 1999

(30) Foreign Application Priority Data

Dec. 7, 1998 (JP) ............................ 10-347561
Nov. 2, 1999 (JP) ............................ 11-312069

(51) Int. Cl.$^7$ ............................ C07C 211/54
(52) U.S. Cl. ............. 430/73; 430/74; 558/419; 558/22; 564/434
(58) Field of Search ............. 558/419, 422; 564/434; 430/73, 74

(56) References Cited

U.S. PATENT DOCUMENTS 4,175,961 A * 11/1979 Wright et al. ............... 430/58
6,022,998 A * 2/2000 Kawaguchi et al. ........ 564/434

* cited by examiner

Primary Examiner—Mukund J. Shah
Assistant Examiner—Thomas McKenzie
(74) Attorney, Agent, or Firm—Sonnenschein, Nath & Rosenthal

(57) ABSTRACT

To provide compounds, which are suitable for use as an organic luminescent material capable of developing intense luminescence which is yellow to red, and a process for preparing in general and high efficiency. A bis(aminostyryl) benzene compound of the following general formula [I] is provided General formula [I]:

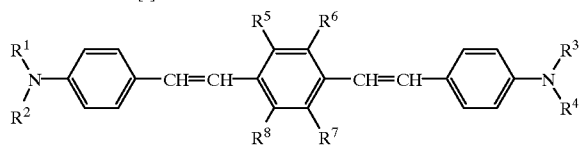

wherein $R^2$ and $R^3$ independently represent an unsubstituted aryl group, and $R^1$ and $R^4$ independently represent an aryl group, and $R^5$ to $R^8$, independently represent a cyano group or the like. A process for the preparation thereof is described wherein a 4-(N,N-diarylamino)benzaldehyde and a diphosphonic acid ester or diphosphonium are subjected to condensation reaction. Intermediates of the bis(aminostyryl) benzene compound are also described.

4 Claims, 25 Drawing Sheets

STRUCTURAL FORMULA (36)-2

STRUCTURAL FORMULA (36)-1

FIG. 12 STRUCTURAL FORMULA (27)-7

F I G. 14
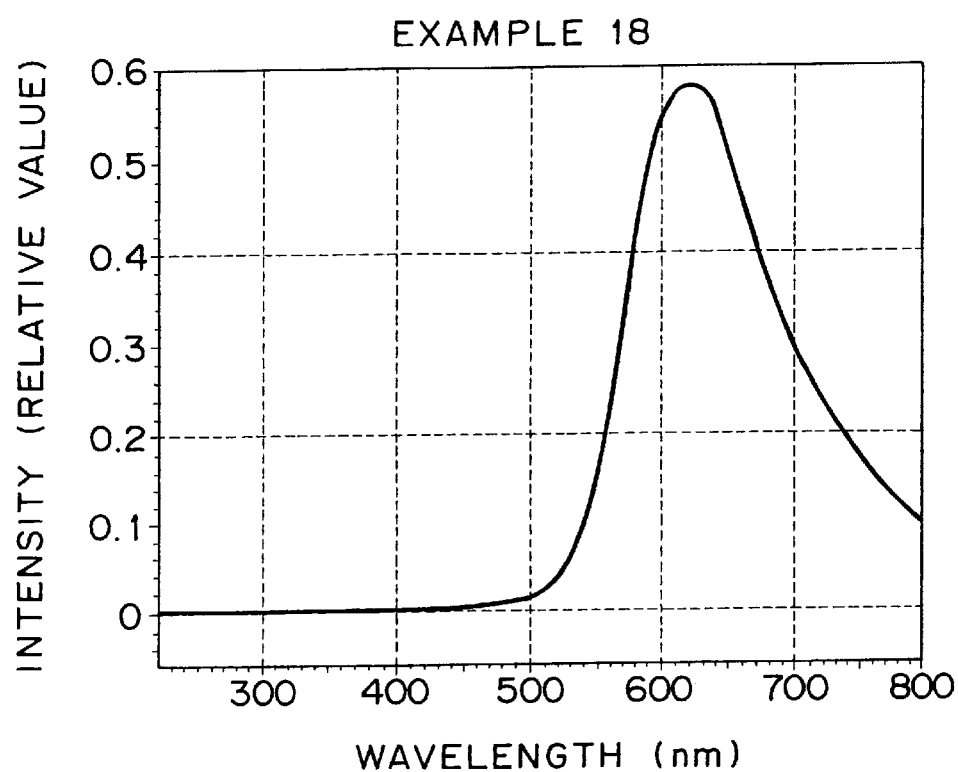
F I G. 15
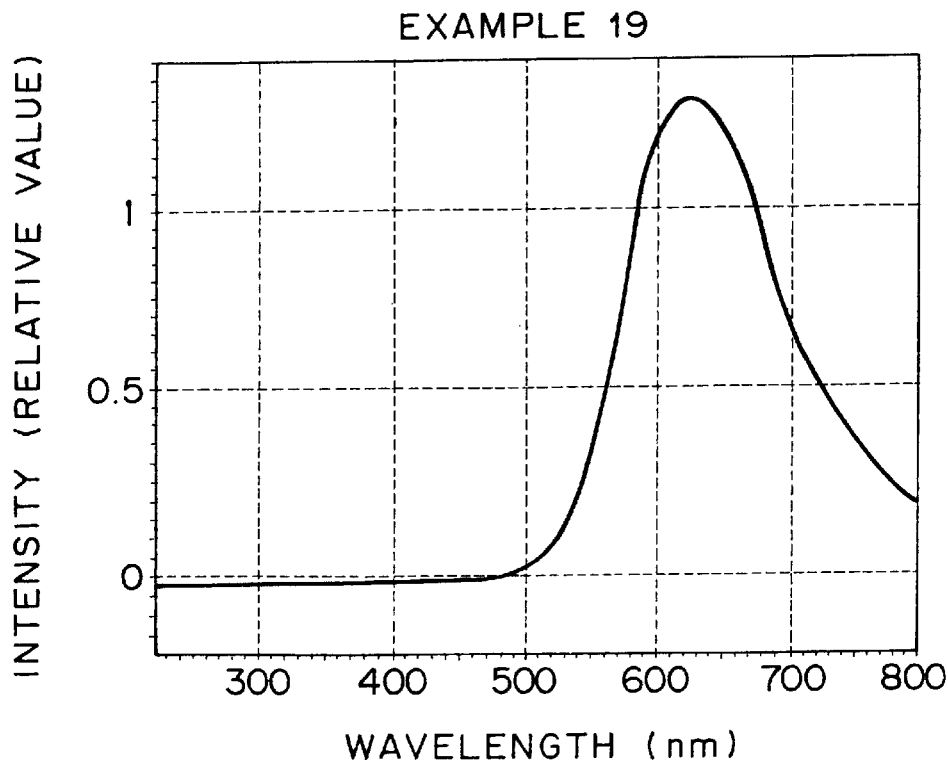

F I G. 20
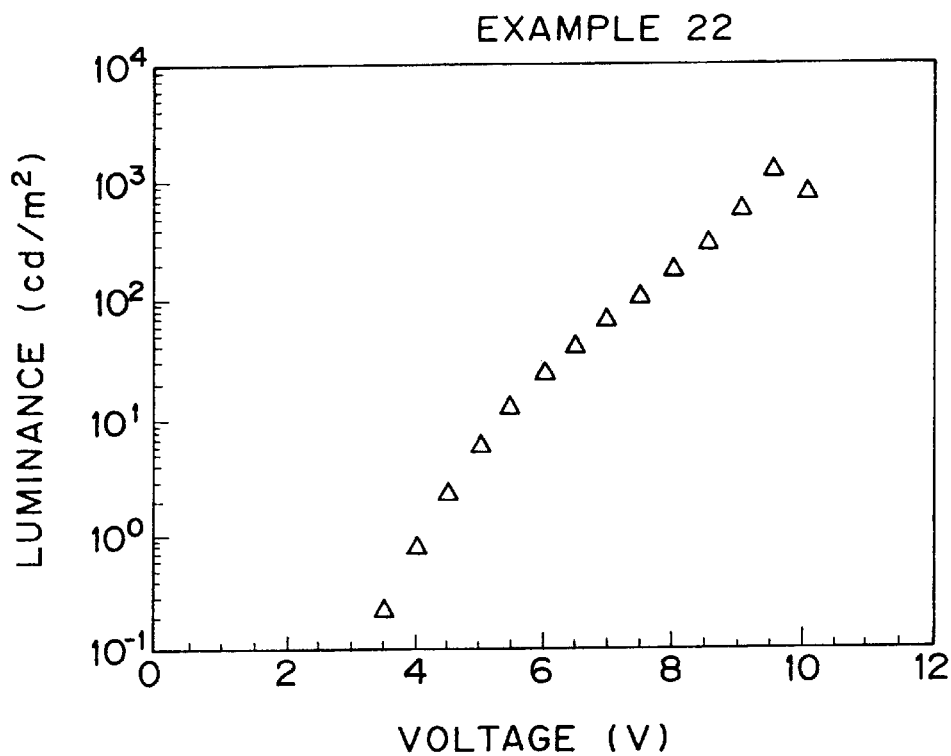
F I G. 21
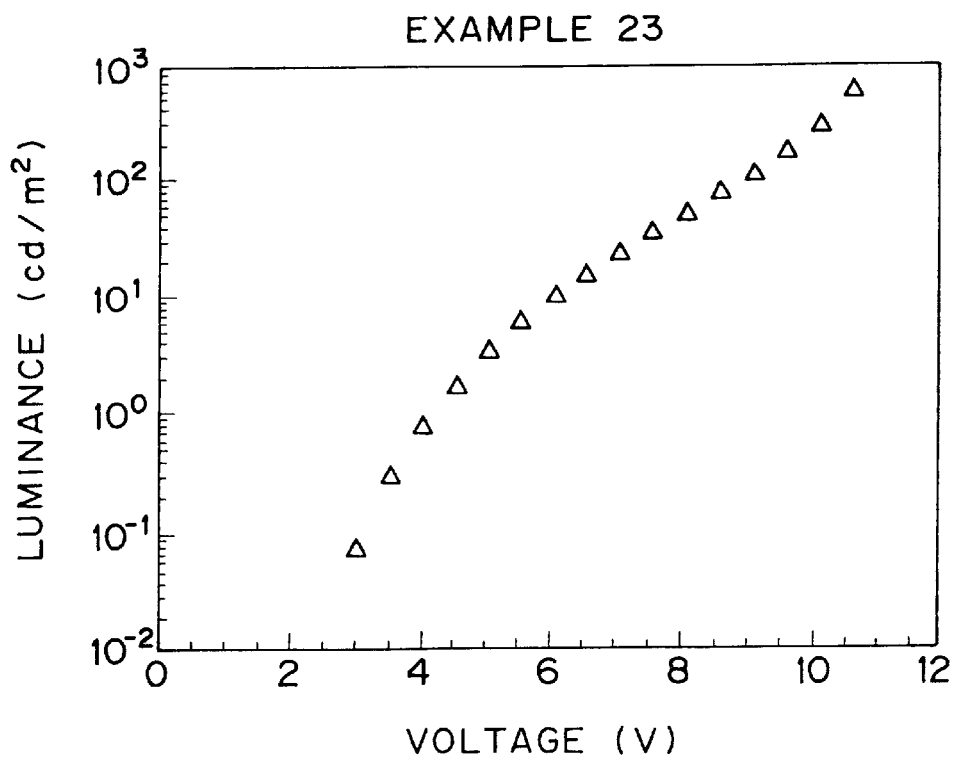

F I G. 30
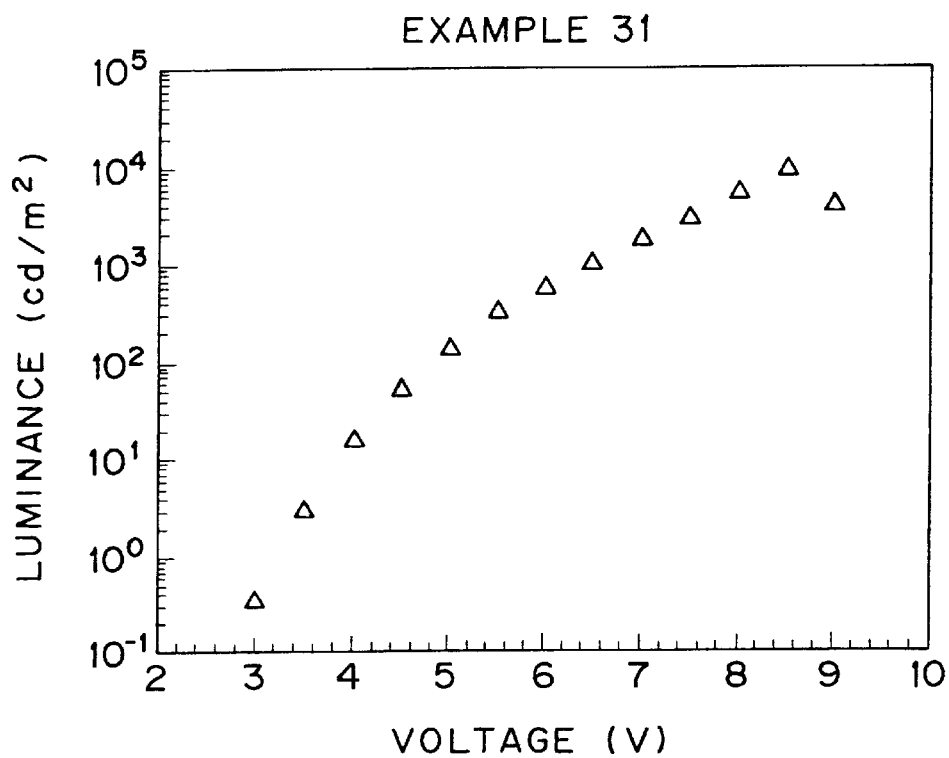
F I G. 31
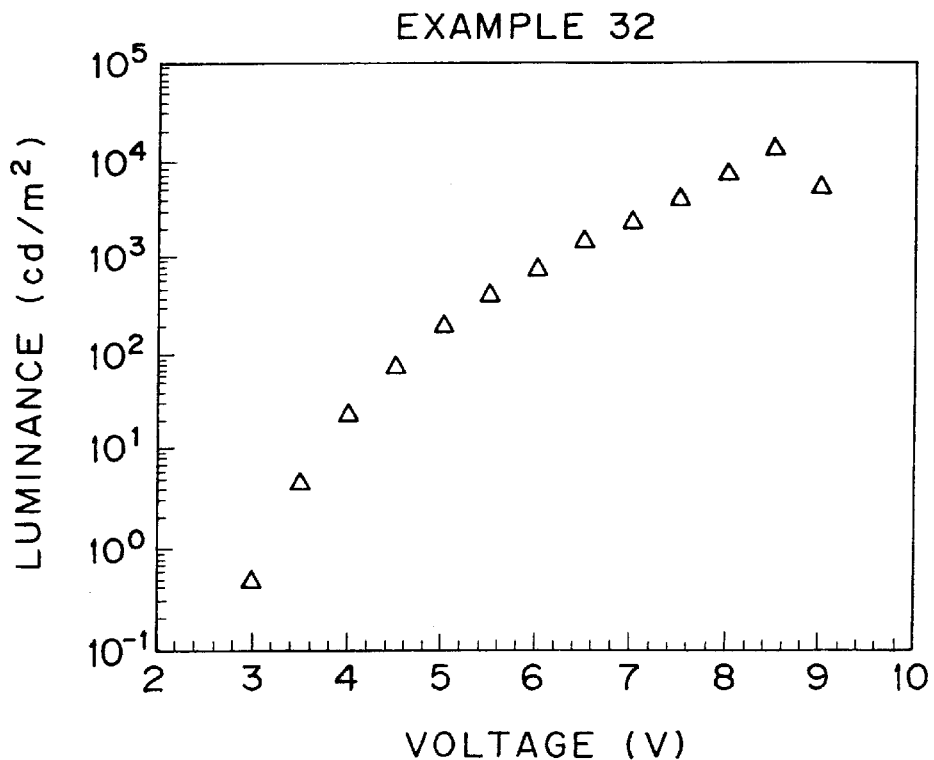

BIS(AMINOSTYRYL)BENZENE COMPOUNDS AND SYNTHETIC INTERMEDIATES THEREOF, AND PROCESS FOR PREPARING THE COMPOUNDS AND INTERMEDIATES

BACKGROUND OF THE INVENTION

1. Field of the Invention

This invention relates to bis(aminostyryl)benzene compounds which are suitable for use as an organic luminescent material capable of developing a desired luminescent color and to synthetic intermediates thereof. The invention also relates to a process for preparing such compounds and intermediates as mentioned above.

2. Description of the Related Art

As a candidate for flat panel displays which make use of spontaneous light, have a high response speed and has no dependence on an angle of field, attention has been recently paid to organic electroluminescent device (EL device) and an increasing interest has been taken in organic luminescent materials for the EL device. The first advantage of the organic luminescent material resides in that the optical properties of the material can be controlled, to an extent, depending on the molecular design, so that it is possible to realize a full color organic luminescent device wherein three primary color luminescences of red, blue and green can be all ensured by use of the respective organic luminescent materials.

The bis(aminostyryl)benzene compound of the following general formula [A] is able to develop blue to red strong luminescence in a visible region depending on the type of introduced substituent:

General formula [A]:

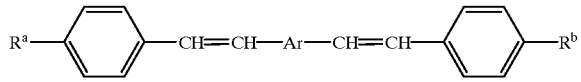

wherein Ar represents an aryl group which may have a substituent, $R^a$ and $R^b$, respectively, represent a hydrogen atom, a saturated or unsaturated hydrocarbon group, an aryl group which may have a substituent, a cyano group, a halogen atom, a nitro group or an alkoxy group and may be the same or different. Hence, this compound is utilizable not only as a material for an organic electroluminescent device, but also in various fields. These materials are sublimable in nature, with the attendant advantage that they can be formed as a uniform amorphous film according to a process such as vacuum deposition. Nowadays, although optical properties of a material can be predicted to some extent by calculation of its molecular orbital, it is as a matter of course that a technique of preparing a required material in a high efficiency is most important from the industrial standpoint.

Up to now, a great number of compounds including those of the above general formula [A] have been prepared for use as an organic luminescent material. The fluorescence or luminescence of these materials mostly covers blue to green colors, and only a few of materials which develop yellow to red luminescence has been reported [Technical Investigation Report of The Association of Electric Information Communication, Organic Electronics, 17, 7 (1992), Inorganic and Organic Electroluminescence 96 Berlin, 1010 (1996) and the like]. In addition, there has never been established any highly efficient process of preparing such materials.

SUMMARY OF THE INVENTION

Accordingly, an object of the invention is to provide compounds, which are suitable for use as an organic luminescent material capable of developing intense luminescence which is particularly yellow to red in color, and synthetic intermediates thereof.

Another object of the invention is to provide a process for preparing the compounds and their intermediates in a high efficiency.

We made intensive studies in order to solve the above-stated problems of the prior art, and as a result, found that bis(aminostyryl)benzene compounds of the general formulas [I], [II], [III] and [IV] are able to develop intense luminescence and are suitable as a luminescent material of yellow to red colors. At the same time, we established general and highly efficient preparation thereof.

More particularly, there is provided, according to the invention, a bis(aminostyryl)benzene compound of the following general formula [I], [II], [III] or [IV] (which may be hereinafter referred to as inventive compound):

General formula [I]:

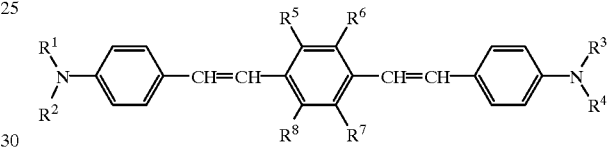

wherein $R^2$ and $R^3$ independently represent an unsubstituted aryl group, and $R^1$ and $R^4$ independently represent an aryl group represented by the following general formula (1):

General formula (1):

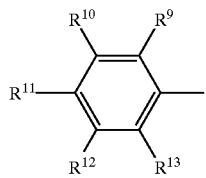

in which $R^9$, $R^{10}$, $R^{11}$, $R^{12}$ and $R^{13}$ are independently groups, which may be the same or different, provided that at least one of them is a saturated or unsaturated hydrocarbon oxy group or a hydrocarbon group having two or more carbon atoms, and $R^5$, $R^6$, $R^7$ and $R^8$ independently groups, which may be the same or different, provided that at least one of them represents a hydrogen atom, a cyano group, a nitro group or a halogen atom (which means F, Cl, Br or I herein and hereinafter):

General formula [II]:

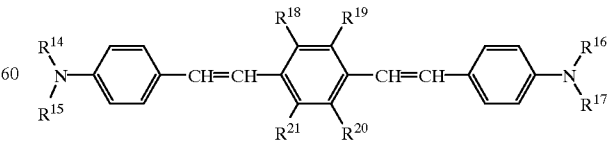

wherein $R^{14}$, $R^{15}$, $R^{16}$ and $R^{17}$ may be the same or different and independently represent an aryl group of the following general formula (2):

General formula (2):

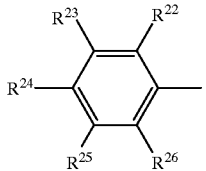

in which $R^{22}$, $R^{23}$, $R^{24}$, $R^{25}$ and $R^{26}$ are independently groups, which may be the same or different, provided that at least one of them represents a saturated or unsaturated hydrogren oxy group or a hydrocarbon group, and $R^{18}$, $R^{19}$, $R^{20}$ and $R^{21}$ are independently groups, which may be the same or different, provided that at least one of them represents a hydrogen atom, a cyano group, a nitro group or a halogen atom:

General formula [III]:

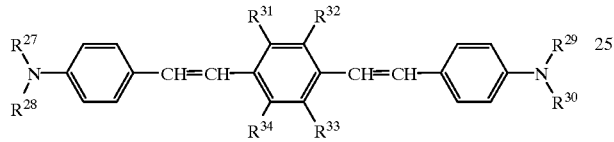

wherein at least one of $R^{27}$, $R^{28}$, $R^{29}$ and $R^{30}$ represents an aryl group of the following general formula (3) and the others represent an unsubstituted aryl group:

General formula (3):

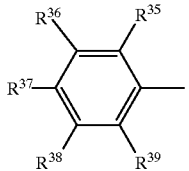

in which $R^{35}$, $R^{36}$, $R^{37}$, $R^{38}$ and $R^{39}$ are independently groups, which may be the same or different, provided that at least one of them is a saturated or unsaturated hydrocarbon amino group, and $R^{31}$, $R^{32}$, $R^{33}$ and $R^{34}$ are independently groups, which may be the same or different, provided that at least one of them is a hydrogen atom, a cyano group, a nitro group or a halogen atom:

General formula [IV]:

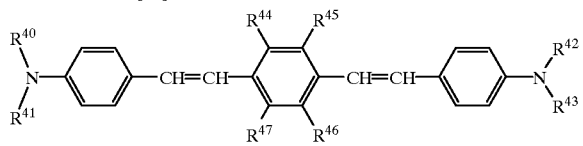

wherein $R^{41}$ and $R^{42}$ may be the same or different and independently represent an aryl group of the following general formula (4):

General formula (4):

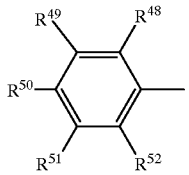

in which $R^{48}$, $R^{49}$, $R^{50}$, $R^{51}$ and $R^{52}$ may be the same or different and independently represent a hydrogen atom, or at least one thereof is a saturated or unsaturated hydrocarbon oxy group or a hydrocarbon group, and $R^{40}$ and $R^{43}$ may be the same or different and independently represent an aryl group of the following general formula (5):

General formula (5):

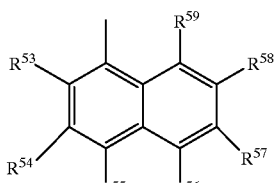

in which $R^{53}$, $R^{54}$, $R^{55}$, $R^{56}$, $R^{57}$, $R^{58}$ and $R^{59}$ may be the same or different and independently represent a hydrogen atom or at least one thereof represents a saturated or unsaturated hydrocarbon oxy group or a hydrocarbon group, and $R^{44}$, $R^{45}$, $R^{46}$ and $R^{47}$ are independently groups, which may be the same or different, provided that at least one of them is a hydrogen atom, a cyano group, a nitro group or a halogen atom.

The inventive compounds can be effectively utilized as an organic luminescent material capable of developing yellow to red luminescence. These compounds are ones which have a high glass transition point and a high melting point and are excellent in electric, thermal and chemical stabilities. In addition, they are amorphous in nature, is capable of readily forming a vitreous state and may be subjected to vacuum deposition.

BRIEF DESCRIPTION OF THE DRAWINGS

FIG. 14 is an emission spectrogram of an organic electroluminescent device of Example 18 of the invention;

FIG. 15 is an emission spectrogram of an organic electroluminescent device of Example 19 of the invention;

FIG. 20 is a graph showing a voltage-luminance characteristic of the organic electroluminescent device of Example 22 of the invention;

FIG. 21 is a graph showing a voltage-luminance characteristic of the organic electroluminescent device of Example 23 of the invention;

FIG. 30 is a graph showing a voltage-luminance characteristic of the organic electroluminescent device of Example 31 of the invention;

FIG. 31 is a graph showing a voltage-luminance characteristic of the organic electroluminescent device of Example 32 of the invention;

DETAILED DESCRIPTION OF PREFERRED EMBODIMENTS

Figure 1:
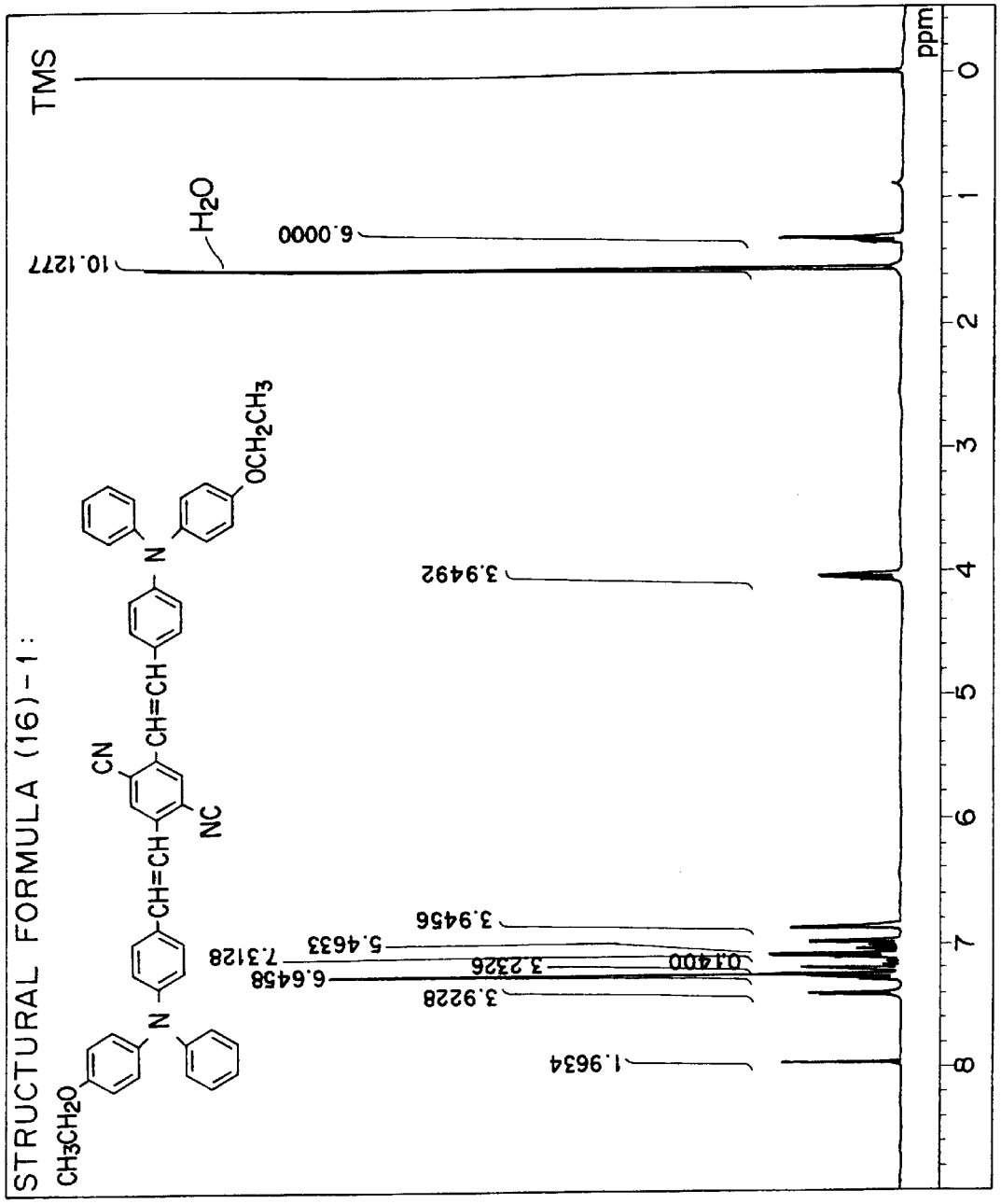
FIG. 1 is an $^1$HNMR spectral diagram of a bis (aminostyryl)benzene compound of structural formula (16)-1 of the invention.

Preferred compounds of the invention are those of the following general formula:

General formula :

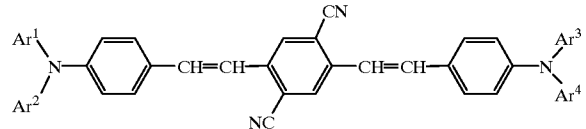

wherein $Ar^1$, $Ar^2$, $Ar^3$ and $Ar^4$ may be the same or different and independently represent an aryl group which may have a substituent, and if a substituent is present, such an aryl group is one selected from those aryl groups of the following general formulas (6), (7), (8) and (9):

General formula (6):

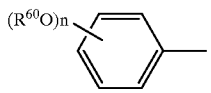

General formula (7):

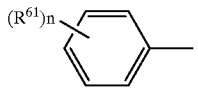

General formula (8):

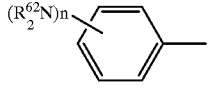

General formula (9):

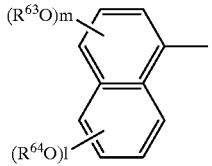

wherein $R^{60}$ represents a saturated or unsaturated hydrocarbon group having 2 or more carbon atoms, preferably from 2 to 4 carbon atoms, provided that where $Ar^1$, $Ar^2$, $Ar^3$ and $Ar^4$ are all the aryl group of the general formula (6), $R^{60}$ represents a saturated or unsaturated hydrocarbon group having 1 or more carbon atoms, $R^{61}$ and $R^{62}$ independently represent a saturated or unsaturated hydrocarbon group having 1 or more carbon atoms, preferably 1 to 4 carbon atoms, $R^{63}$ and $R^{64}$ may be the same or different and independently represent a saturated or unsaturated hydrocarbon group having 1 or more carbon atoms, preferably 1 to 4 carbon atoms, n is an integer of 0 to 5, m is an integer of 0 to 3, and 1 is an integer of 0 to 4.

Preferred compounds of the invention are those represented by the following general formulas, (10), (11), (12), (13), (14) and (15):

General formula (10):

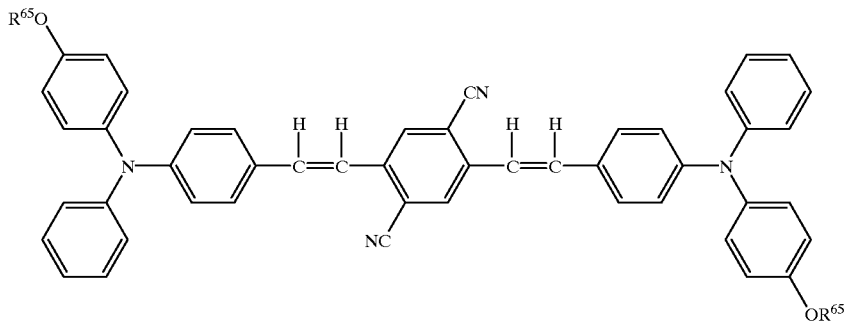

wherein $R^{65}$ represents a saturated or unsaturated hydrocarbon group having from 2 to 4 carbon atoms:

General formula (11):

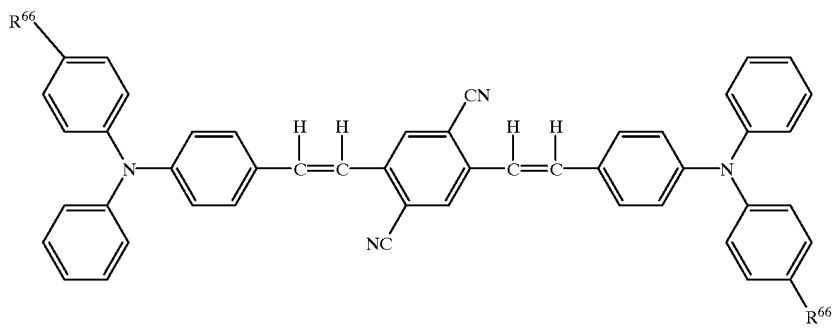

wherein $R^{66}$ represents a saturated or unsaturated hydrocarbon group having from 1 to 4 carbon atoms:

General formula (12):

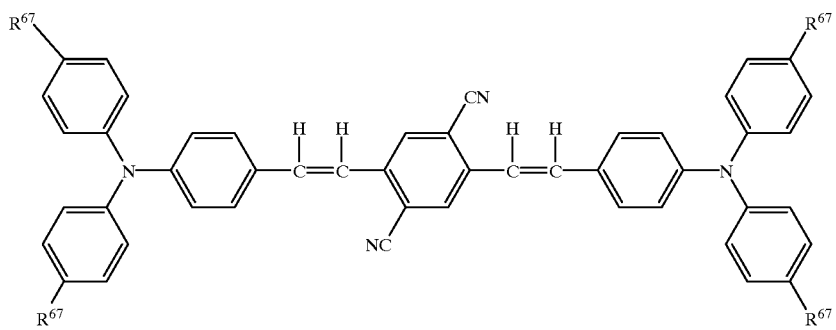

wherein $R^{67}$ represents a saturated or unsaturated hydrocarbon group having from 1 to 4 carbon atoms:

General formula (13):

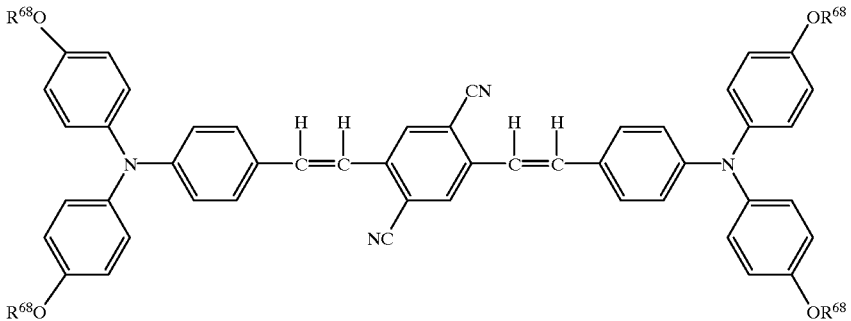

wherein $R^{68}$ represents a saturated or unsaturated hydrocarbon group having from 1 to 4 carbon atoms:

General formula (14):

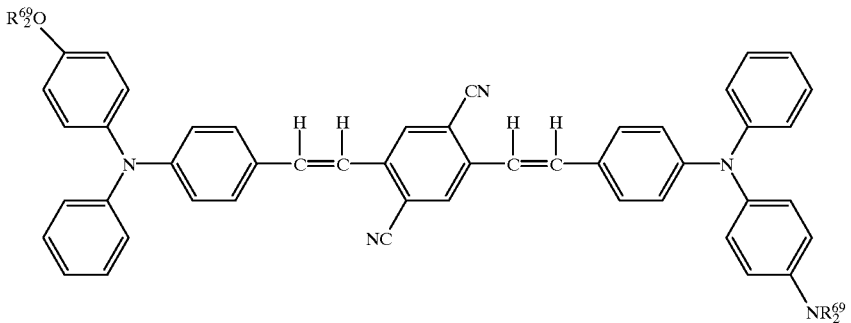

wherein $R^{69}$ represents a saturated or unsaturated hydrocarbon group having from 1 to 4 carbon atoms:

General formula (15):

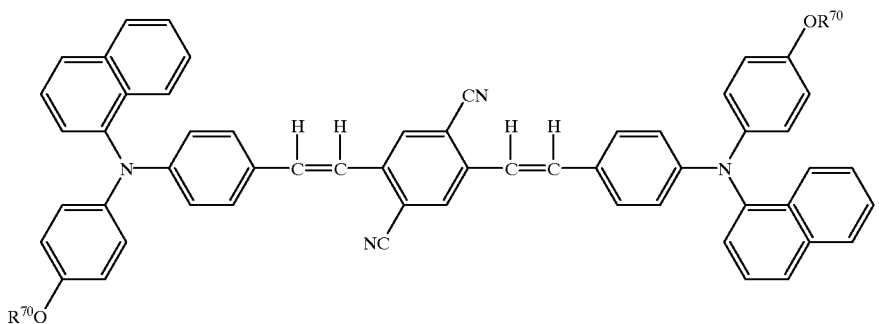

wherein $R^{70}$ represents a saturated or unsaturated hydrocarbon group having from 1 to 4 carbon atoms.

More specific examples of the compounds of the invention include those of the following structural formulas (16)-1, (16)-2, (16)-3, (16)-4, (16)-5, (16)-6 and (16)-7:

Structural formula (16)-1:
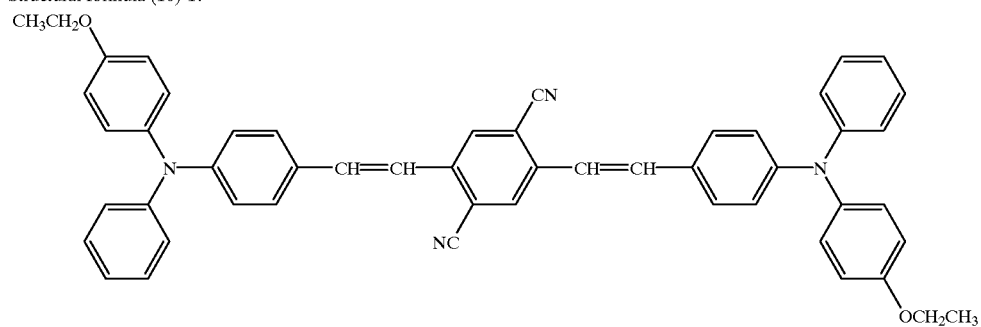
Structural formula (16)-2:
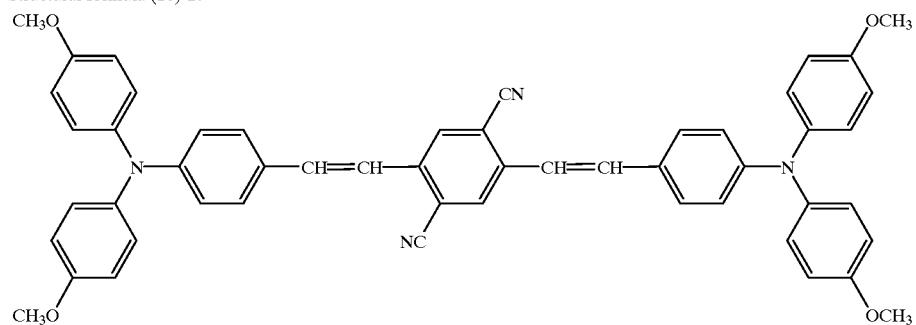
Structural formula (16)-3:
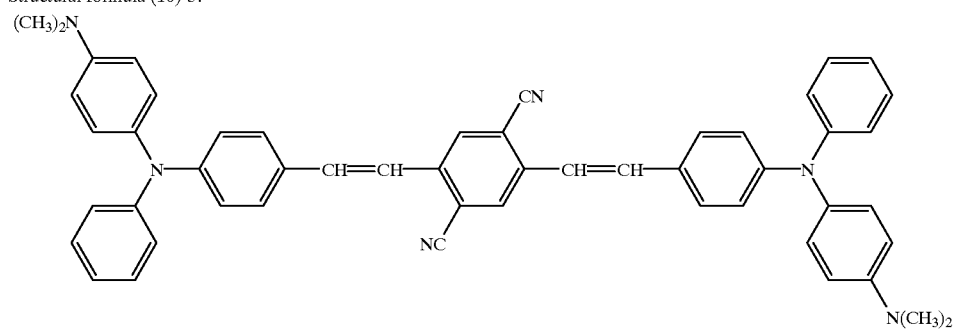
Structural formula (16)-4:
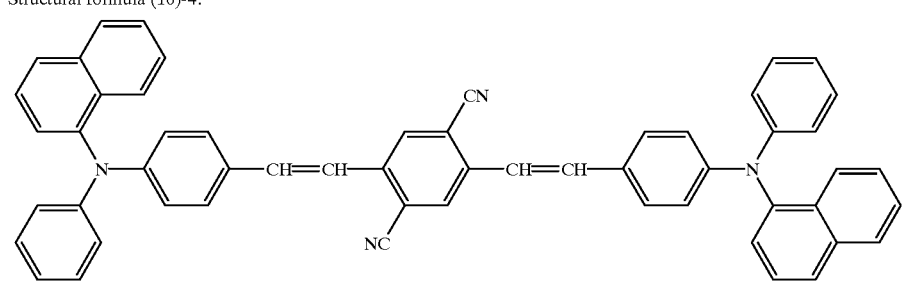
Structural formula (16)-5:
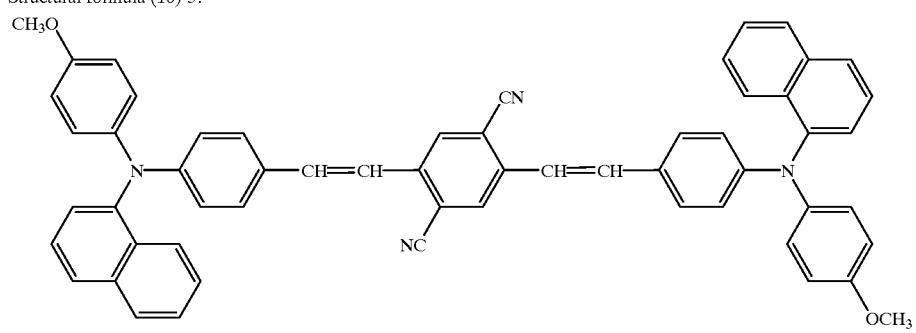

Structural formula (16)-6:
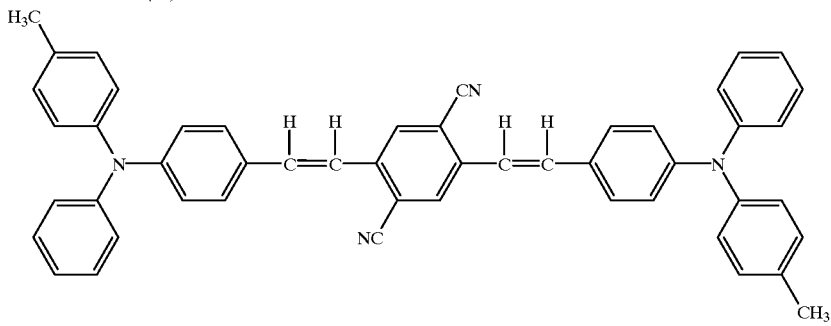
Structural formula (16)-7:
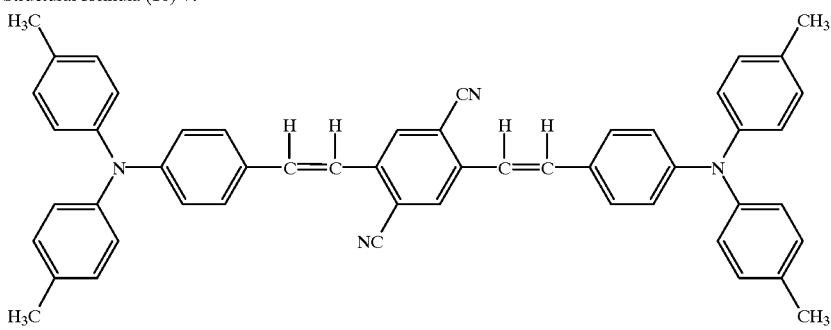
Besides, mention is made of the following compounds:
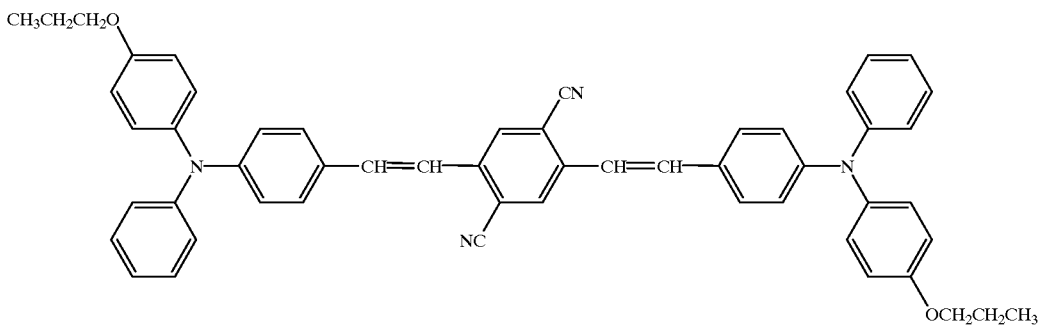
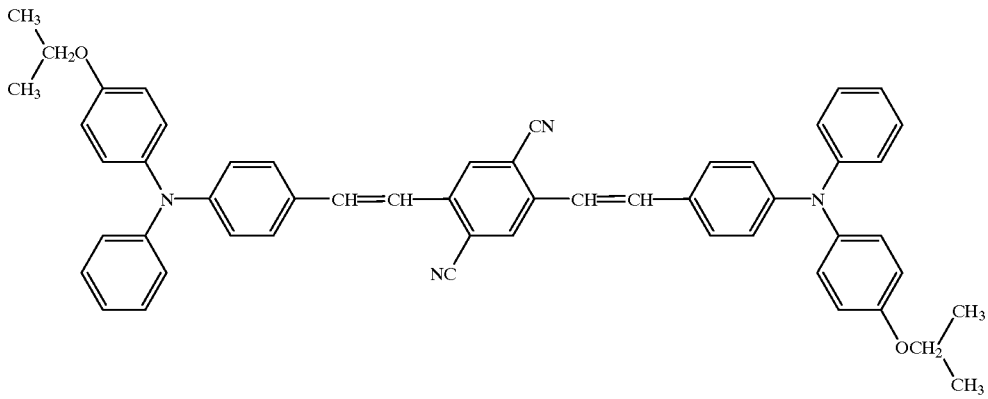

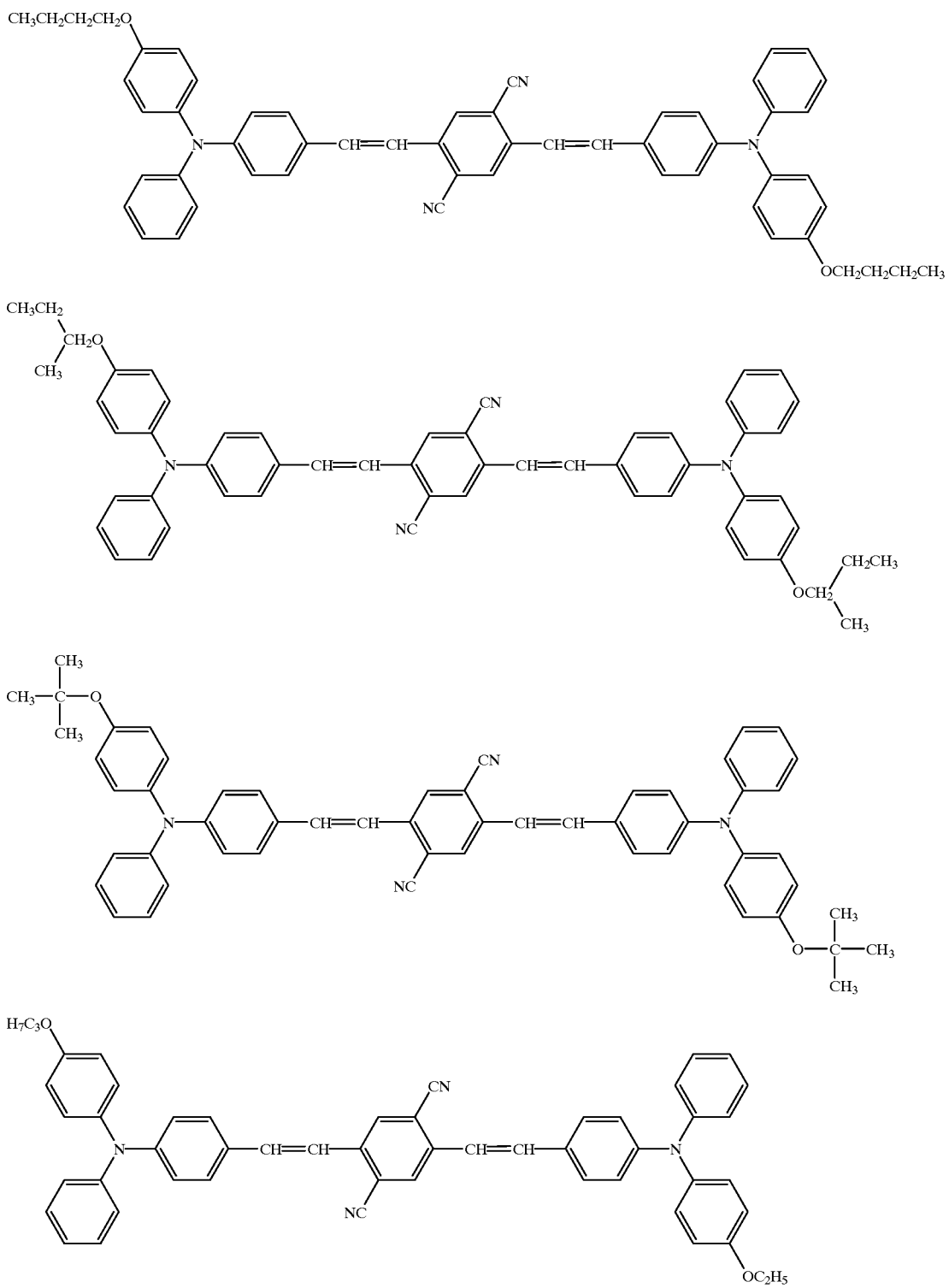

-continued
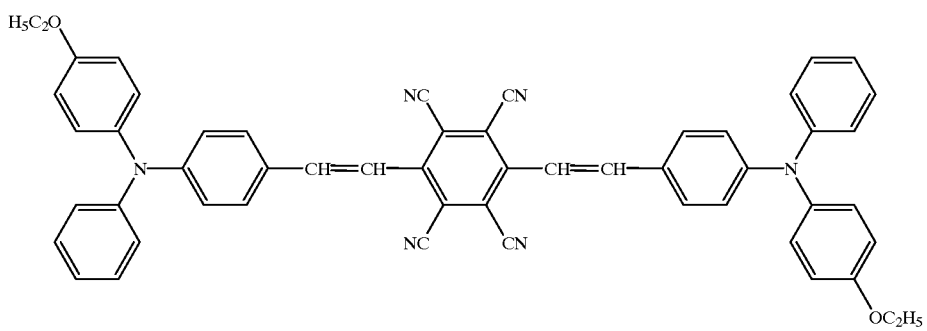
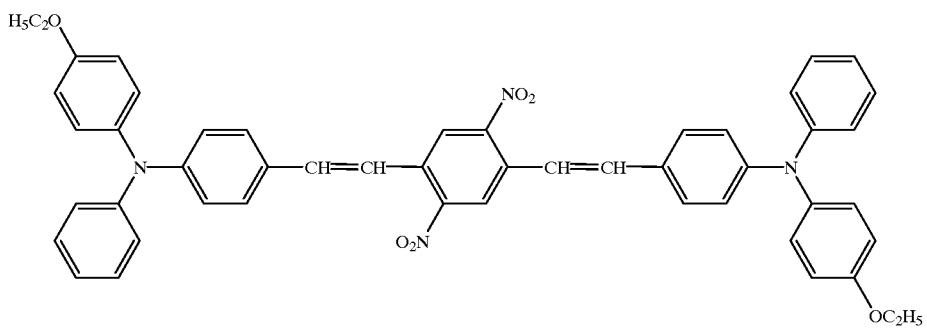
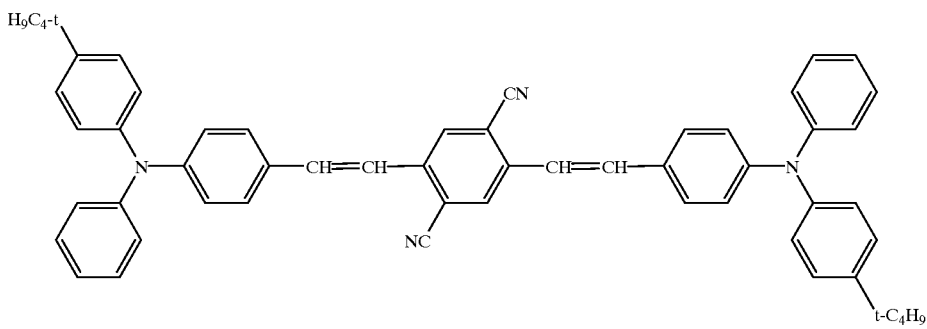
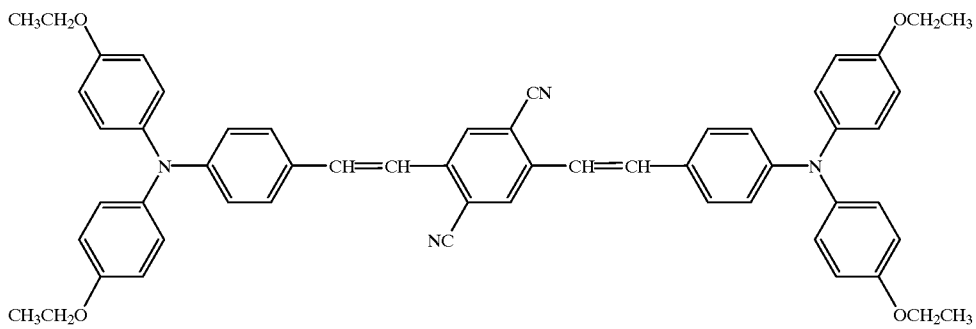
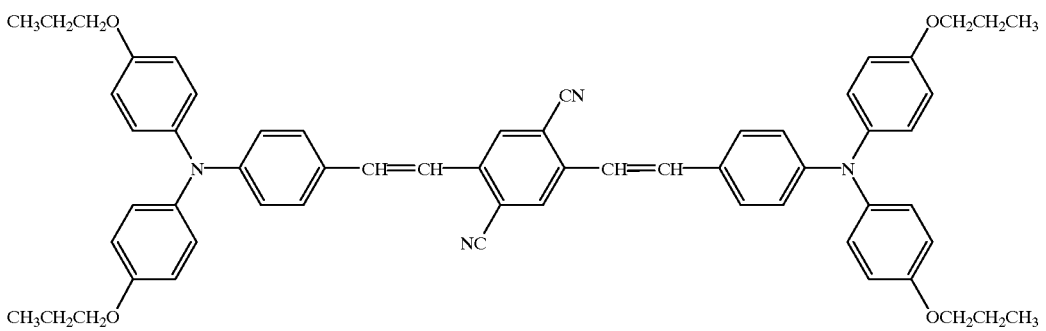

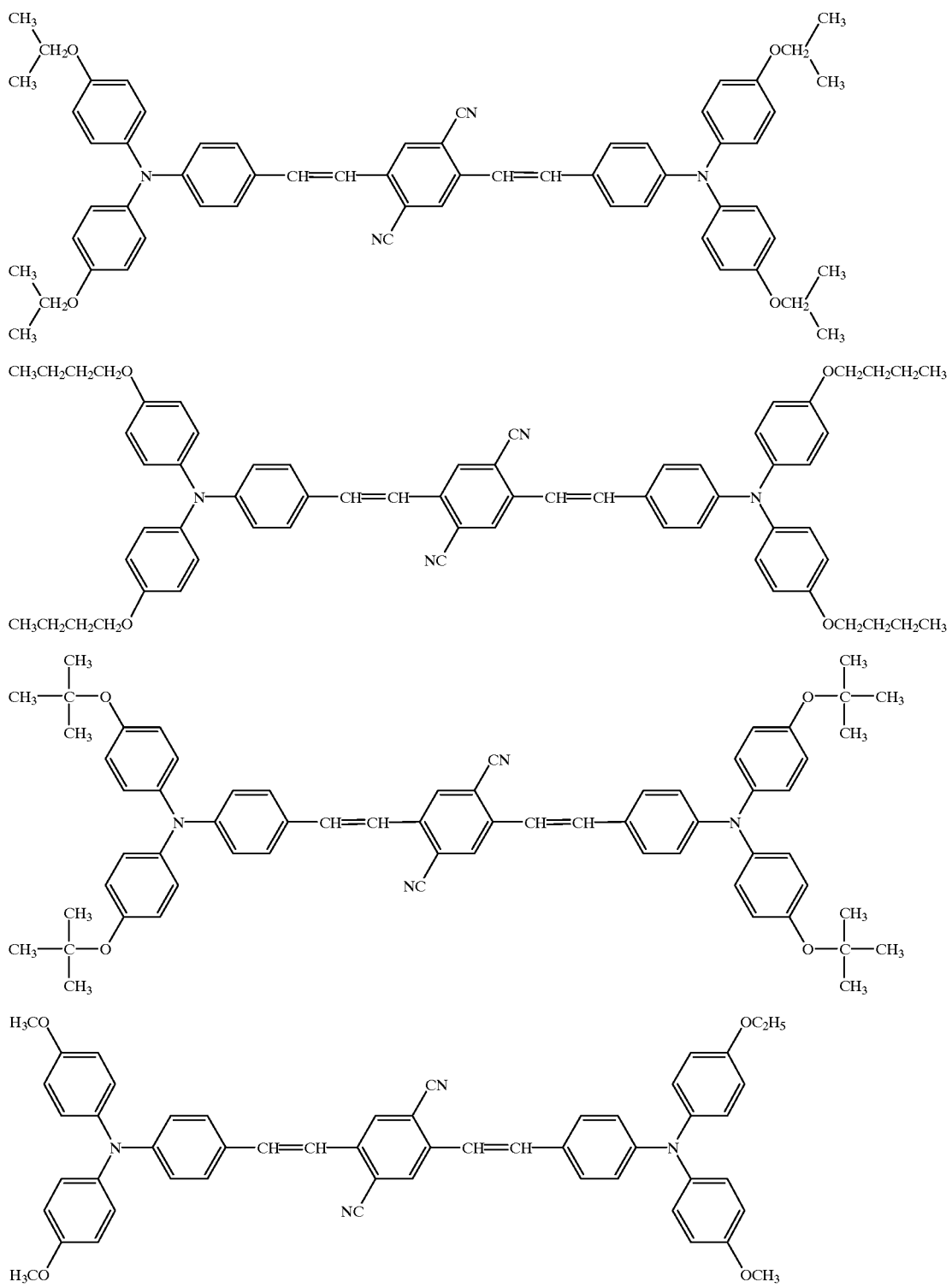

-continued
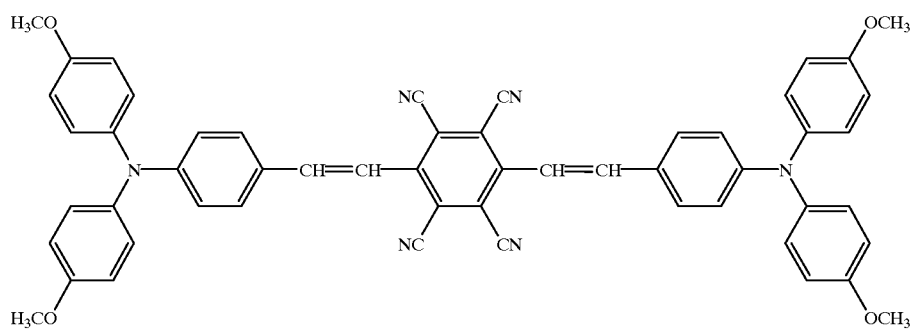
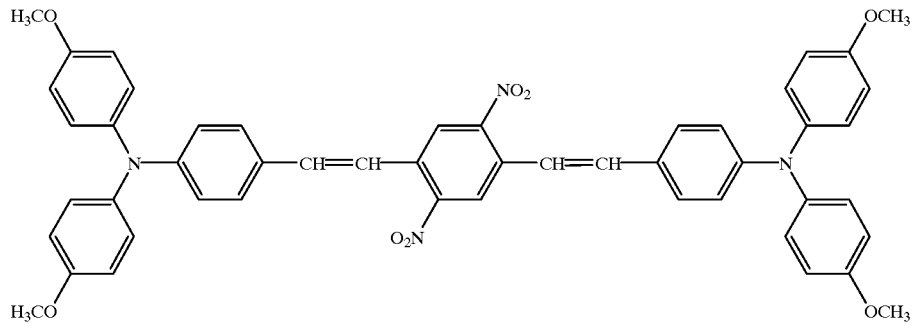
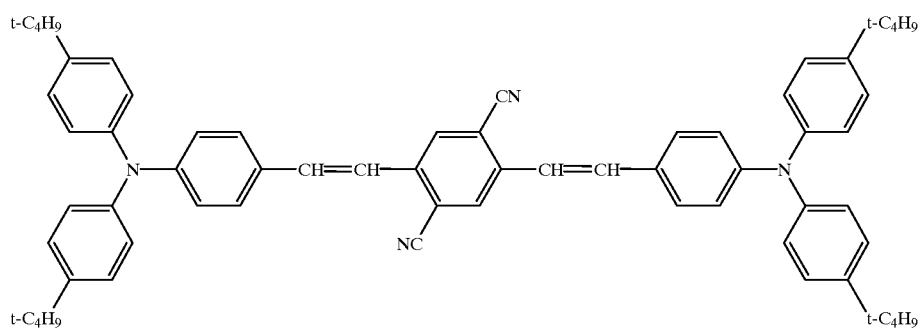
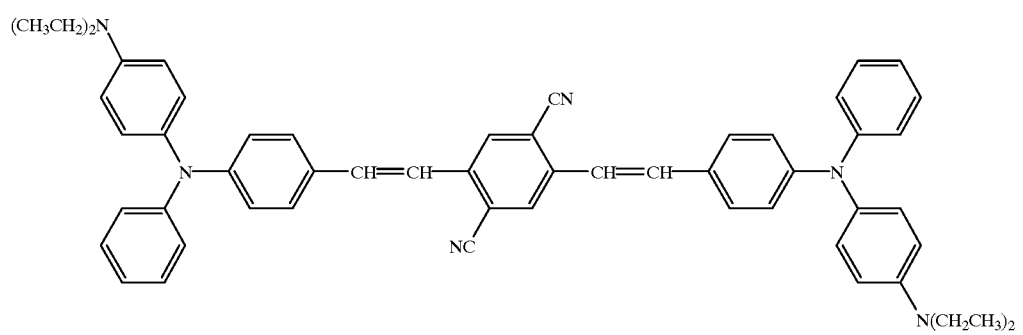
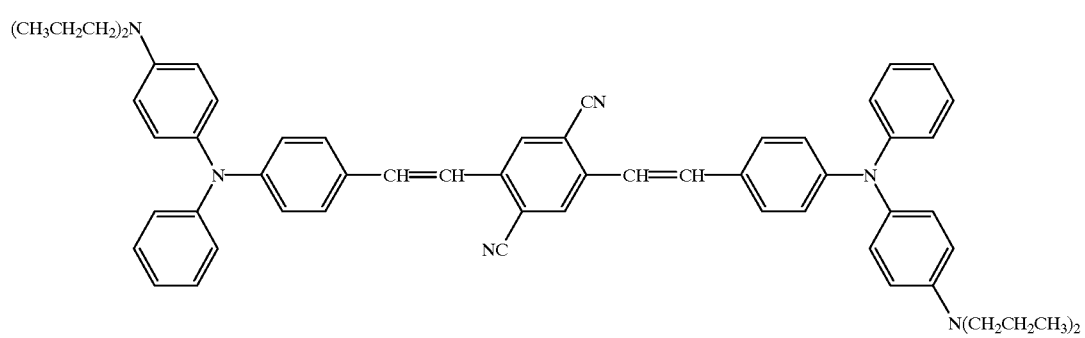

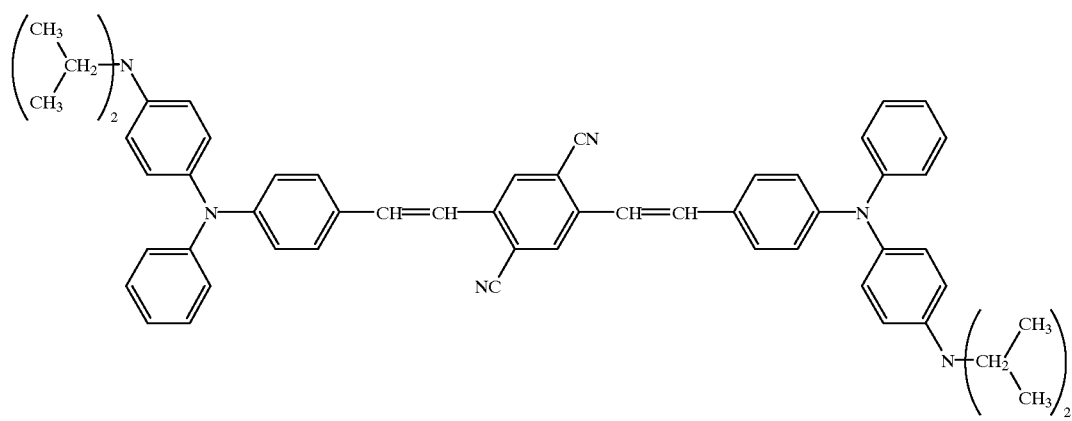
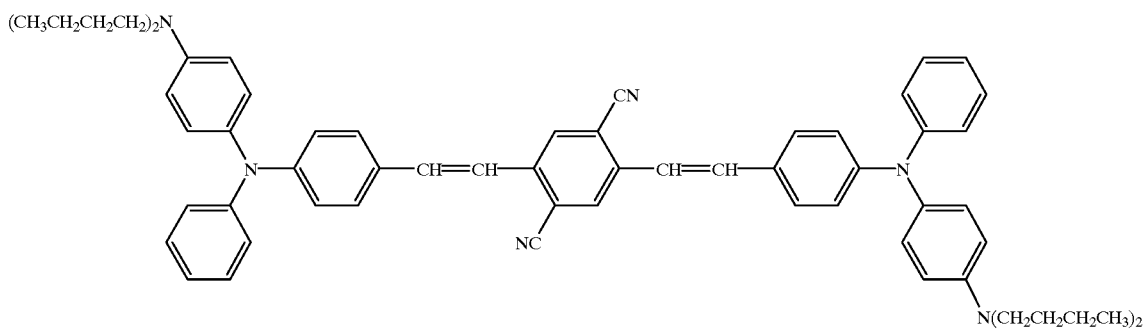
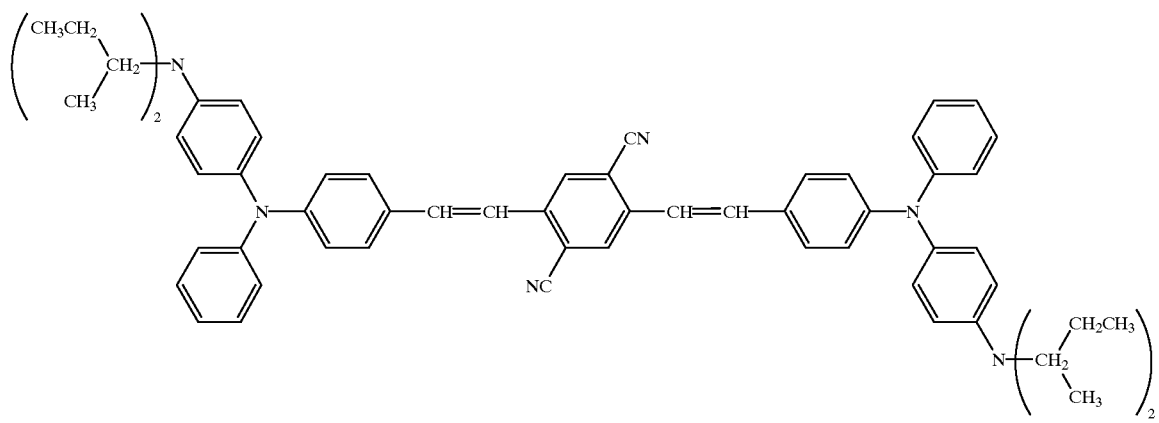
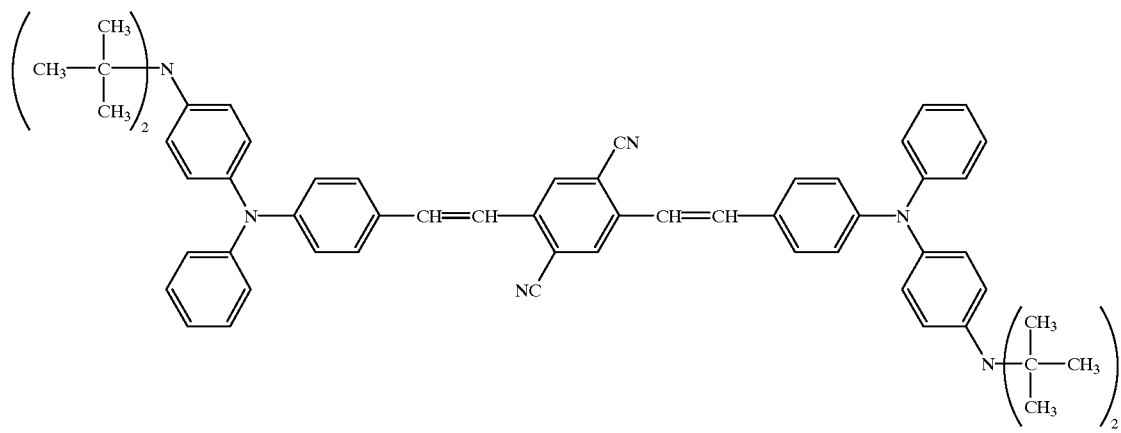

-continued
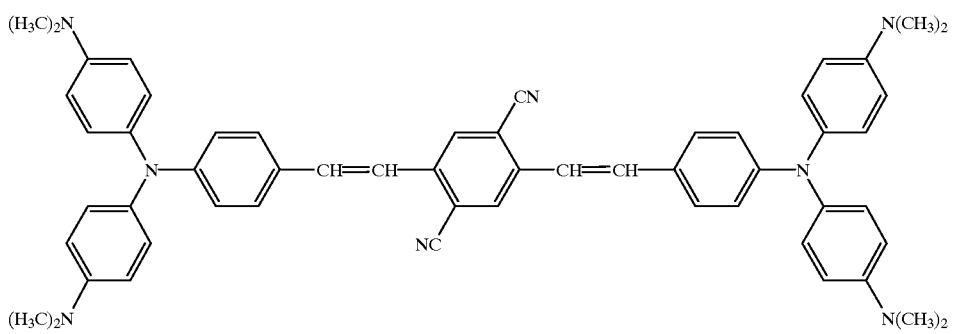
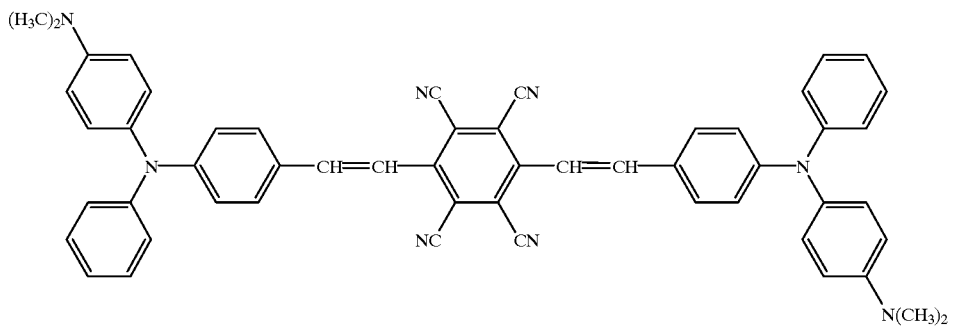
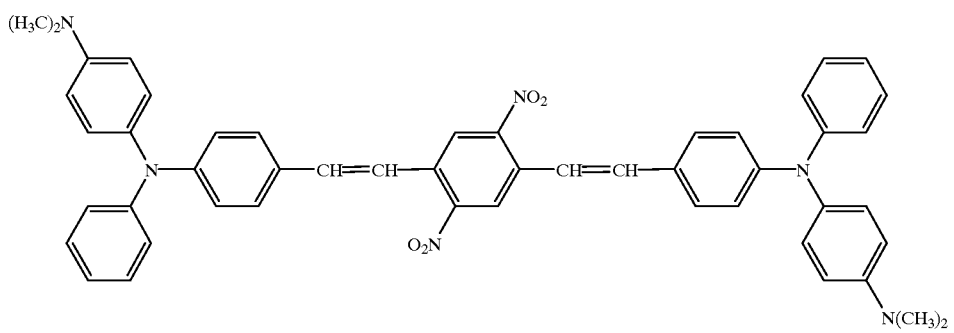
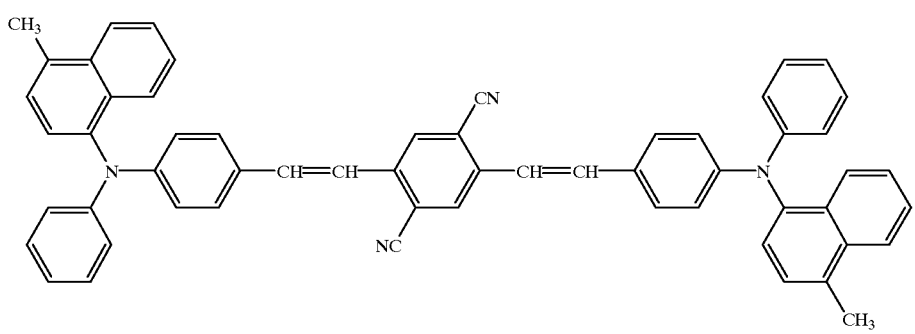
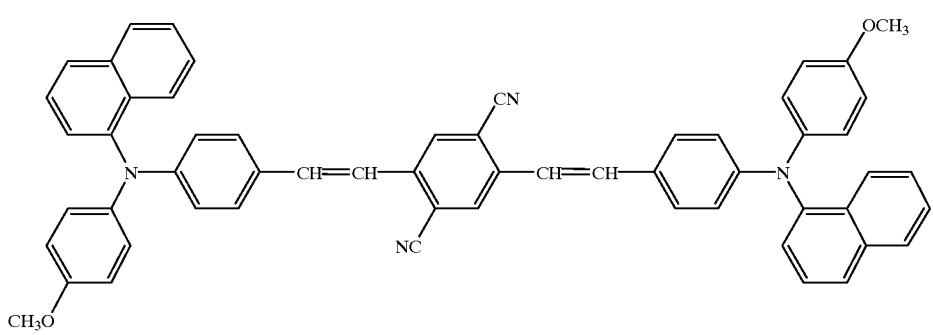

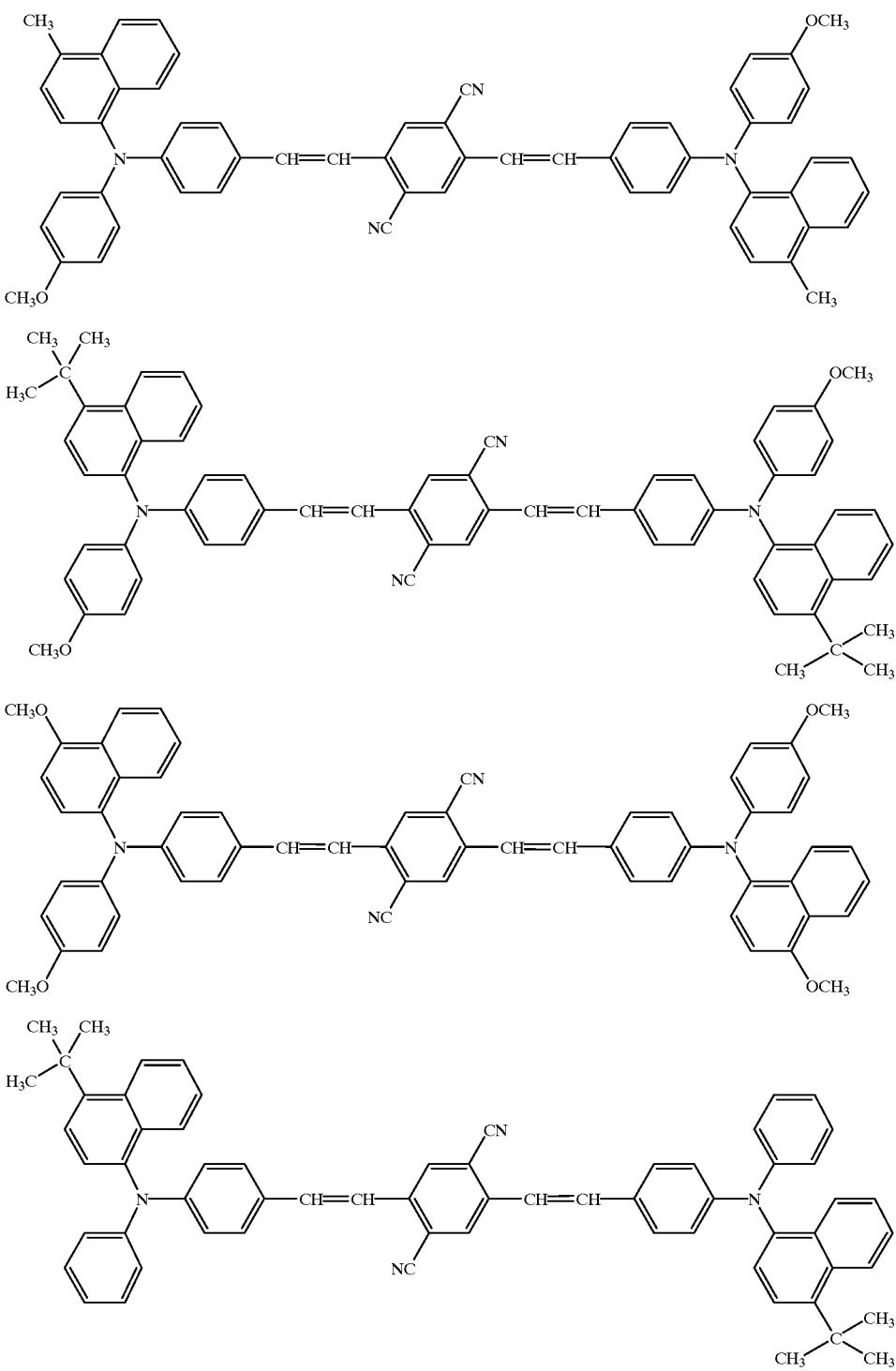

-continued
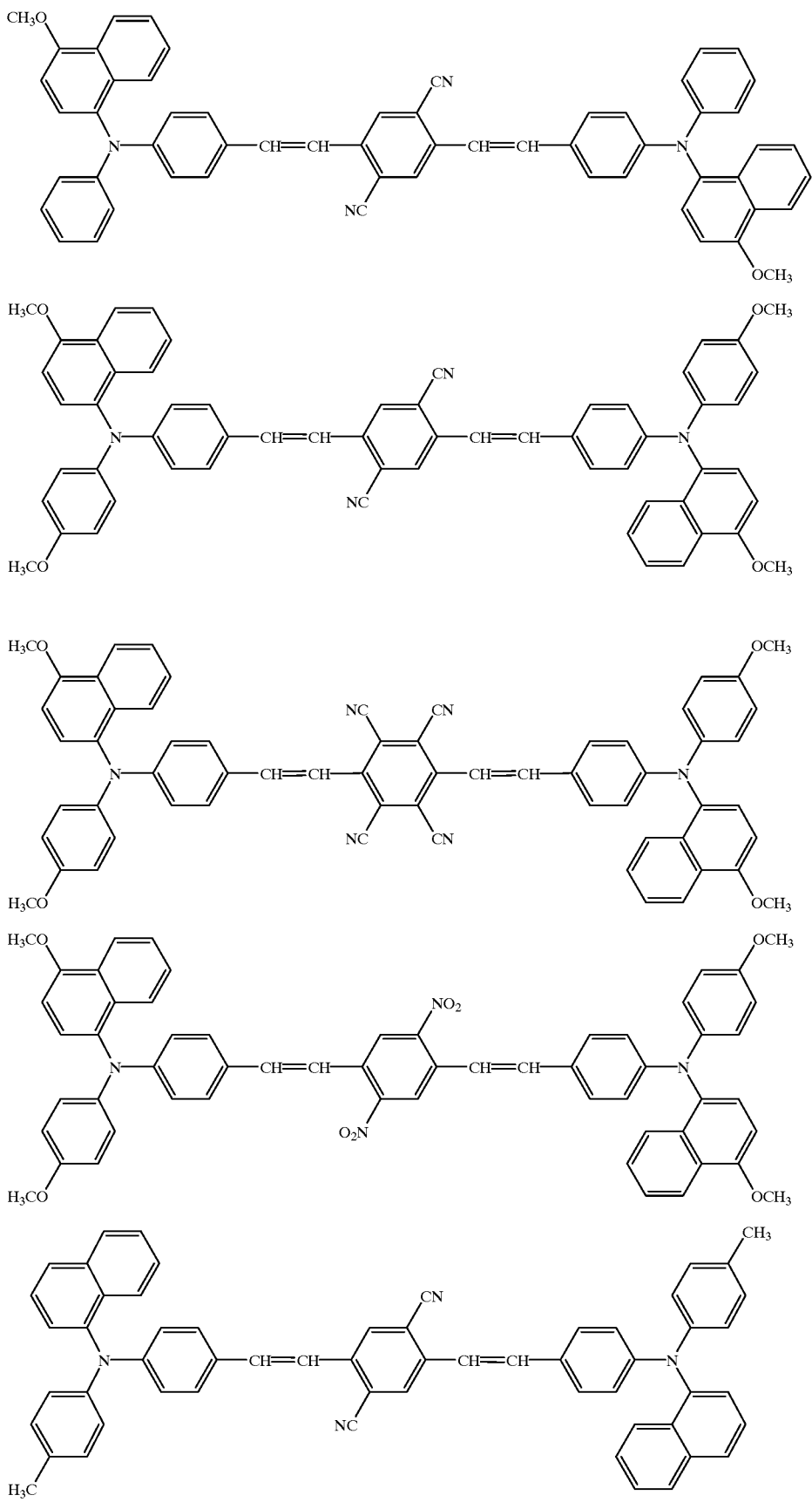

-continued

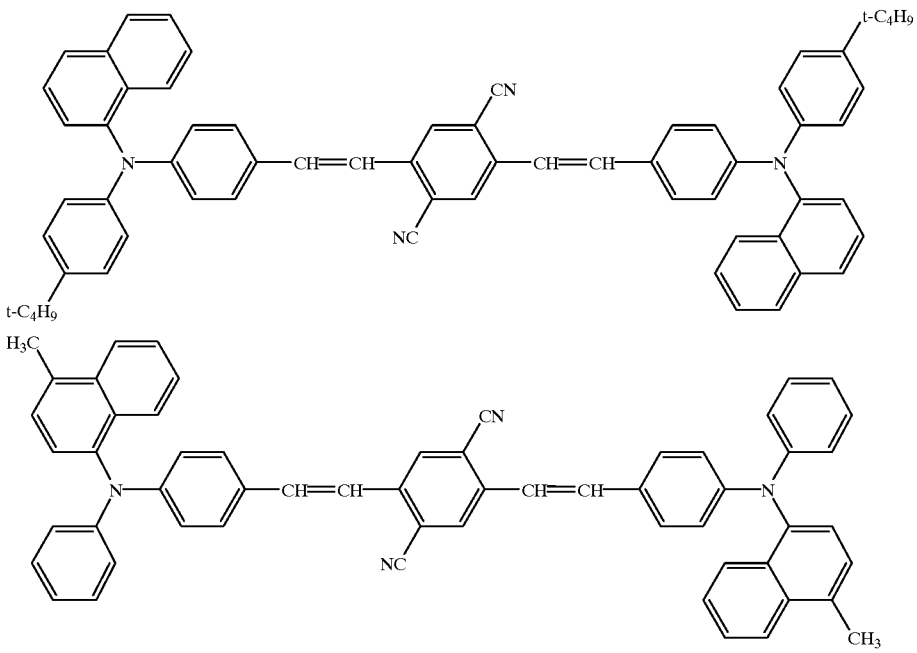

The invention also provides a process for preparing the bis(aminostyryl)benzene compound of the afore-indicated general formula [I], [II], [III] or [IV], which comprises subjecting at least one of 4-(N,N-diarylamino)benzaldehydes of the following general formulas [V] and [VI] to condensation with a diphosphonic acid ester of the following general formula [VII] or a diphosphonium of the following general formula [VIII]:

General formula [V]:

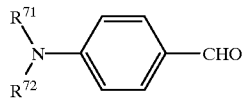

General formula [VI]:

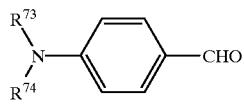

wherein $R^{71}$ and $R^{72}$ independently represent an aryl group corresponding to or as defined before with respect to $R^1$, $R^2$, $R^{14}$, $R^{15}$, $R^{27}$, $R^{28}$, $R^{40}$ or $R^{41}$, and $R^{73}$ and $R^{74}$ independently represent an aryl group corresponding to or as defined before with respect to $R^3$, $R^4$, $R^{16}$, $R^{17}$, $R^{29}$, $R^{30}$, $R^{42}$ or $R^{43}$:

General formula [VII]:

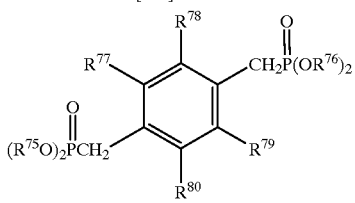

-continued
General formula [VIII]:

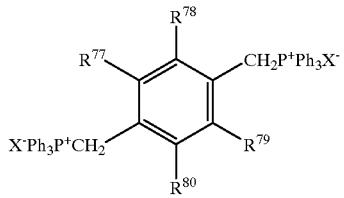

wherein $R^{75}$ and $R^{76}$ may be the same or different and independently represent a hydrocarbon group, preferably a saturated hydrocarbon group having 1 to 4 carbon atoms, $R^{77}$, $R^{78}$, $R^{79}$ and $R^{80}$ independently represent a group corresponding to or defined before with respect to $R^5$, $R^6$, $R^7$, $R^8$, $R^{18}$, $R^{19}$, $R^{20}$, $R^{21}$, $R^{31}$, $R^{32}$, $R^{33}$, $R^{34}$, $R^{44}$, $R^{45}$, $R^{46}$, or $R^{47}$, and X represents a halogen atom.

More particularly, in the process for preparing the compound of the invention, the condensation is carried out according to the Wittig-Horner reaction or Wittig reaction wherein the diphosphonic acid ester or diphosphonium is treated with a base in a solvent to form carbo anions, followed by condensation of the carbo anions with the 4-(N,N-diarylamino)benzaldehyde.

For instance, in order to obtain a bis(aminostyryl)benzene compound of the following general formula [I']:

General formula [I']:

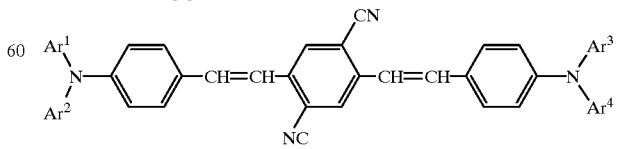

wherein $Ar^1$, $Ar^2$, $Ar^3$ and $Ar^4$, respectively, have the same meanings as defined before, at least one of 4-(N,N-- diarylamino)benzaldehydes of the following general formulas (17) and (18) is condensed with a diphosphonic acid ester of the following general formula (19) or a diphosphonium of the following general formula (20):

wherein $Ar^1$, $Ar^2$, $Ar^3$, $Ar^4$, $R^{75}$, $R^{76}$ and X, respectively, have the same meanings as defined before.

The reaction sequence of the condensation is, for example, as shown in the following Reaction Scheme 1.

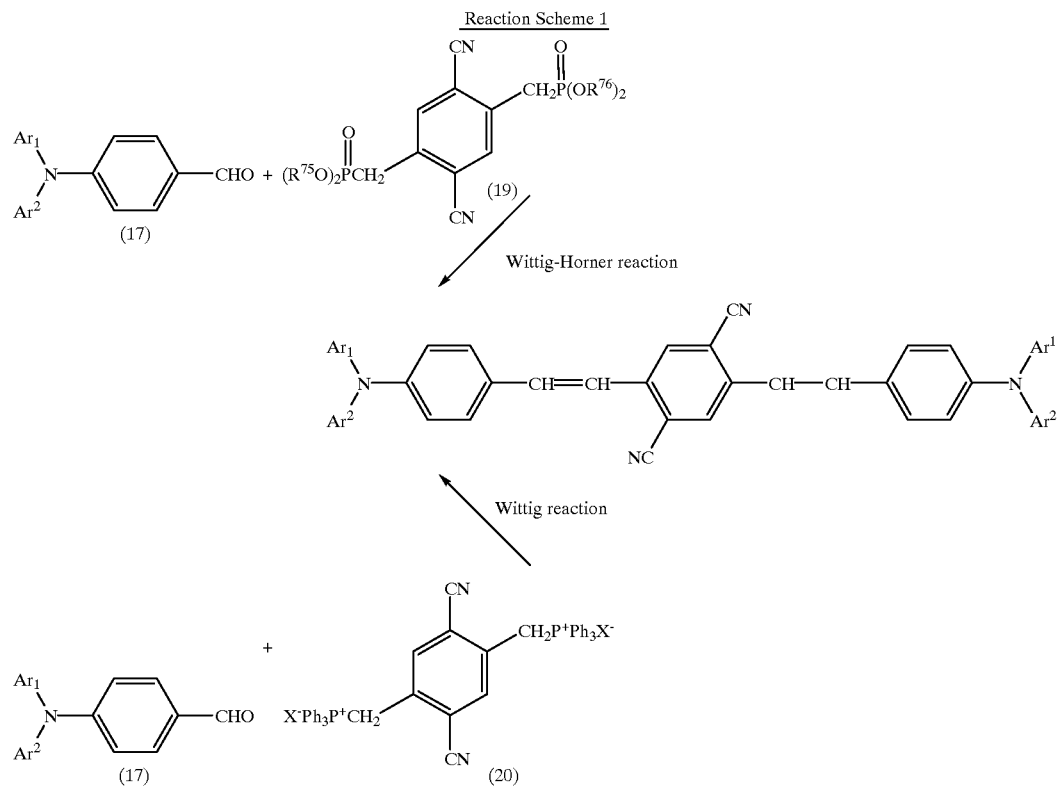

General formula (17):

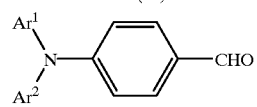

General formula (18):

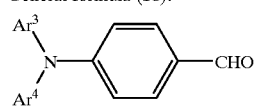

General formula (19):

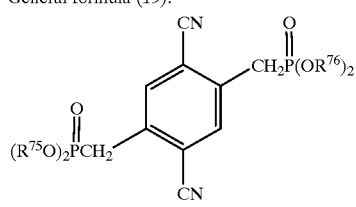

General formula (20):

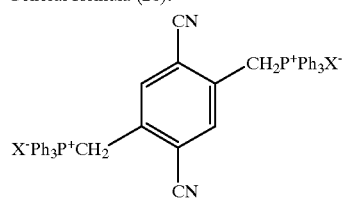

The above reactions start from the formation of a carbo anion by treating the compound of the general formula (19) or (20) with a base in an appropriate solvent, and are completed through condensation of the carbo anion with the aldehyde of the general formula (17). The possible combinations of the bases and the solvents are considered to be ones indicated below.

Such combinations include sodium hydroxide/water, sodium carbonate/water, potassium carbonate/water, sodium ethoxide/ethanol or dimethylformamide, sodium methoxide/methanol-diethyl ether mixed solvent or dimethylformamide, triethylamine/ethanol, diglyme, chloroform or nitromethane, pyridine/methylene chloride or nitromethane, 1,5-diazacycl[4.3.0]non-5-ene/dimethylsulfoxide, potassium t-butoxide/dimethylsulfoxide or tetrahydrofuran, butyl lithium/diethyl ether, tetrahydrofuran, benzene or dimethylformamide, phenyl lithium/diethyl ether or tetrahydrofuran, sodium amide/ammonia, sodium hydride/dimethylformamide or tetrahydrofuran, triethyl sodium/diethyl ether or tetrahydrofuran, and the like.

The reaction proceeds at a relatively low temperature of −30° C. to 30° C. and is selective, so that purification of the intended product through chromatography is easy. In addition, the compound of the invention represented by the general formula [I'] exhibits high crystallinity, and thus, purity can be improved by re-crystallization. The manner of the re-crystallization is not critical, and it is simple to dissolve the product in acetone and add hexane to the resulting solution. The subsequent removal of the solvent through distillation is easy. The reaction may be effected at a temperature of normal temperatures to 30° C. at normal pressures for 3 to 24 hours.

According to the above process for preparing the compounds of the invention, there can be obtained bis(aminostyryl)benzene compounds of the afore-indicated general formulas (10), (11), (12), (13), (14) and (15). More particularly, there can be obtained bis(aminostyryl)benzene compounds of the afore-indicated structural formulas (16)-1, (16)-2, (16)-3, (16)-4, (16)-5, (16)-6 and (16)-7.

The invention also provides various compounds suitable as synthetic intermediates of the inventive compounds.

More particularly, mention is made of 4-(N,N-diarylamino)benzaldehyde which is represented by the general formula [V] or [VI] and is used as a synthetic intermediate for bis(aminostyryl)benzene compounds represented by the general formulas [I], [II], [III] and [IV].

This synthetic intermediate (hereinafter referred to as inventive synthetic intermediate 1) is represented by the afore-indicated general formula (17) or (18), more particularly, by the following general formula (21), (22), (23), (24), (25) or (26), with its specific examples including those represented by the following structural formulas (27)-1, (27)-2, (27)-3, (27)-4, (27)-5, (27)-6 and (27)-7:

General formula (21):

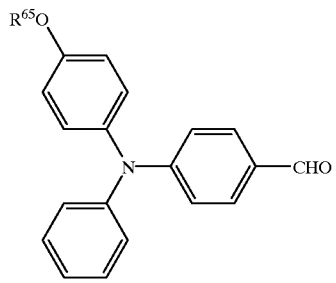

wherein $R^{65}$ represents a saturated or unsaturated hydrocarbon group having from 2 to 4 carbon atoms:

General formula (22):

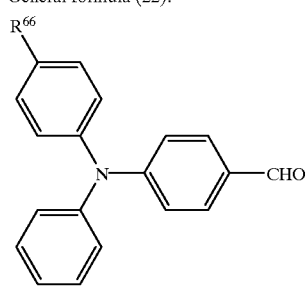

wherein $R^{66}$ represents a saturated or unsaturated hydrocarbon group having from 1 to 4 carbon atoms:

General formula (23):

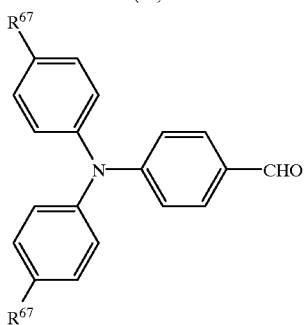

wherein $R^{67}$ represents a saturated or unsaturated hydrocarbon group having from 1 to 4 carbon atoms:

General formula (24):

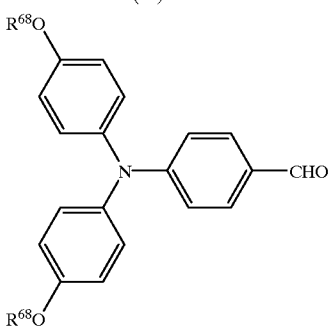

wherein $R^{68}$ represents a saturated or unsaturated hydrocarbon group having from 1 to 4 carbon atoms:

General formula (25):

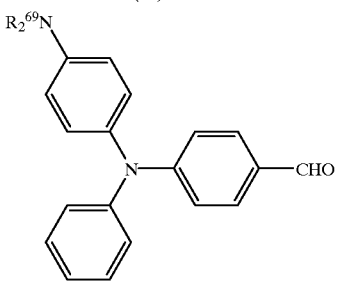

wherein $R^{69}$ represents a saturated or unsaturated hydrocarbon group having from 1 to 4 carbon atoms:

General formula (26):

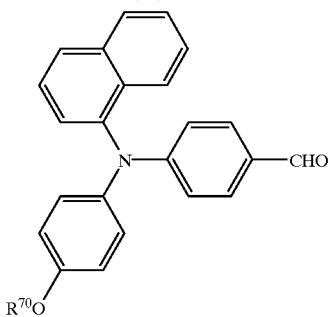

wherein $R^{70}$ represents a saturated or unsaturated hydrocarbon group having from 1 to 4 carbon atoms:

Structural formula (27)-1:

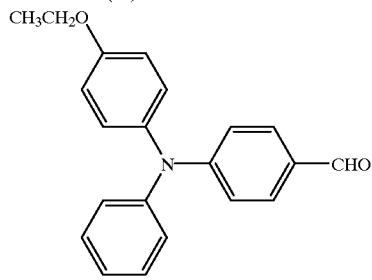

Structural formula (27)-2:

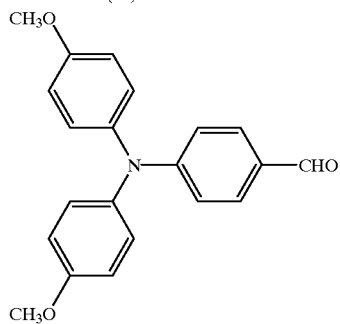

Structural formula (27)-3:

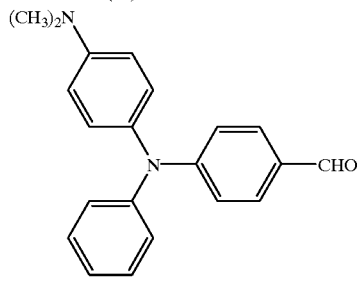

Structural formula (27)-4:

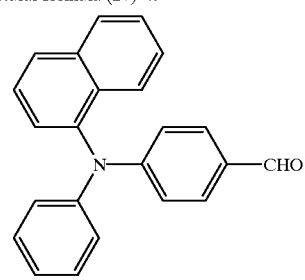

Structural formula (27)-5:

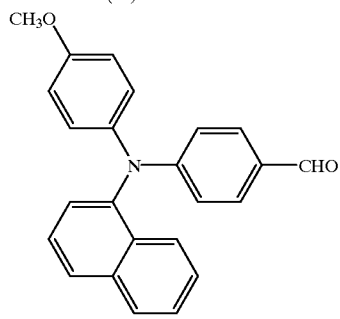

-continued

Structural formula (27)-6:

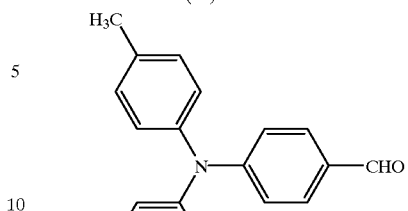

Structural formula (27)-7:

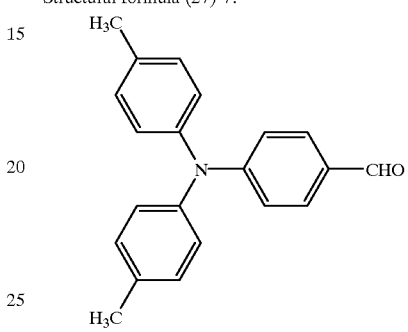

The inventive synthetic intermediate 1 can be led from a synthetic intermediate or precursor in the following manner.

A triarylamine (hereinafter referred to as inventive synthetic intermediate 2), which is represented by the following general formula [IX] or [X] and is used as a synthetic intermediate of the bias(aminostyryl)benzene compound of the afore-indicated general formula [I], [II], [III] or [IV], is formulated with an adduct of dimethylformamide and phosphorus oxychloride to obtain a 4-(N,N-diarylamino) benzaldehyde of the afore-indicated general formula [V] or [VI], which serves as the synthetic intermediate 1 for the bis(aminostyryl)benzene compound. The formulated reaction may be carried out at room temperature (20° C.) to 80° C. at normal pressures for 3 to 24 hours:

General formula [IX]:

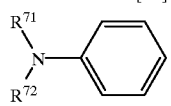

General formula [X]:

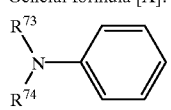

wherein $R^{71}$ and $R^{72}$ independently represent an aryl group corresponding to or defined before with respect to $R^1$, $R^2$, $R^{14}$, $R^{15}$, $R^{27}$, $R^{28}$, $R^{40}$ or $R^{41}$, and $R^{73}$ and $R^{74}$ independently represent an aryl group corresponding to or defined before with respect to $R^3$, $R^4$, $R^{16}$, $R^{17}$, $R^{29}$, $R^{30}$, $R^{42}$ or $R^{43}$.

The above inventive synthetic intermediate 2 is represented by the afore-indicated general formula [IX] or [X], particularly represented by the following general formula (28) or (29) and more particularly represented by the following general formula (30), (31), (32), (33), (33), (34) or (35) with its specific examples including those of the following structural formulas (36)-1, (36)-2, (36)-3, (36)-4, (36)-5, (36)-6 and (36)-7:

General formula (28):

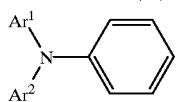

General formula (29):

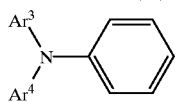

wherein $Ar^1$, $Ar^2$, $Ar^3$ and $Ar^4$, respectively, have the same meanings as defined before:

General formula (30):

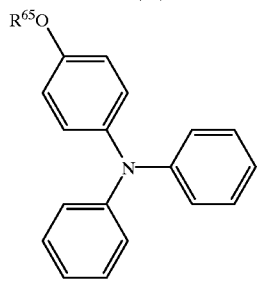

wherein $R^{65}$ represents a saturated or unsaturated hydrocarbon group having from 2 to 4 carbon atoms:

General formula (31):

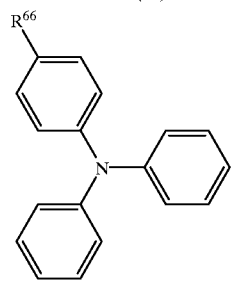

wherein $R^{66}$ represents a saturated or unsaturated hydrocarbon group having from 1 to 4 carbon atoms:

General formula (32):

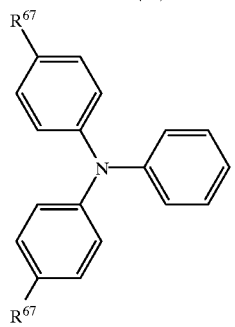

wherein $R^{67}$ represents a saturated or unsaturated hydrocarbon group having from 1 to 4 carbon atoms:

General formula (33):

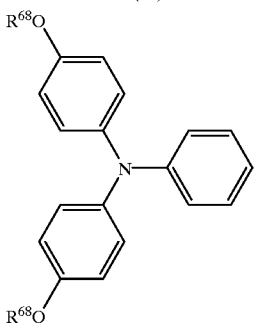

wherein $R^{68}$ represents a saturated or unsaturated hydrocarbon group having from 1 to 4 carbon atoms:

General formula (34):

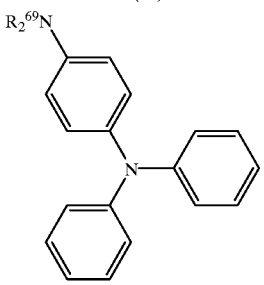

wherein $R^{69}$ represents a saturated or unsaturated hydrocarbon group having from 1 to 4 carbon atoms:

General formula (35):

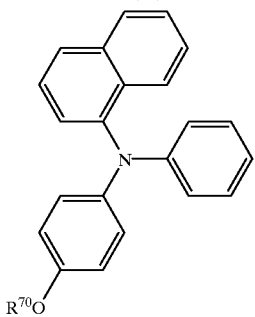

wherein $R^{70}$ represents a saturated or unsaturated hydrocarbon group having from 1 to 4 carbon atoms:

Structural formula (36)-1:

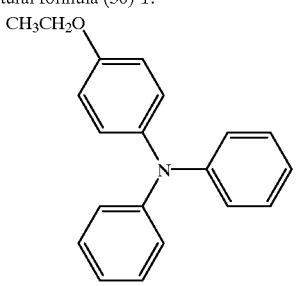

Structural formula (36)-2:
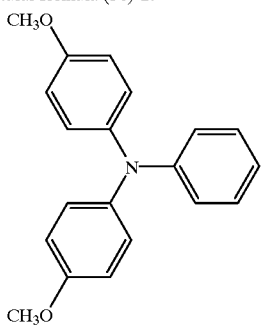

Structural formula (36)-3:
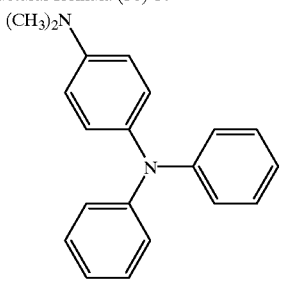

Structural formula (36)-4:
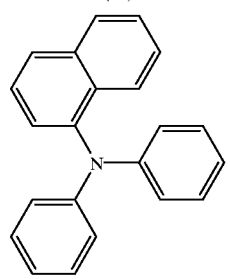

Structural formula (36)-5:
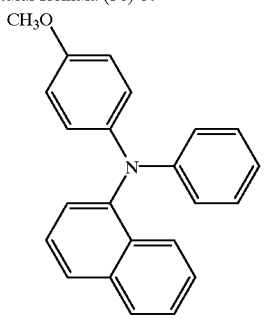

Structural formula (36)-6:
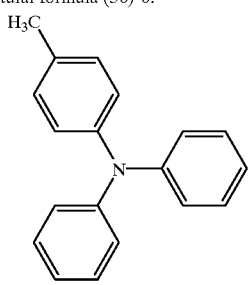

Structural formula (36)-7:
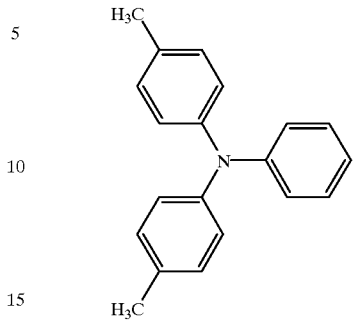

The inventive synthetic intermediate 2 can be synthesized in the following manner.

The diarylamine of the following general formula [XI] and the halogenated benzene of the following general formula [XII] are subjected to coupling in the presence of a catalyst and a base, or the diarylamine of the following general formula [XIII] and the halogenated aryl compound of the following general formula [XIV] are subjected to coupling in the presence of a catalyst and a base, thereby obtaining a triarylamine as the synthetic intermediate 2:

General formula [IX]:
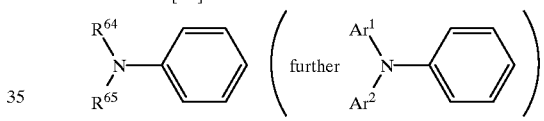

General formula [X]:
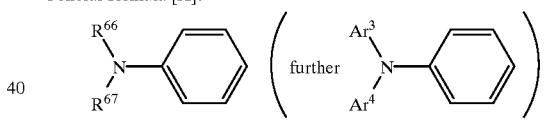

General formula [XI]:
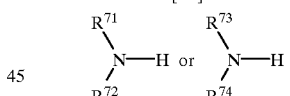

General formula [XII]:
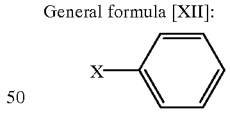

General formula [XIII]:
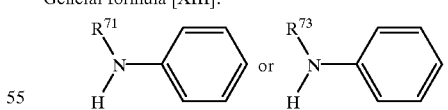

General formula [XIV]:

$X-R^{72}$ or $X-R^{74}$

In the above general formulas [IX], [X], [XI], [XII], [XIII] and [XIV], $R^{71}$ and $R^{72}$ independently represent an aryl group corresponding to or defined before with respect to $R^1$, $R^2$, $R^{14}$, $R^{15}$, $R^{27}$, $R^{28}$, $R^{40}$ or $R^{41}$, $R^{73}$ and $R^{74}$ independently represent an aryl group corresponding to or defined before with respect to $R^3$, $R^4$, $R^{16}$, $R^{17}$, $R_{29}$, $R^{30}$, $R^{42}$ or $R^{43}$, and X represents a halogen atom.

The catalyst used for the synthetic reaction of the inventive synthetic intermediate 2 includes, Cu, CuX, $CUX_2$, CuO, $Pd(CH_3COO)_2$, $Pd(PR_3)_4$ and the like, in which R represents a phenyl group or an alkyl group, and X represents a halogen atom. The bases include $K_2CO_3$, $Ca_2CO_3$, NaOH, BuONa, PrONa, $C_2H_5$Ona, $CH_3$Ona and the like. This reaction is favorably carried out at a reaction temperature of 100 to 200° C. under a normal pressure for a reaction time of 2 to 48 hours in a solvent such as dimethylformamide, dimethylsulfoxide, nitrobenzene, dichlorobenzene, xylene or the like.

The invention also provides, as an inventive synthetic intermediate, a diphosphonic acid ester of the afore-indicated general formula [VII] or a diphosphonium of the afore-indicated general formula [VIII] (hereinafter referred to simply as synthetic intermediate 3).

This synthetic intermediate 3 is represented by the following general formula (19) or (20):

General formula (19):

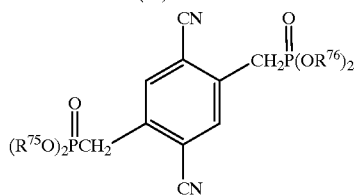

General formula (20):

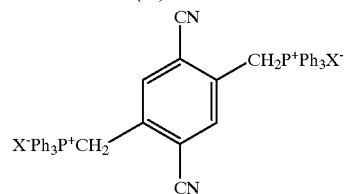

The synthetic intermediate 3 of the invention can be derived from a synthetic intermediate or precursor in the following manner.

A halogenated aryl compound of the following general formula [XV] and a trialkyl phosphite of the following general formula [XVI] or triphenylphosphine ($PPh_3$) are reacted to obtain a diphosphinic acid ester of the following general formula [VII] or a diphosphonium of the following general formula [VIII] as synthetic intermediate 3. This reaction is favorably carried out at a reaction temperature of 120 to 160° C. under a normal pressure for a time of 30 minutes to 12 hours in a solvent-free condition or in an excess solvent such as a trialkyl phosphite or xylene:

General formula [XV]:

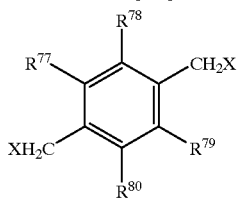

wherein $R^{77}$, $R^{78}$, $R^{79}$ and $R^{80}$, respectively, represent groups which may be the same or different provided that at least one of them is a hydrogen atom, a cyano group, a nitro group or a halogen atom, and X represents a halogen atom:

General Formula [XVI]:

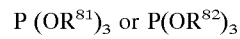

$P(OR^{81})_3$ or $P(OR^{82})_3$ wherein $R^{81}$ and $R^{82}$ are, respectively, hydrocarbon groups which may be the same or different, preferably a saturated or unsaturated hydrocarbon group having 1 to 4 carbon atoms and, respectively, correspond to a group defined with respect to $R^{75}$ or $R^{76}$.

The invention provides a halogenated aryl compound of the afore-indicated general formula [XV] (hereinafter referred to as synthetic intermediate 4) as an synthetic intermediate for preparing the synthetic intermediate 3.

The synthetic intermediate 4 of the invention is obtained by reacting a xylene compound of the following general formula [XVII] with an N-halogenated succinimide of the following general formula [XVIII] under irradiation of light. The reaction is performed in a solvent such as carbon tetrachloride, chloroform, benzene or the like under irradiation of light of a 100 to 500 W light source, such as a high pressure mercury lamp, a low pressure mercury lamp, a xenon lamp, a halogen lamp or the like, at a temperature of 20 to 60° C. under a normal pressure for a reaction time of 0 minutes to 48 hours:

General formula [XVII]:

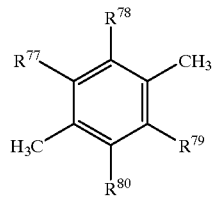

wherein $R^{77}$, $R^{78}$, $R^{79}$ and $R^{80}$ are, respectively, groups which may be the same or different provided that at least one of them is a hydrogen atom, a cyano group, a nitro group or a halogen atom:

General formula [XVIII]:

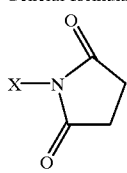

wherein X represents a halogen atom.

The reactions for obtaining the respective synthetic intermediates stated above can be shown according to the following reaction schemes 2 and 3:

Reaction Scheme 2

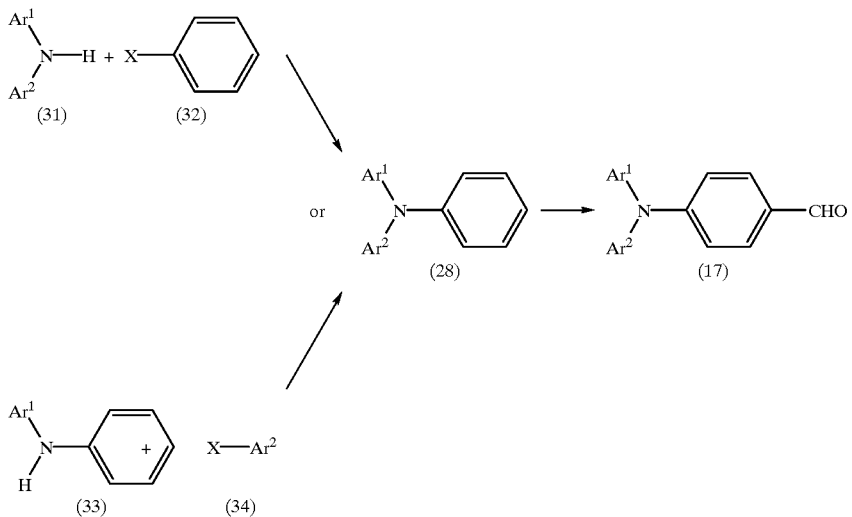

Reaction Scheme 3

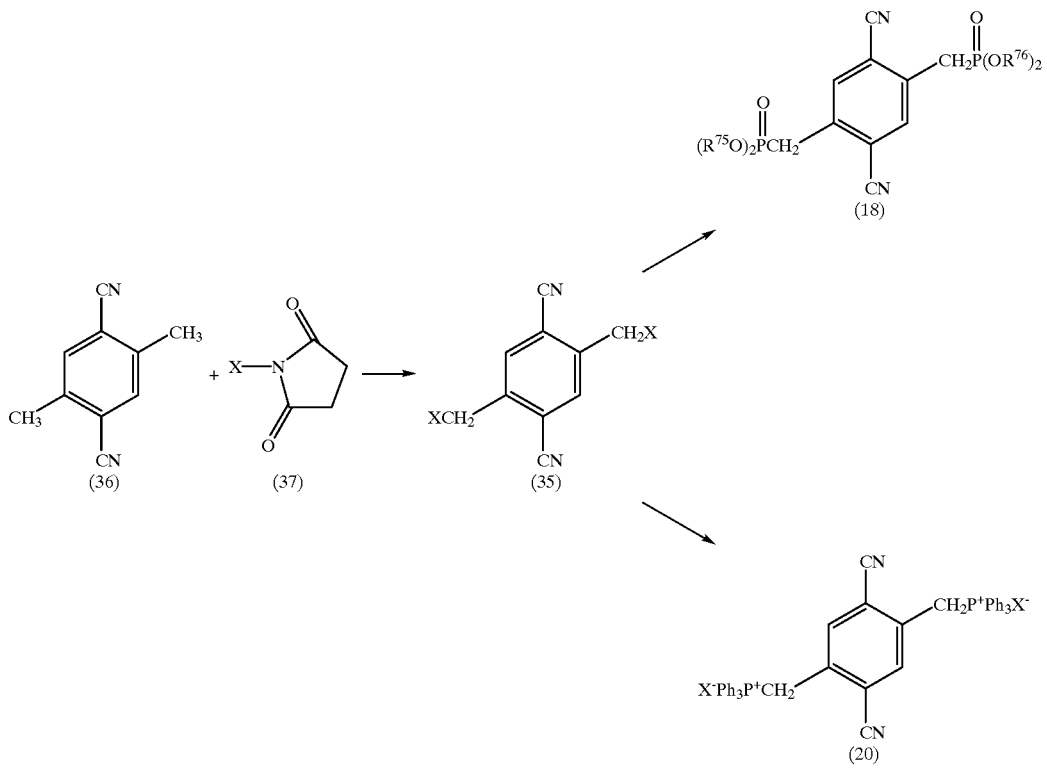

FIGS. 32 to 35 are, respectively, views showing organic electroluminescent devices (EL devices) using the compounds of the invention as an organic luminescent material.

Figure 32:
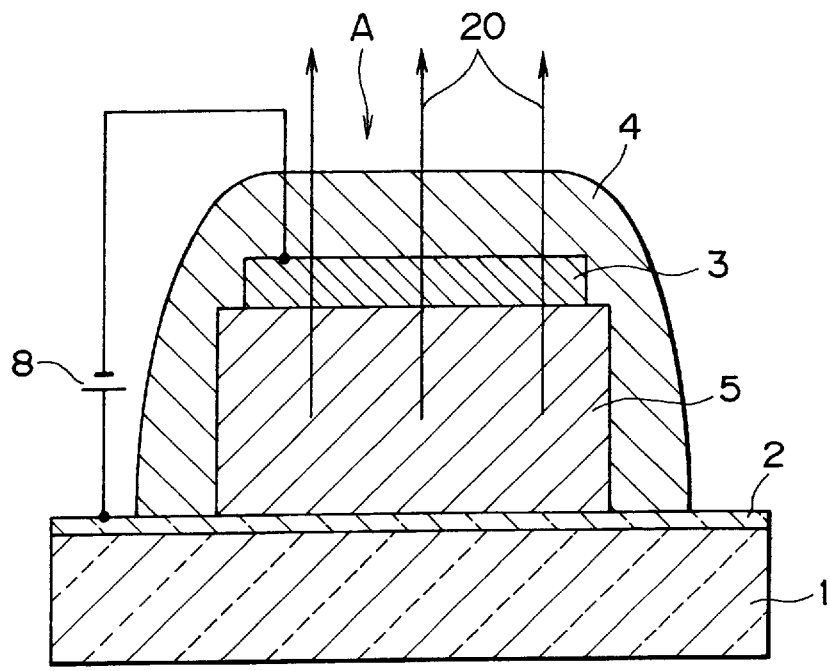
FIG. 32 is a schematic sectional view showing an essential part of an organic electroluminescent device according to one embodiment of the invention.
Figure 33:
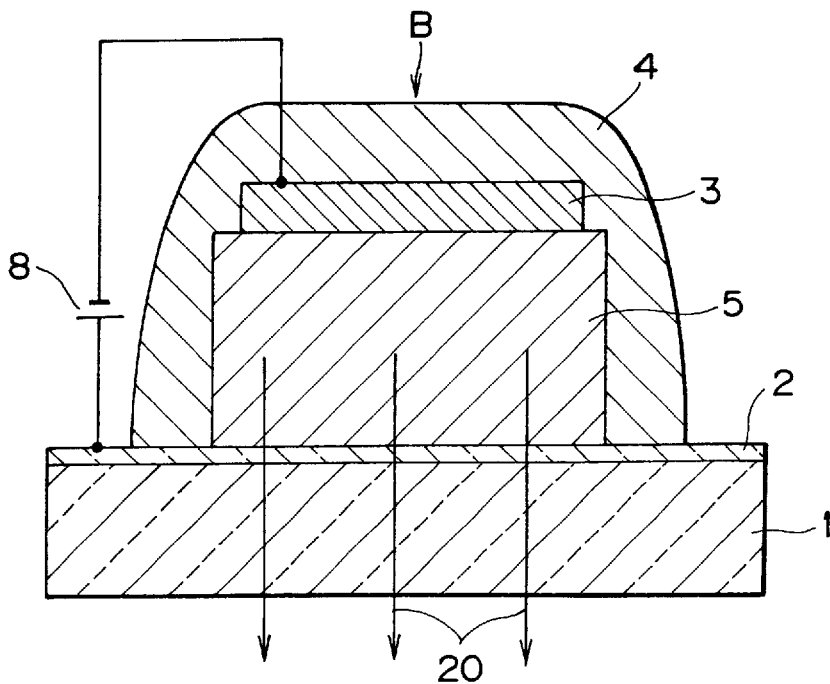
FIG. 33 is a schematic sectional view showing an essential part of an organic electroluminescent device according to another embodiment of the invention.

FIG. 32 shows organic electroluminescent device A of a transmission type in which luminescent light 20 can also be observed from a side of a protective layer 4. FIG. 33 shows organic electroluminescent device B of a reflection type wherein light reflected at a cathode 3 can also be obtained as luminescent light 20.

In the figures, reference numeral 1 indicates a substrate for forming an organic electroluminescent device, which may be made of glass, plastics and other appropriate materials. Where the organic electroluminescent device is used in combination with other types of display devices, the substrate 1 may be commonly used. Reference numeral 2 indicates a transparent electrode (anode), for which ITO (indium tin oxide), $SnO_2$ or the like may be used.

Reference numeral 5 indicates an organic luminescent layer, which contains the compound of the invention as a luminescent material. For a layer arrangement for obtaining the organic electroluminescent light 20, hitherto known various types of arrangements may be used. As is described hereinafter, if a material for either a hole transport layer or an electron transport layer has luminescent properties, for example, a built-up structure of these thin films may be used. Further, in order to increase charge transportability within a range satisfying the purposes of the invention, either or both of a hole transport layer and an electron transport layer have a built-up structure of thin films made of plural types of materials, or a thin film composed of a mixture of plural types of materials may be used without limitation. In addition, in order to improve luminescent properties, at least one fluorescent material may be used to provide a structure wherein a thin film of the fluorescent material is sandwiched between a hole transport layer and an electron transport layer. Alternatively, another type of structure may be used wherein at least one fluorescent material is present in a hole transport layer or an electron transport layer, or in both. In these cases, in order to improve a luminescent efficiency, a thin film for controlling the transport of holes or electrons may be incorporated in a layer arrangement.

Where the compounds of the invention have both electron transportability and electron transportability, they can be used as a luminescent layer serving also as an electron transport layer, or as a luminescent layer serving as a hole transport layer in the device arrangement. Moreover, it is possible to provide an arrangement wherein the compound of the invention is formed as a luminescent layer sandwiched between an electron transport layer and a hole transport layer.

It will be noted that in FIGS. 32 and 33, reference numeral 3 indicates a cathode, and an electrode material therefor may be made of an alloy of an active metal such as Li, Mg, Ca or the like, and a metal such as Ag, Al, In or the like. Alternatively, a built-up structure of thin films of these metals may also be used. In the transmission-type organic electroluminescent device, an optical transmission required for an intended application can be obtained by controlling a cathode thickness. In the figures, reference numeral 4 indicates a sealing/protecting layer, and when an organic electroluminescent device is wholly covered therewith, its effect increases. Appropriate materials may be used for this purpose provided that air tightness is ensured. Reference numeral 8 indicates a drive power supply for current charge.

In the organic electroluminescent device of the invention, the organic layer may have an organic built-up structure (single hetero structure) wherein a hole transport layer and an electron transport layer are built up and wherein the compound of the invention is used as a material for forming the hole transport layer or electron transport layer. Alternatively, the organic layer may have an organic built-up structure (double hetero structure) wherein a hole transport layer, a luminescent layer and an electron transport layer are successively built up, and the luminescent layer is formed of the compound of the invention.

An example of an organic electroluminescent device having such an organic built-up structure is shown. More particularly, FIG. 34 shows organic electroluminescent device C having a single hetero structure which comprises a built-up structure including, on an optically transparent substrate 1, an optically transparent anode 2, an organic layer 5a consisting of a hole transport layer 6 and an electron transport layer 7, and a cathode 3 superposed successively in this order, and the built-up layer structure is sealed with the protective layer 4.

Figure 34:
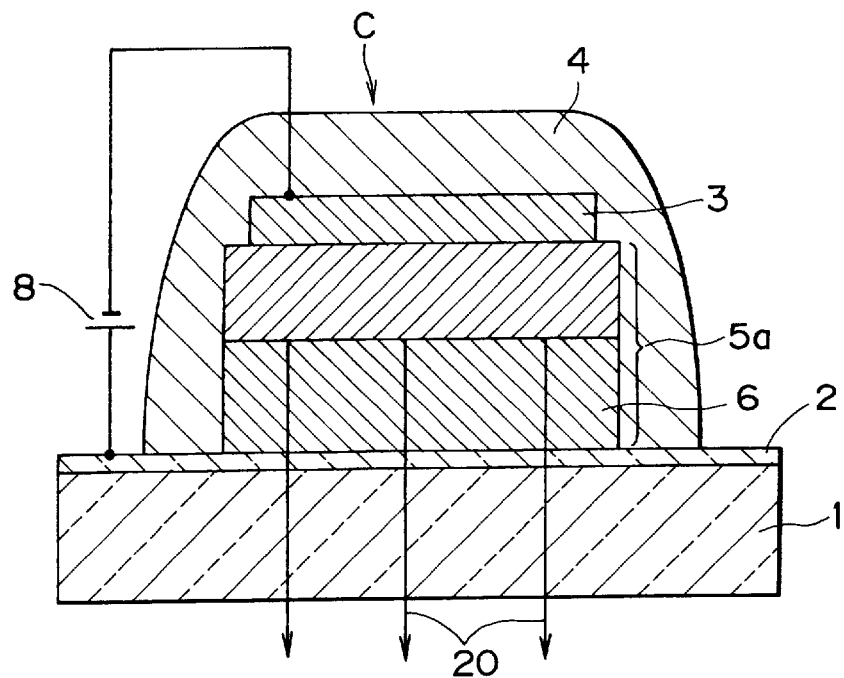
FIG. 34 is schematic sectional view showing an essential part of an organic electroluminescent device according to a further embodiment of the invention.

With such a layer arrangement as shown in FIG. 34 wherein a luminescent layer is omitted, luminescence or light 20 with a given wavelength is emitted from the interface between the hole transport layer 6 and the electron transport layer 7. This luminescence is observed from the side of the substrate 1.

Figure 35:
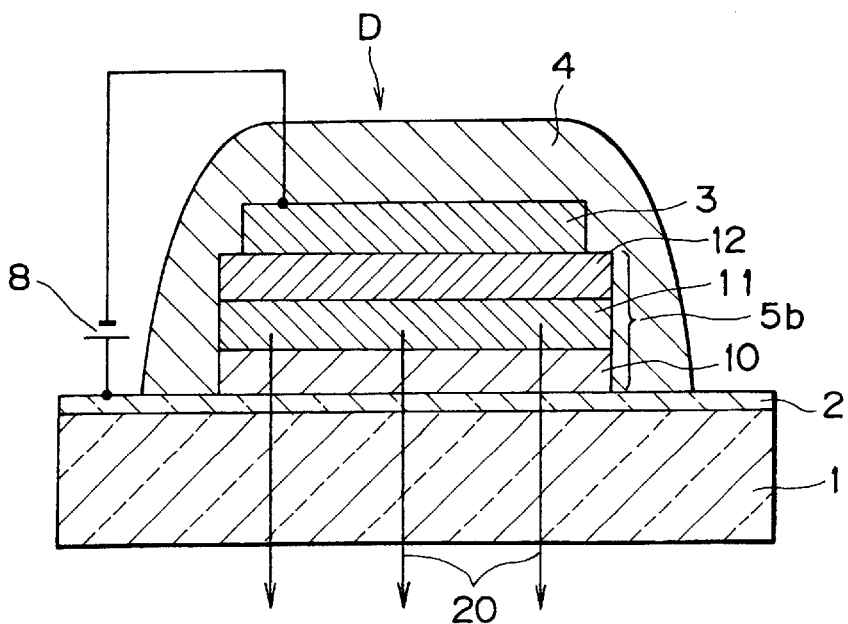
FIG. 35 is a schematic sectional view showing an essential part of an organic electroluminescent device according to a still further embodiment of the invention.

FIG. 35 shows organic electroluminescent device D having a double hetero structure which comprises a built-up structure including, on an optically transparent substrate 1, an optically transparent anode 2, an organic layer 5b consisting of a hole transport layer 10, a luminescent layer 11 and an electron transport layer 12, and a cathode 3 superposed successively in this order. The built-up structure is sealed with a protective layer 4.

In the organic electroluminescent device shown in FIG. 35, when a DC voltage is applied between the anode 2 and the cathode 3, the holes injected from the anode 2 arrives at the luminescent layer 11 via the hole transport layer 10, and the electrons injected from the anode 3 also arrives at the luminescent layer 11 via the electron transport layer 12. Eventually, the electrons/the holes are re-combined in the luminescent layer to generate singlet excitons, thereby causing luminescence with a given wavelength to be generated from the singlet excitons.

In the above-stated organic electroluminescent devices C and D, optically transparent materials such as, for example, glass, plastics and the like may be appropriately used as the substrate 1. Where the devices are used in combination with other types of display devices, or where the built-up structures shown in FIGS. 34 and 35 are arranged in the form of a matrix, the substrate may be commonly used. Both of the devices C and D may have a structure of either a transmission type or a reflection type.

The anode 2 consists of a transparent electrode, for which ITO (indium tin oxide), $SnO_2$ or the like may be used. In order to improve a charge injection efficiency, a thin film made of an organic material or an organometallic compound may be provided between the anode 2 and the hole transport layer 6 (or the hole transport layer 10). It will be noted that where the protective layer 4 is formed of a conductive material such as a metal, an insulating film may be provided at the sides of the anode 2.

The organic layer 5a of the organic electroluminescent device C consists of a built-up organic layer of the hole transport layer 6 and the electron transport layer 7. The compound of the invention may be contained in either or both of these layers to provide a luminescent hole transport layer 6 or electron transport layer 7. The organic layer 5b of the organic electroluminescent device D consists of a built-up organic layer of the hole transport layer 10, the luminescent layer 11 containing the compound of the invention, and the electron transport layer 12. The layer 5b may take other various types of built-up structures. For instance, either or both of the hole transport layer and the electron transport layer may have luminescent properties.

Especially, it is preferred that the hole transport layer 6 or electron transport layer 7, and the luminescent layer 11, respectively, are comprised of a layer made of the compound of the present invention. These layers may be formed of the compound of the invention alone, or may be formed through co-deposition of the compound of the invention and other type of hole or electron transport material (e.g. an aromatic amine, a pyrazoline or the like). Moreover, in order to improve the hole transportability in the hole transport layer, a hole transport layer, which consists of a plurality of hole transport materials being built up, may be formed.

In the organic electroluminescent device C, the luminescent layer may be the electron transport luminescent layer 7. In this case, light may be emitted from the hole transport layer 6 or its interface depending on the voltage applied to from a power supply 8. Likewise, in the organic electroluminescent device D, the luminescent layer may be, aside from the layer 11, the electron transport layer 12 or the hole transport layer 10. For improving the luminescent performance, it is preferred to provide a structure wherein the luminescent layer 11 containing at least one fluorescent material is sandwiched between the hole transport layer and the electron transport layer. Alternatively, a fluorescent material may be contained in the hole transport layer or the electron transport layer, or in both. In this connection, in order to improve a luminescent efficiency, a thin film (such as a hole blocking layer or an exciton-generating layer) for controlling the transport of holes or electrons may be provided in the layer arrangement.

The materials used as the cathode 3 may be alloys of active metals such as Li, Mg, Ca and the like and metals such as Ag, Al, In and the like. Alternatively, a built-up structure of the layers of these metals may also be used. Proper selection in cathode thickness and in type of alloy or metal enables one to fabricate an organic electroluminescent device adapted for its application.

The protective layer 4 acts as a sealing film, and is arranged to wholly cover an organic electroluminescent device therewith, thereby ensuring improved charge injection efficiency and luminescent efficiency. It should be noted that if air tightness is ensured, a material including a single metal such as aluminum, gold, chromium or the like or an alloy thereof may be appropriately selected for this purpose.

The electric current applied to the respective organic electroluminescent devices set out hereinbefore is usually a direct current, but a pulse current or AC current may also be used. The values of current and voltage are not critical provided that they are within ranges not breaking the devices down. Nevertheless, taking into account the power consumption and life of the organic electroluminescent devices, it is preferred to cause luminescence efficiently by use of an electric energy which is as small as possible.

Figure 36:
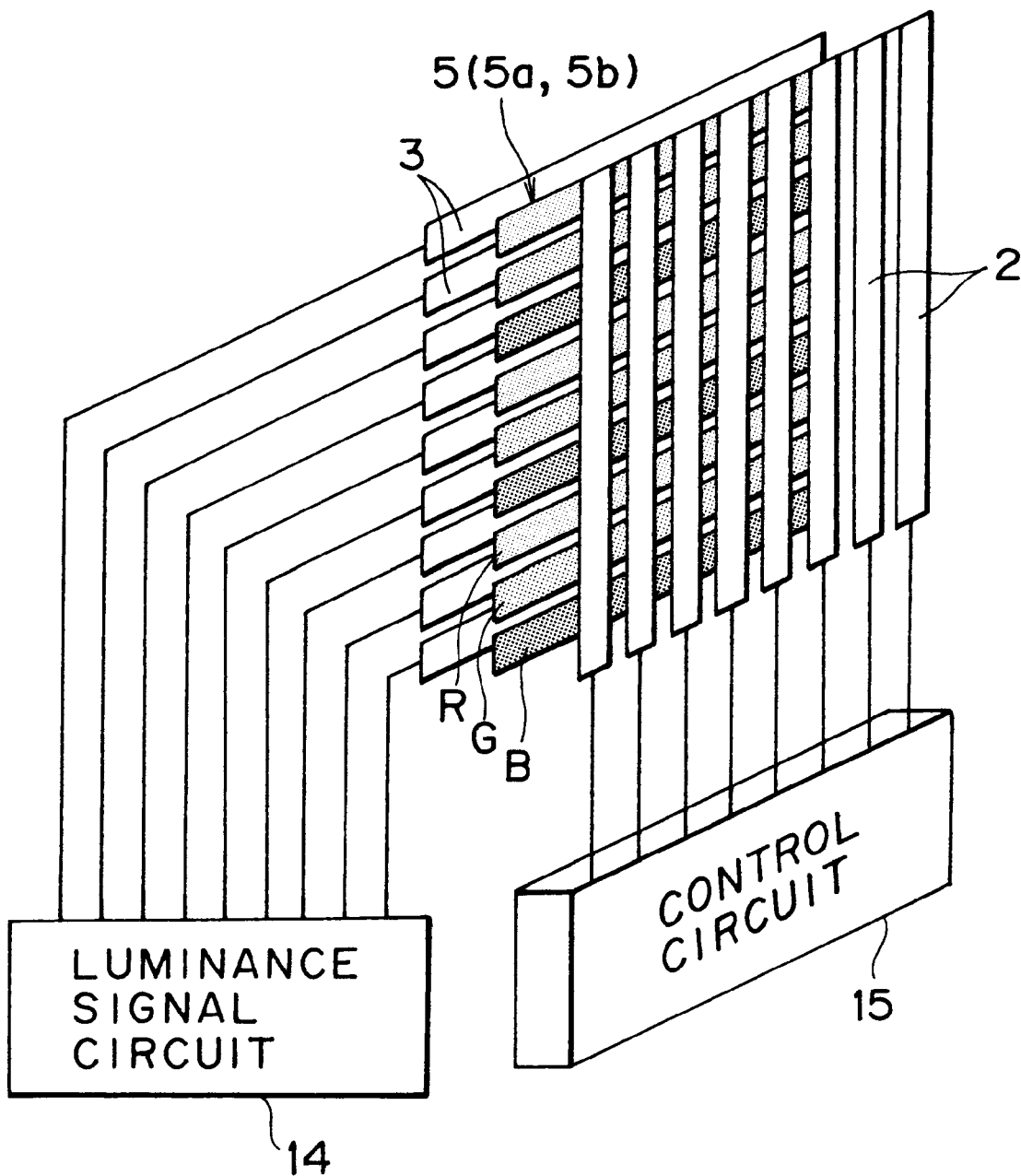
FIG. 36 is a view showing an arrangement of a multicolor or full color flat display using an organic electroluminescent device of the invention.

Next, FIG. 36 shows an arrangement of a flat display, which makes use of an organic electroluminescent device of the invention. As shown in the figure, with the case, for example, of a full color display, organic layers 5 (5a, 5b) capable of generating luminescent three primary colors of red (R), green (G) and blue (B) are arranged between cathodes 3 and anodes 2. The cathodes 3 and the anodes 2 may be provided in the form of stripes in which they are mutually intersected, and are properly selected by means of a luminance signal circuit 14 and a shift register built-in control circuit 15 and applied with a signal voltage thereto. As a result, an organic layer at a position (picture element) where the selected cathode 3 and anode 2 are intersected emits light.

More particularly, FIG. 36 shows, for example, an 8×3 RGB simple matrix wherein a built-up body 5 consisting of a hole transport layer and at least one of a luminescent layer and an electron transport layer is provided between the cathodes 3 and the anodes 2 (see FIG. 34 or 35). The cathodes and anodes are patternized in the form of stripes and are mutually intersected in a matrix, to which signal voltages are applied in time series from the shift register built-in control circuits 15 and 14, thereby causing electroluminescence or light emission at the intersected position. The EL device having such an arrangement may be used not only as a display for letters/symbols, but also as an image reproducing apparatus. Moreover, the striped patterns of the anodes 3 and the cathodes 2 may be arranged for each of red (R), green (G) and blue (B) colors, thus making it possible to fabricate a solid-state flat panel display of the multicolor or full color type.

The invention is more particularly described by way of examples, which should not be construed as limited the invention thereto.

EXAMPLE 1

<Synthetic example of bis(aminostyryl)benzene compound (structural formula (16)-1)>

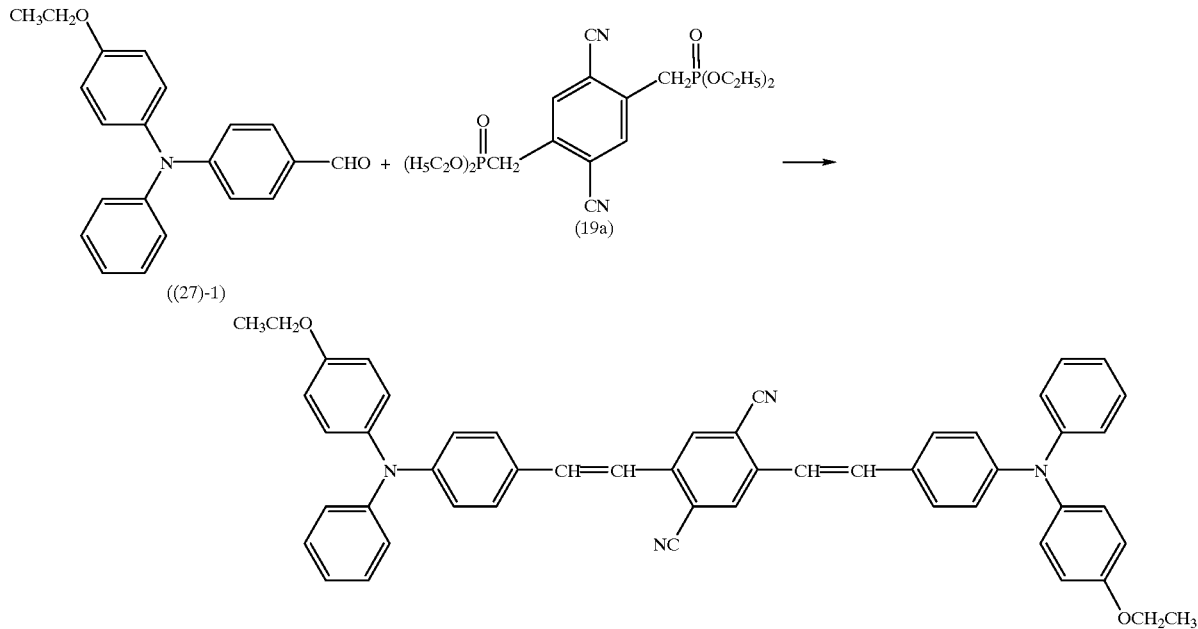

794 mg (4.78 mmols) of triethyl phosphite was dropped in 750 mg (2.39 mmols) of 2,5-di(bromomethyl)-terephthalonitrile, followed by agitation at 125° C. for 30 minutes to obtain diphosphonic acid ester (19a). The ethyl bromide formed by the reaction was distilled off, followed by dissolution in 25 ml of anhydrous tetrahydrofuran (THF) and storage.

18.5 mmols of sodium hydride was suspended in 70 ml of anhydrous tetrahydrofuran, in which the anhydrous tetrahydrofuran solution of the thus obtained diphosphonic acid ester (19a) (corresponding to 2.39 mmols) was dropped in an atmosphere of nitrogen in 15 minutes, followed by agitation at room temperature for 20 minutes.

Subsequently, an anhydrous tetrahydrofuran solution (40 ml) of 1.78 g (5.60 mmols) of 4-[N-phenyl-N-(4-ethoxyphenyl)amino]benzaldehyde (structural formula (27)-1) was further dropped in the mixture in 15 minutes, and agitated at room temperature for 2.5 hours. The reaction mixture was quenched with a small amount of ice, washed with a saturated saline solution and dried over anhydrous sodium sulfate.

The intended product was purified from the reaction mixture through silica gel chromatography (WAKO-gel C-300, tetrahydrofuran:hexane=1:8) and recrystallized from acetone/hexane to obtain 900 mg of the bis (aminostyryl) benzene compound ((16)-1). The yield was found to be at 51% with a glass transition point of 140° C. and a melting point of 180° C. The visible light absorption maximum of the tetrahydrofuran solution was at 475 nm and the fluorescence maximum wavelength was at 590 nm. The $^1$HNMR spectra of the solution were indicated below and also shown in FIG. 1 (it is to be noted that TMS in this and related figures means a peak of trimethylsilane added as a reference substance at the time of measurement of the $^1$HNMR spectra).

NMR (CDCl$_3$) δ (ppm): 1.32 (6H, t), 4.03 (4H, q), 6.83 (4H, d), 6.98–7.22 (22H, m), 7.40 (4H, d), 7.98 (2H, s)

EXAMPLE 2
<Synthetic example of bis(aminostyryl)benzene compound (structural formula (16)-1)>

750 mg (2.39 mmols) of 2,5-di(bromomethyl)-terephthalonitrile and 1.38 g (5.26 mmols) of triphenylphosphine were dissolved in xylene and refluxed for 20 hours. The reaction solution was cooled down to room temperature, and the resultant precipitate was separated by filtration and washed with 5 ml of xylene, dried under reduced pressure and dissolved in 25 ml of anhydrous tetrahydrofuran for storage.

18.5 mmols of sodium hydride was suspended in 70 ml of anhydrous tetrahydrofuran, in which the anhydrous tetrahydrofuran solution of the thus obtained diphosphonium (20a) (corresponding to 2.39 mmols) was dropped in an atmosphere of nitrogen in 15 minutes, followed by agitation at room temperature for 48 hours.

Subsequently, an anhydrous tetrahydrofuran solution (40 ml) of 1.78 g (5.60 mmols) of 4-[N-phenyl-N-(4-ethoxyphenyl)amino]benzaldehyde ((27)-1) was further dropped in the mixture in 15 minutes, and agitated at room temperature for 2.5 hours. The reaction mixture was quenched with a small amount of ice, washed with a saturated saline solution and dried over anhydrous sodium sulfate.

There was obtained 558 mg of the bis (aminostyryl) benzene compound ((16)-1) by purification through silica gel chromatography (WAKO-gel C-300, tetrahydrofuran:hexane=1:8) and recrystallization from acetone/hexane. The yield was found to be at 31%, with various physical properties being coincident with those of the bis (aminostyryl)benzene compound ((16)-1) obtained in Example 1.

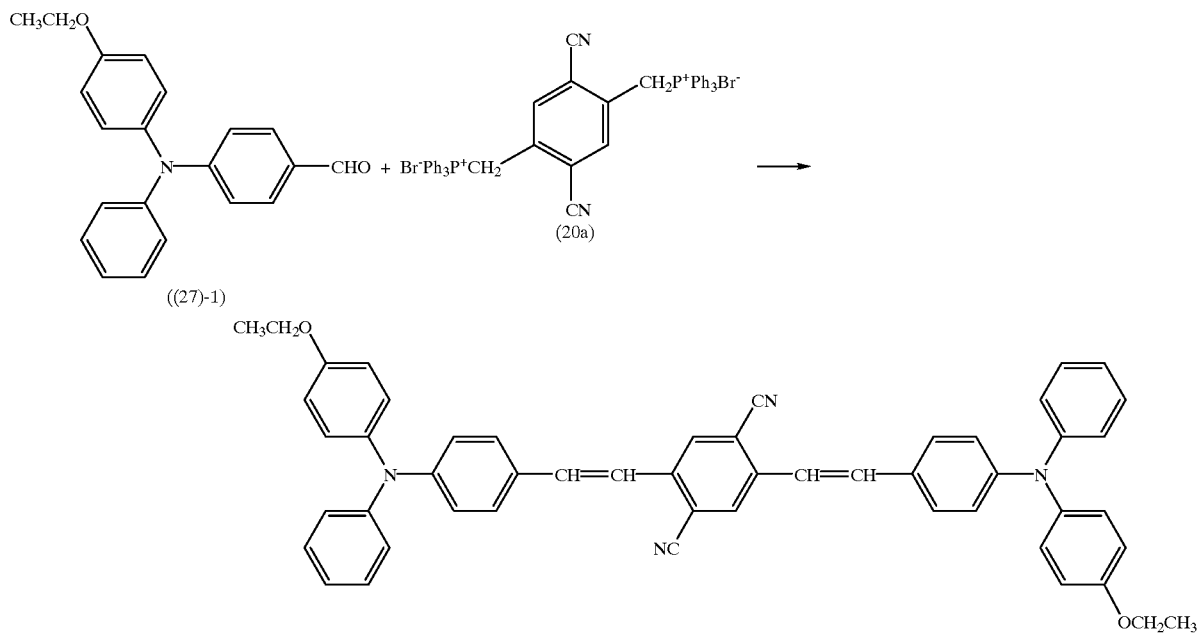

EXAMPLE 3

<Synthetic example of bis(aminostyryl)benzene compound (structural formula (16)-2)>

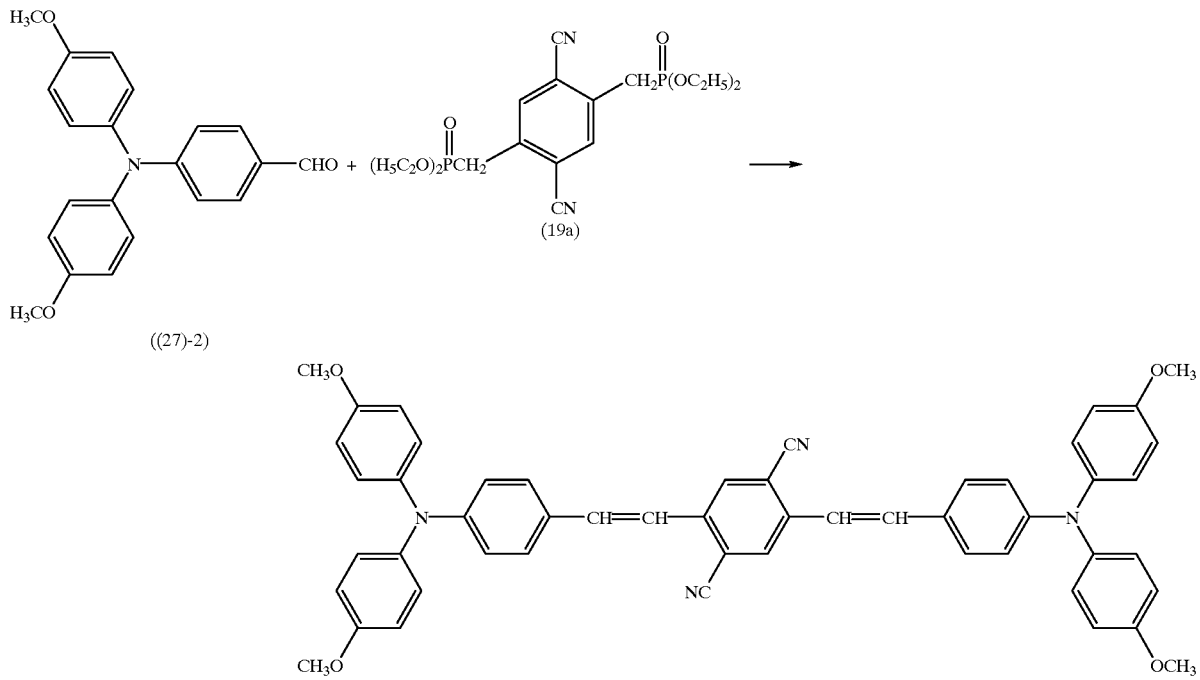

11.3 mmols of sodium hydride was suspended in 20 ml of anhydrous tetrahydrofuran, in which the anhydrous tetrahydrofuran solution of the diphosphonic acid ester (19a) (corresponding to 1.13 mmols) obtained in Example 1 was dropped in an atmosphere of nitrogen in 15 minutes, followed by agitation at room temperature for 20 minutes.

Subsequently, an anhydrous tetrahydrofuran solution (40 ml) of 750 mg (2.25 mmols) of 4-[N,N-di(4-methoxyphenyl)amino]benzaldehyde ((27)-2) was further dropped in the mixture in 15 minutes, and agitated at room temperature for 1 hour. The reaction mixture was quenched with a small amount of ice, washed with a saturated saline solution and dried over anhydrous sodium sulfate.

Figure 2:
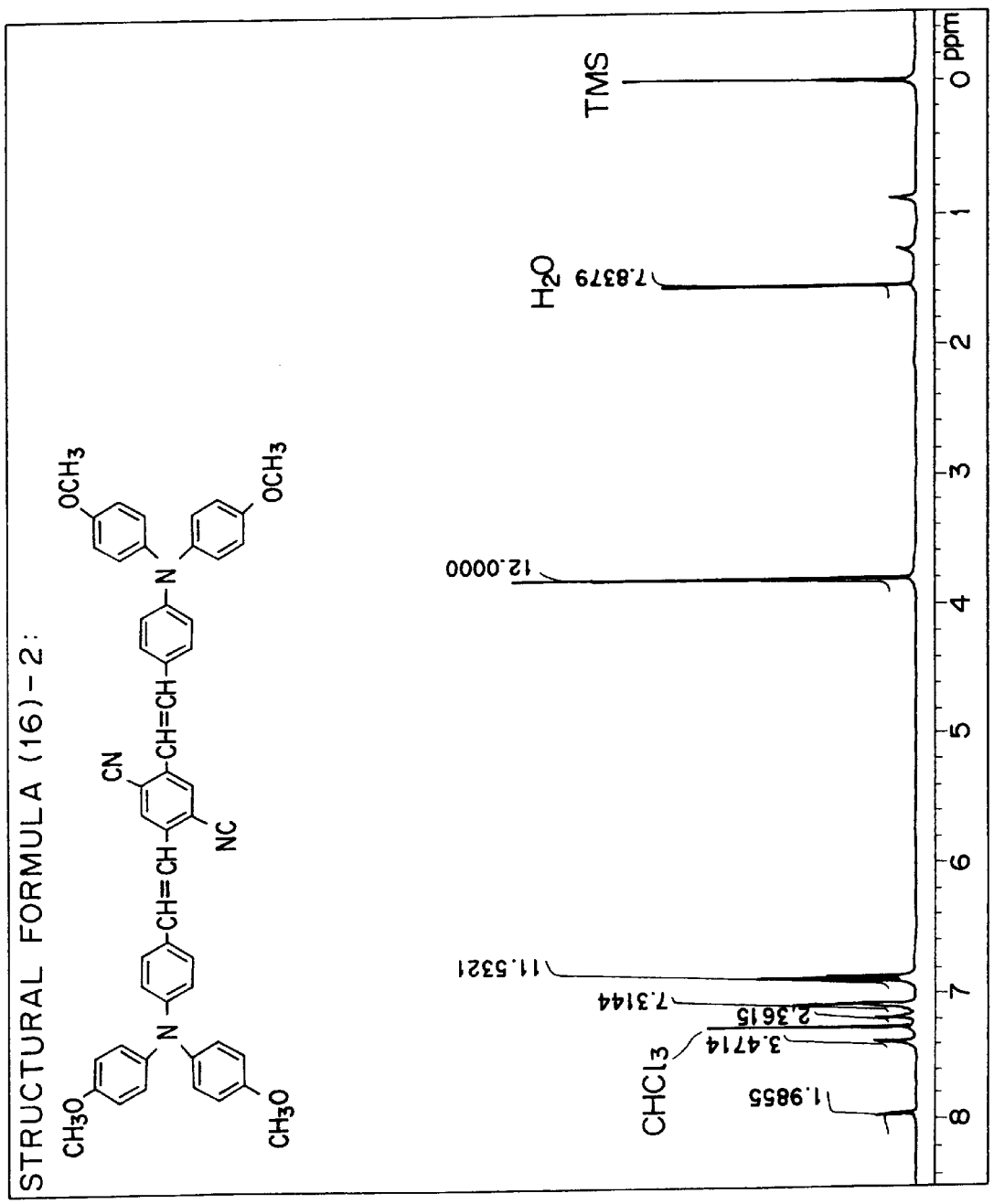
FIG. 2 is an $^1$HNMR spectral diagram of a bis (aminostyryl)benzene compound of structural formula (16)-2 of the invention.

The intended product was purified from the reaction mixture through silica gel chromatography (WAKO-gel C-300, tetrahydrofuran:hexane=1:8) and recrystallized from acetone/hexane to obtain 488 mg of the bis (aminostyryl) benzene compound ((16)-2). The yield was found to be at 31% with a glass transition point of 130° C. and a melting point of 170° C. The visible light absorption maximum of the tetrahydrofuran solution was at 486 nm and the fluorescence maximum wavelength was at 620 nm. The $^1$HNMR spectra of the solution were indicated below and also shown in FIG. 2.

NMR (CDCl$_3$) δ (ppm): 3.81 (12H, s), 6.84 (12H, m), 7.05 (8H, d), 7.19 (2H, d), 7.39 (4H, d), 7.98 (2H, s)

EXAMPLE 4

<Synthetic example of bis(aminostyryl)benzene compound (structural formula (16)-3)>

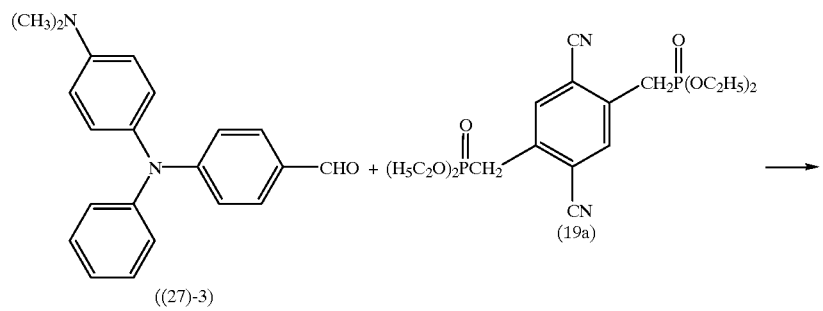

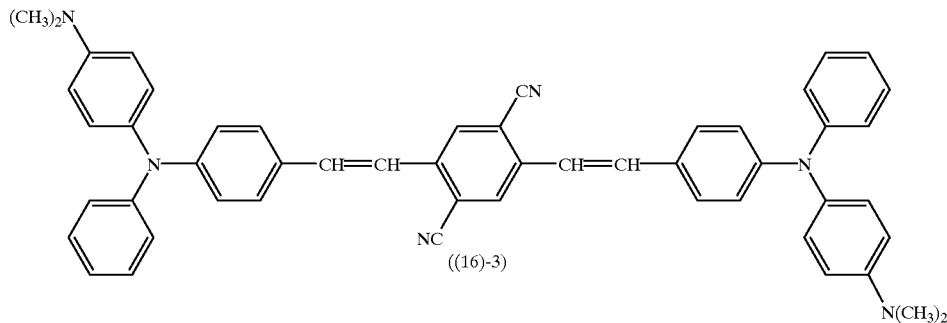

((16)-3)

5.50 mmols of sodium hydride was suspended in 20 ml of anhydrous tetrahydrofuran, in which the anhydrous tetrahydrofuran solution of the diphosphonic acid ester (19a) (corresponding to 0.55 mmols) obtained in Example 1 was dropped in an atmosphere of nitrogen in 15 minutes, followed by agitation at room temperature for 20 minutes.

Subsequently, an anhydrous tetrahydrofuran solution (20 ml) of 347 mg (1.10 mmols) of 4-[N-phenyl-(4-dimethylaminophenyl)amino]benzaldehyde ((27)-3) was further dropped in the mixture in 15 minutes, and agitated at room temperature for 1 hour. The reaction mixture was quenched with a small amount of ice, washed with a saturated saline solution and dried over anhydrous sodium sulfate.

The intended product was purified from the reaction mixture through silica gel chromatography (WAKO-gel c-300, tetrahydrofuran:hexane=1:8) and recrystallized from acetone/hexane to obtain 76 mg of the bis (aminostyryl) benzene compound ((16)-3). The yield was found to be at 19%, with a visible light absorption maximum being at 438 nm and a fluorescence maximum wavelength being at 600 nm.

EXAMPLE 5

<Synthetic example of bis(aminostyryl)benzene compound (structural formula (16)-4)>

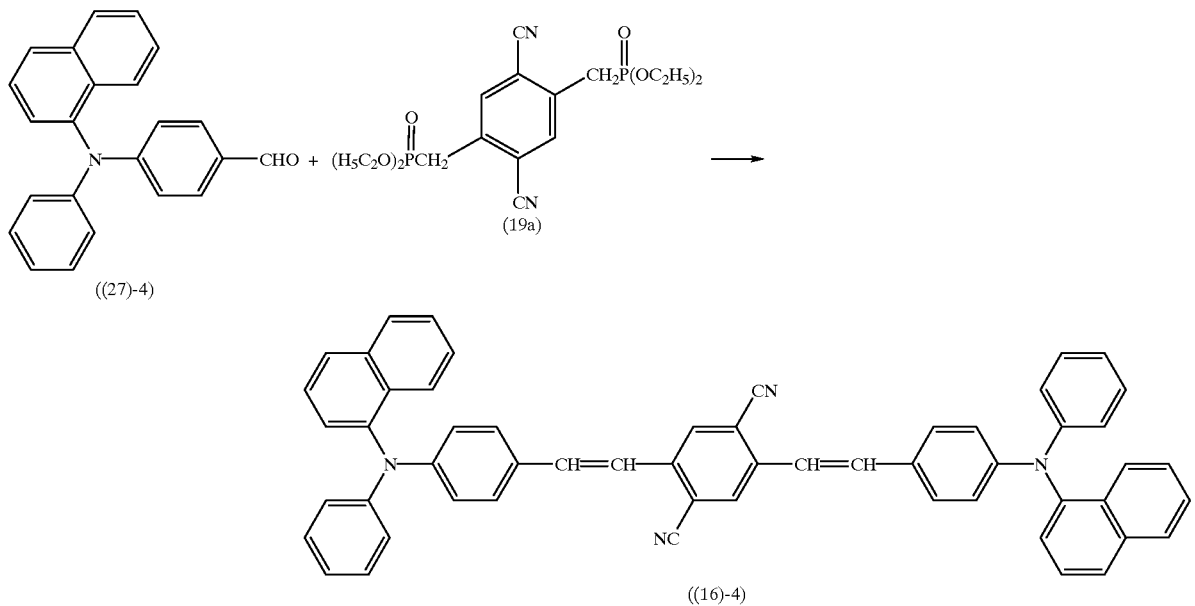

((27)-4) + (19a) → ((16)-4)

11.3 mmols of sodium hydride was suspended in 20 ml of anhydrous tetrahydrofuran, in which the anhydrous tetrahydrofuran solution of the diphosphonic acid ester (19a) (corresponding to 1.13 mmols) obtained in Example 1 was dropped in an atmosphere of nitrogen in 15 minutes, followed by agitation at room temperature for 20 minutes. Subsequently, an anhydrous tetrahydrofuran solution (12 ml) of 728 mg (2.25 mmols) of 4-[N-(1-naphthyl)-N-phenylamino]benzaldehyde ((27)-4) was further dropped in the mixture in 15 minutes, and agitated at room temperature for 2 hours. The reaction mixture was quenched with a small amount of ice, washed with a saturated saline solution and dried over anhydrous sodium sulfate.

Figure 3:
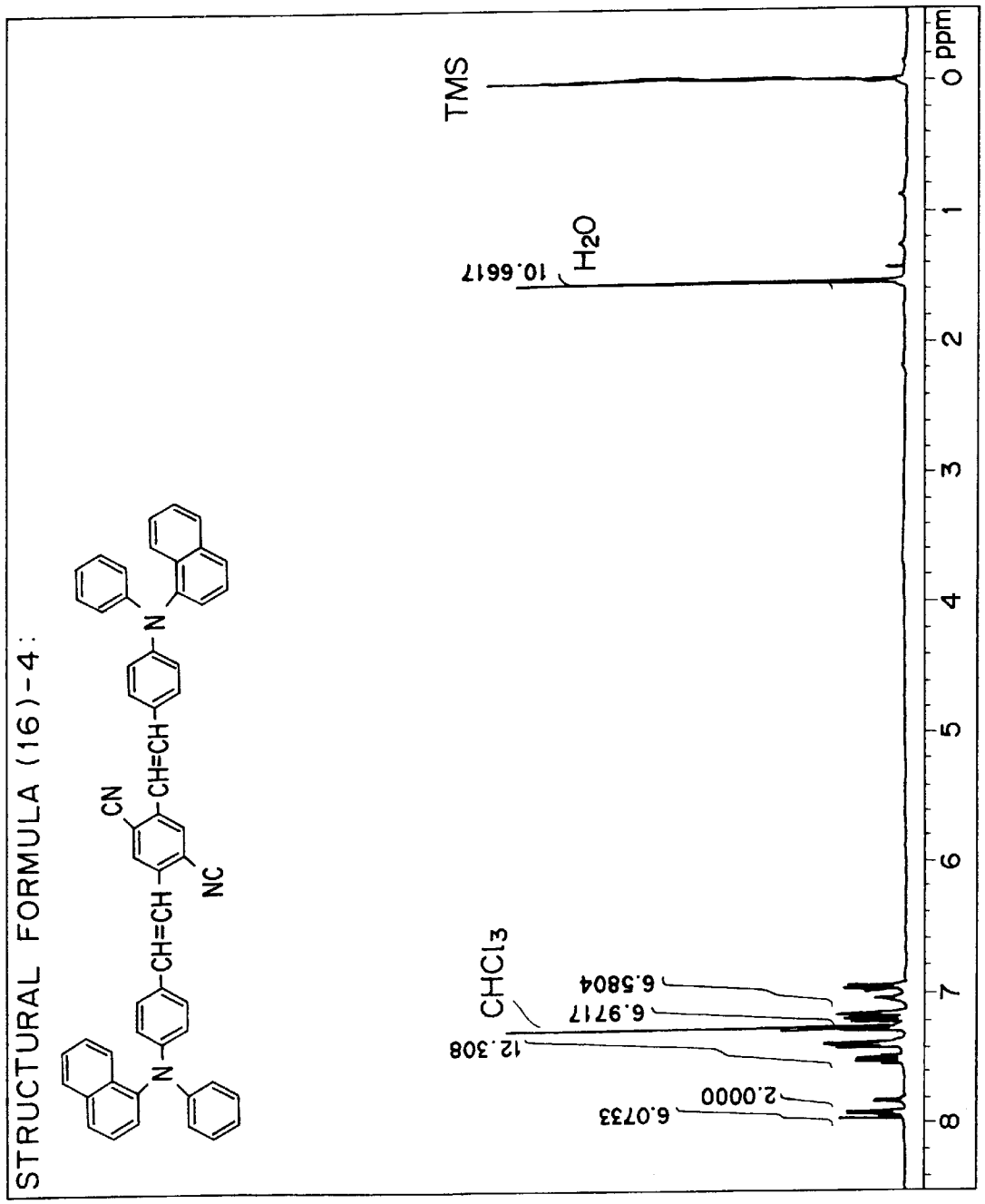
FIG. 3 is an $^1$HNMR spectral diagram of a bis (aminostyryl)benzene compound of structural formula (16)-4 of the invention.

The intended product was purified from the reaction mixture through silica gel chromatography (WAKO-gel C-300, tetrahydrofuran:hexane=1:8) and recrystallized from acetone/hexane to obtain 546 mg of the bis (aminostyryl) benzene compound ((16)-4). The yield was found to be at 63% with a glass transition point of 150° C. and a melting point of 210° C. The visible light absorption maximum of the tetrahydrofuran solution was at 461 nm and the fluorescence maximum wavelength was at 550 nm. The $^1$HNMR spectra of the solution were shown in FIG. 3 and also indicated below.

NMR (CDCl$_3$) δ (ppm): 6.97 (4H, d), 7.02 (2H, s), 7.25–7.49 (26H, m), 7.81 (2H, d), 7.92 (4H, d), 7.97 (2H, s)

EXAMPLE 6
<Synthetic example of bis(aminostyryl)benzene compound (structural formula (16)-5)>

EXAMPLE 7
<Synthetic example of 4-[N,N-di(4-methoxyphenyl)amino] benzaldehyde (structural formula (27)-2)>

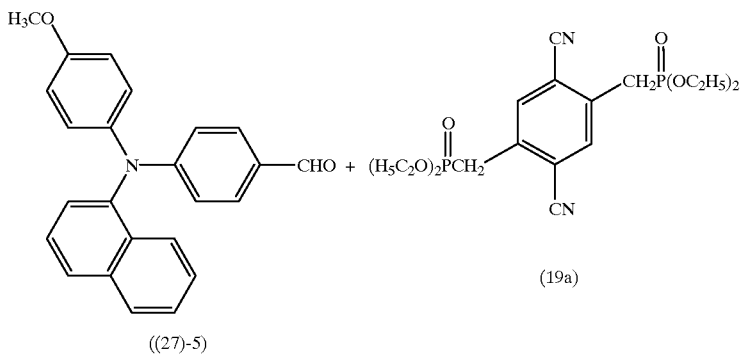

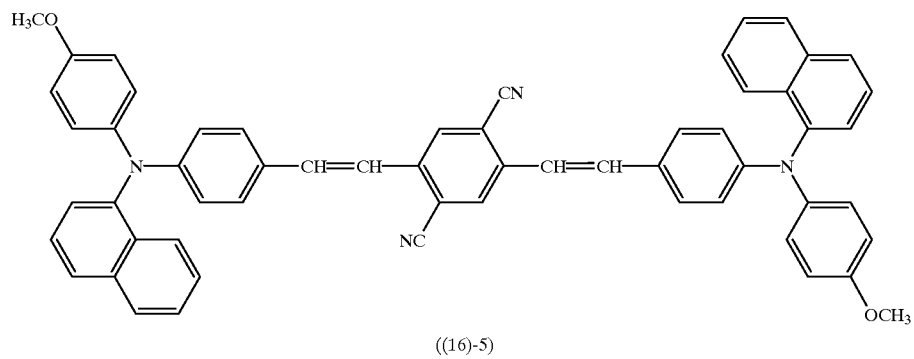

11.3 mmols of sodium hydride was suspended in 20 ml of anhydrous tetrahydrofuran, in which the anhydrous tetrahydrofuran solution of the diphosphonic acid ester (19a) (corresponding to 1.13 mmols) obtained in Example 1 was dropped in an atmosphere of nitrogen in 15 minutes, followed by agitation at room temperature for 20 minutes.

Subsequently, an anhydrous tetrahydrofuran solution (12 ml) of 761 mg (2.25 mmols) of 4-[N-(1-naphtyl)-N-(4-methoxyphenyl)amino]benzaldehyde ((27)-5) was further dropped in the mixture in 15 minutes, and agitated at room temperature for 2 hours. The reaction mixture was quenched with a small amount of ice, washed with a saturated saline solution and dried over anhydrous sodium sulfate.

The intended product was purified from the reaction mixture through silica gel chromatography (WAKO-gel C-300, tetrahydrofuran:hexane=1:8) and recrystallized from acetone/hexane to obtain 386 mg of the bis (aminostyryl) benzene compound ((16)-5). The yield was found to be at 43% with a glass transition point of 130° C. and a melting point of 190° C. The visible light absorption maximum was at 465 nm and the fluorescence maximum wavelength was at 555 nm.

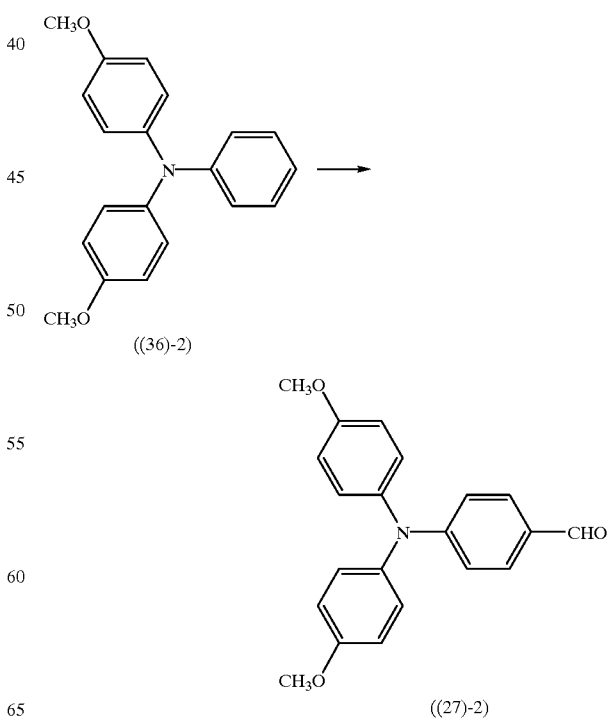

1.76 g (11.5 mmols) of phosphorus oxychloride was dropped in anhydrous dimethylformamide under agitation at room temperature, in which 25 ml of anhydrous dimethylformamide solution of 1.75 g of N,N-di(4-methoxyphenyl) aniline ((36)-2) was further dropped, following by raising the reaction temperature and agitating at 70° C. for 90 minutes.

The resultant solution was cooled down to room temperature and quenched with ice, followed by extraction of the reaction solution with toluene, washing with a saturated saline solution and drying over anhydrous sodium sulfate.

Figure 4:
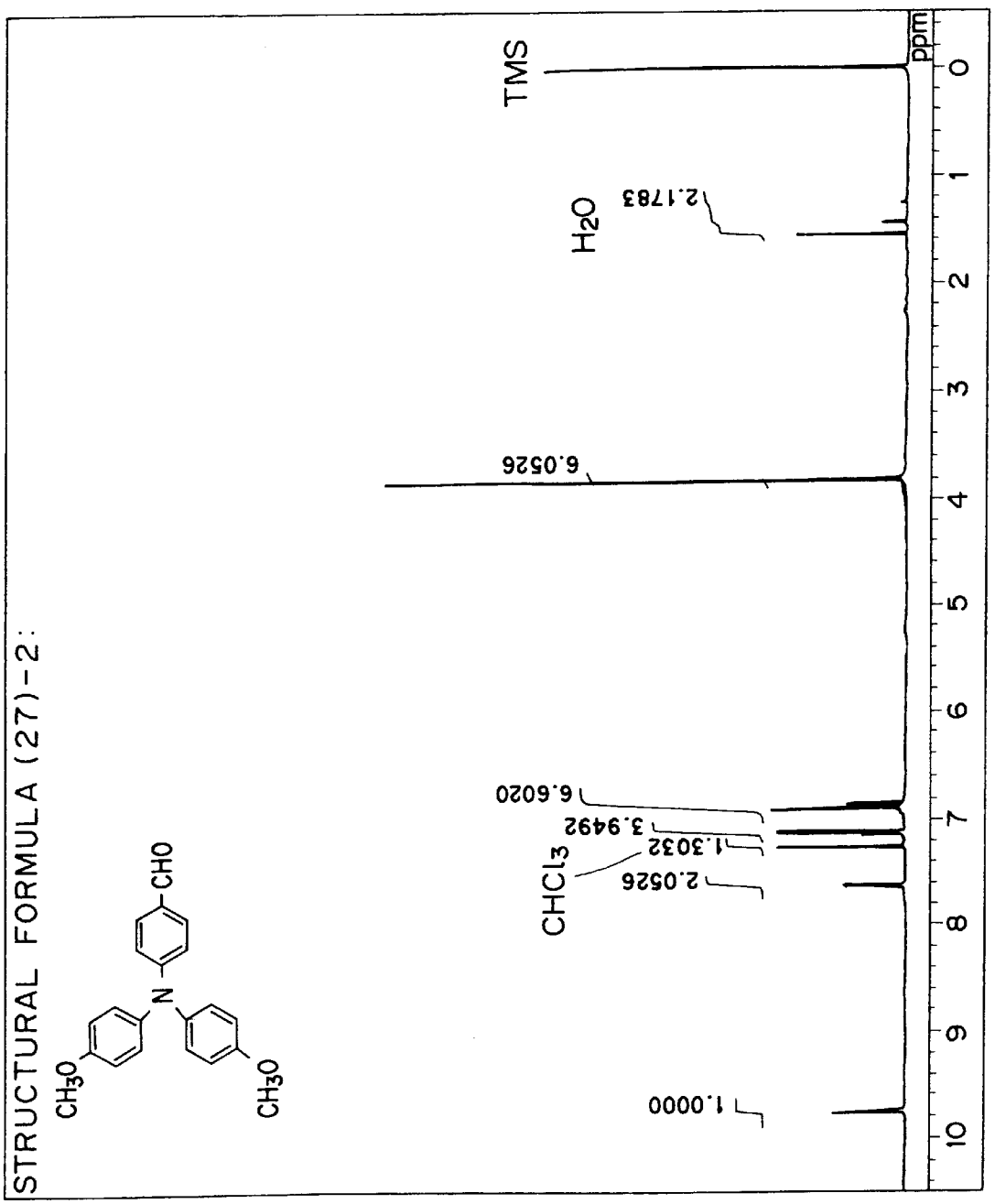
FIG. 4 is an $^1$HNMR spectral diagram of 4-[N,N-di(4-methoxyphenyl)amino]benzaldehyde of structural formula (27)-2 which is a synthetic intermediate of the invention.

The intended product was purified from the reaction mixture through silica gel chromatography (WAKO-gel C-300, tetrahydrofuran:hexane=1:4) to obtain 0.750 g of the compound ((27)-2). The yield was found to be at 39%. The $^1$HNMR spectra of the compound were shown in FIG. 4 and also indicated below.

NMR (CDCl$_3$) δ (ppm): 3.81 (6H, s), 6.82 (2H, d), 6.90 (4H, d), 7.13 (4H, d), 7.62 (2H, d), 9.78 (1H, s)

EXAMPLE 8
<Synthetic example of N,N-di(4-methoxyphenyl)aniline (structural formula (36)-2)>

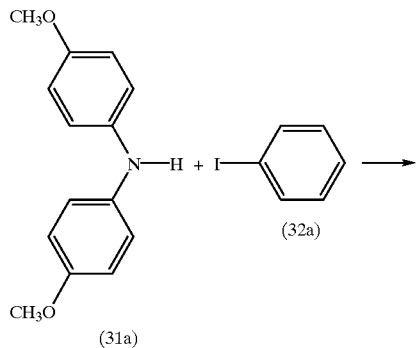

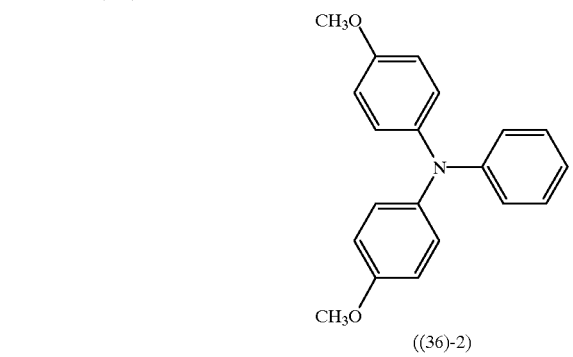

1.00 g (4.46 mmols) of N,N-di(4-methoxyphenyl)amine (31a), 1.00 g (4.90 mmols) of iodobenzene (32a), 0.502 g (5.23 mmols) of t-BuONa and 0.010 g (0.044 mmols) of Pd(CH$_3$COO)$_2$ were dissolved in anhydrous xylene, and while refluxing the solution in an atmosphere of nitrogen, 1.0 ml of 0.237 M of P(Bu$^t$)$_3$ was further dropped, followed by refluxing for 4 hours.

Figure 5:
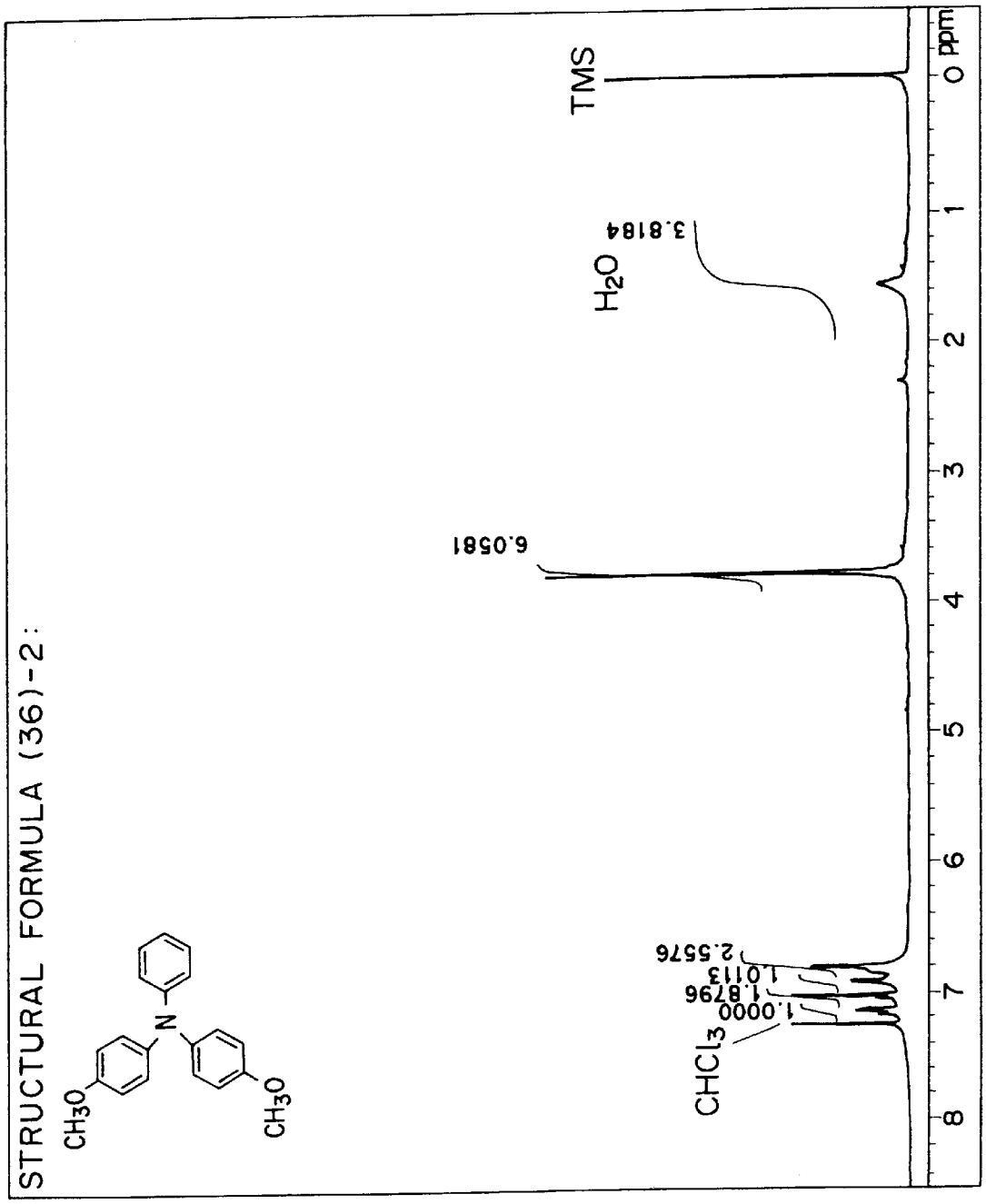
FIG. 5 is an $^1$HNMR spectral diagram of N-di(4-methoxyphenyl)aniline of structural formula (36)-2 which is a synthetic intermediate of the invention.

The resultant reaction product was purified through silica gel chromatography (WAKO-gel C-300, tetrahydrofuran:hexane=1:4), and the resulting eluate was recrystallized from acetone/hexane to obtain a compound ((36)-2). The yield was 1.17 g (yield of 88%). The $^1$HNMR spectra of the compound were shown in FIG. 5 and also indicated below.

NMR (CDCl$_3$) δ (ppm): 3.80 (6H, s), 6.80 (4H, d), 6.82 (1H, t), 6.92 (2H, d), 7.02 (4H, d), 7.17 (2H, t)

EXAMPLE 9
<Synthetic example of N-(1-phenyl)-N-(4-ethoxyphenyl) aniline (structural formula (36)-1)>

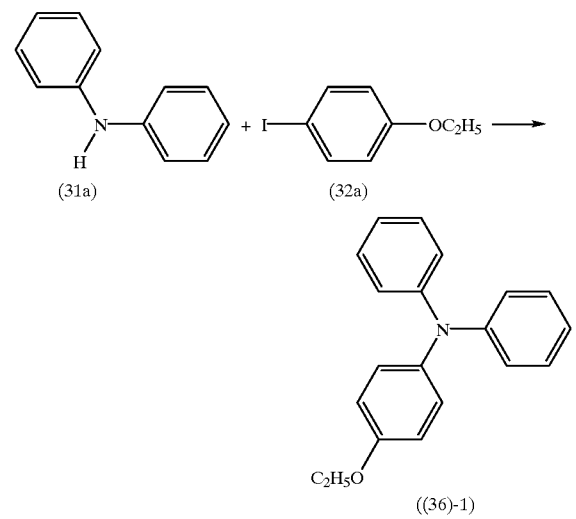

8.20 g (50 mmols) of N,N-di-phenylamine (31a), 12.40 g (50 mmols) of iodoanisole (32a), 5.76 g (60 mmols) of t-BuONa and 0.224 g (1.00 mmol) of Pd(CH$_3$COO)$_2$ were dissolved in dichlorobenzene, and while refluxing the resulting solution in an atmosphere of nitrogen, 17 ml of 0.237 M of P(Bu$^t$)$_3$ was further dropped, followed by refluxing for 4 hours.

Figure 6:
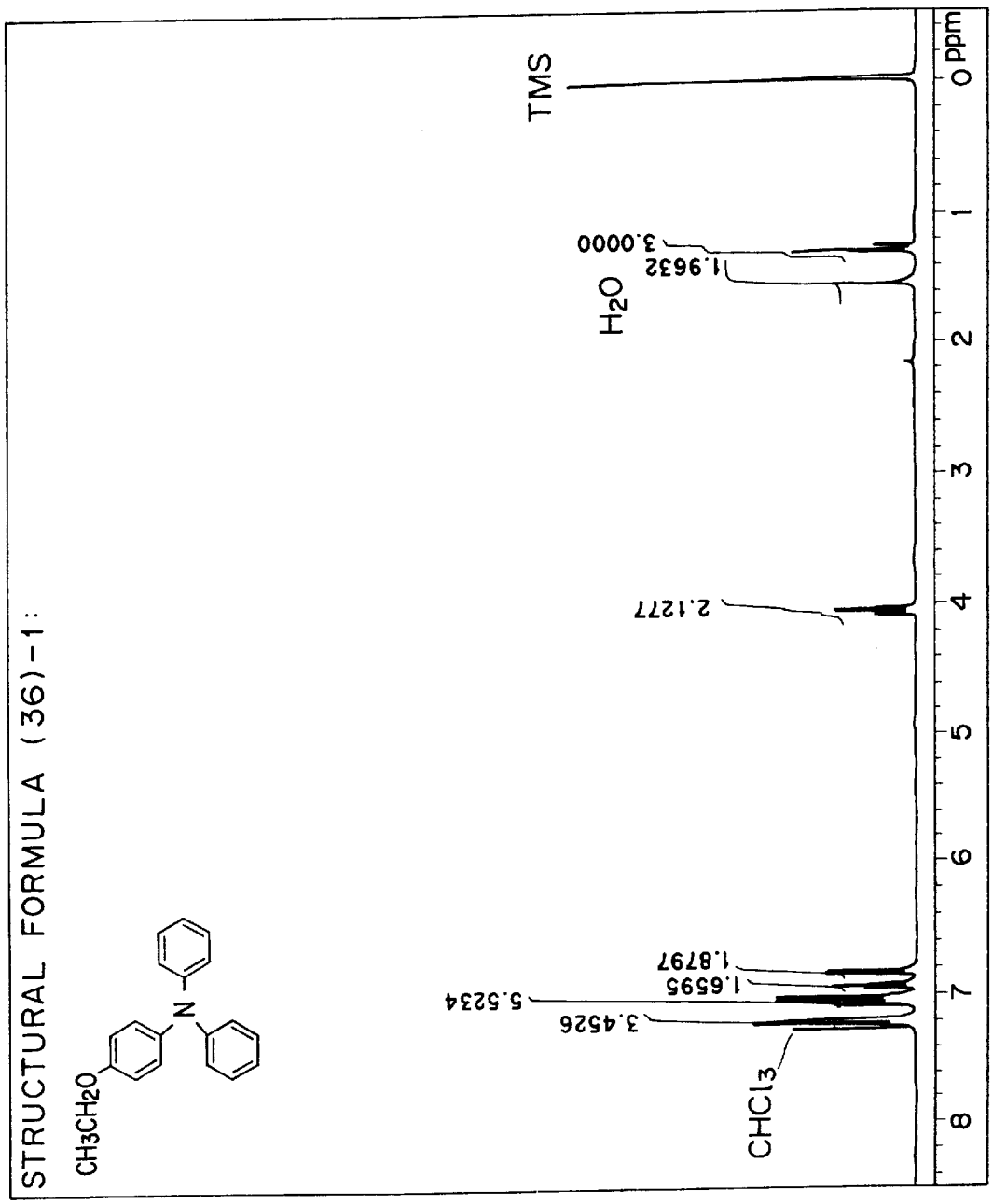
FIG. 6 is an $^1$HNMR spectral diagram of N-(1-phenyl)-N-(4-ethoxyphenyl)aniline of structural formula (36)-1 which is a synthetic intermediate of the invention.

The intended product was obtained by purification through column chromatography (alumina, hexane:toluene= 4:1) and recrystallization of the resultant eluate from acetone/hexane. The yield was 10.9 g (yield of 79%). The $^1$HNMR spectra of the compound were shown in FIG. 6 and also indicated below.

NMR (CDCl$_3$) δ (ppm): 2.28 (3H, t), 4.02 (2H, q), 6.84 (2H, d), 6.94 (2H, t), 7.03 (4H, d), 7.06 (2H, d), 7.20 (4H, t)

EXAMPLE 10
<Synthetic example of 2,5-di(bromotriphenylphosphomethyl)terephthalonitrile (structural formula (20a))>

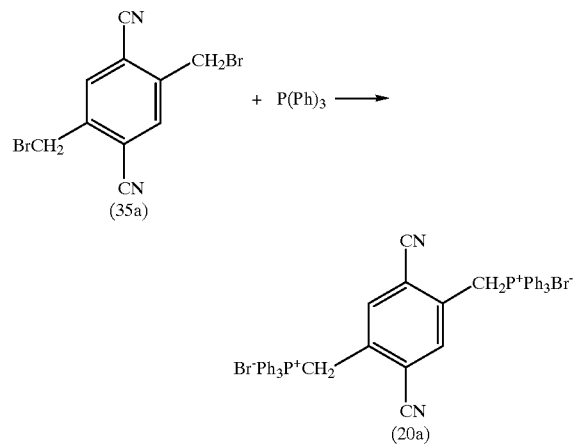

750 mg (2.39 mmols) of 2,5-di(bromomethyl) terephthalonitrile (35a) and 1.38 g (5.26 mmols) of triphenylphosphine were dissolved in xylene and refluxed for 20 hours. The reaction solution was cooled down to room temperature, and the resultant precipitate was separated by filtration, washed with 5 ml of xylene, dried under reduced pressure and dissolved for storage in 25 ml of anhydrous tetrahydrofuran. In this way, there was obtained the diphosphonium (20a) set out in Example 2.

EXAMPLE 11

<Synthetic example of 2,5-di(bromomethyl) terephthalonitrile (structural formula (35a))>

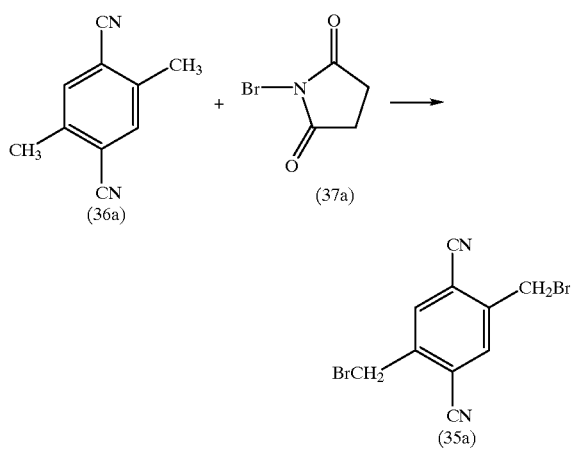

1.00 g (6.4 mmols) of 2,5-dimethylterephthalonitrile and 8.10 g (90 mmols) of N-bromosuccinimide (NBS)(37a) were dissolved in 500 ml of chloroform and refluxed for 48 hours while irradiating a high pressure mercury lamp (400 W).

Figure 7:
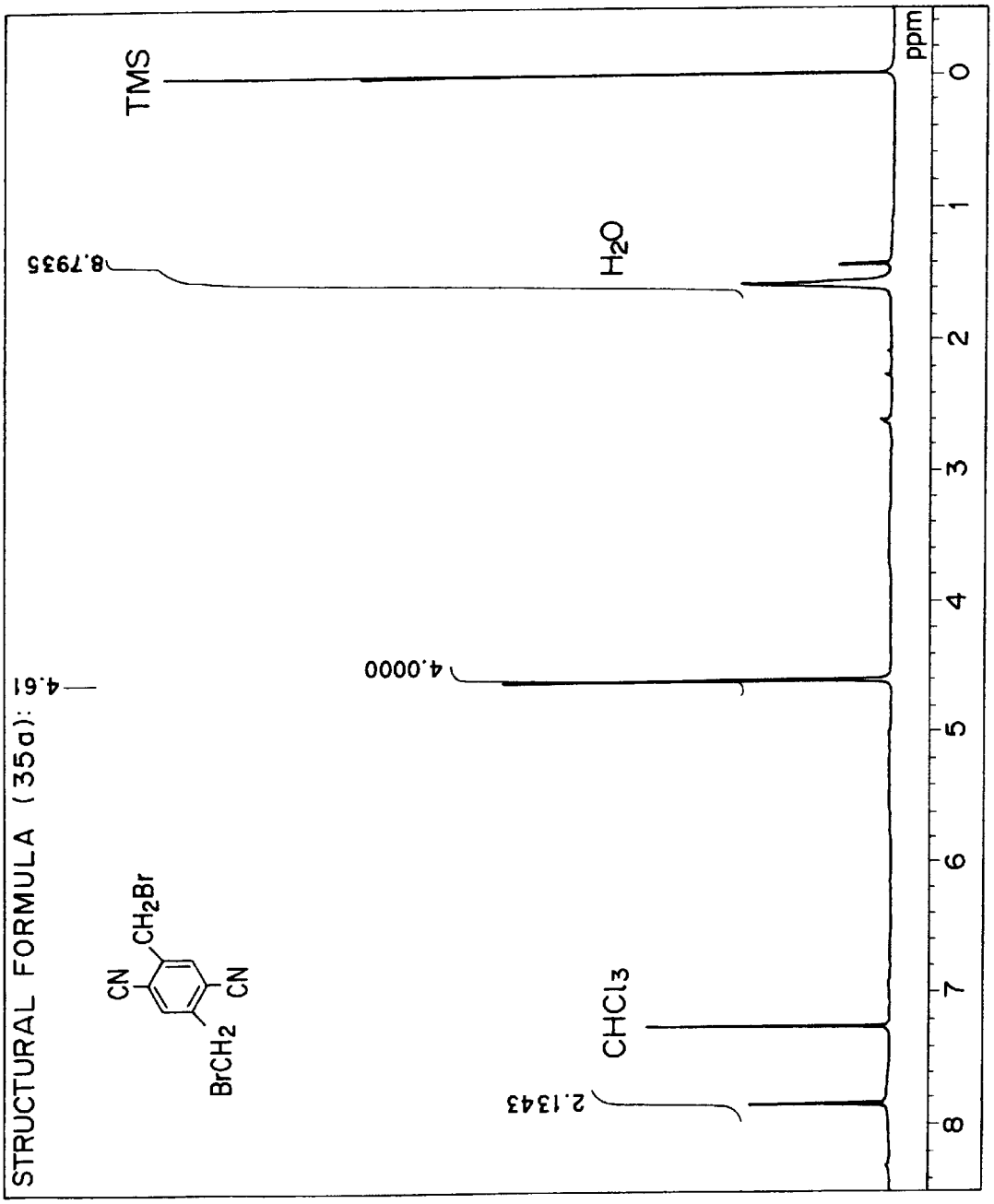
FIG. 7 is an $^1$HNMR spectral diagram of 2,5-di (bromomethyl)terephthalonitrile of structural formula (35a) which is a synthetic intermediate of the invention.

The solvent was distilled off, and the resultant reaction product was purified through silica gel chromatography (WAKO-gel C-300, tetrahydrofuran:hexane=1:4), and the resultant eluate was recrystallized twice from acetone/hexane to selectively obtain a compound (35a) in the form of white crystals. The yield was 698 g (yield of 34%). The $^1$HNMR spectra of the compound were shown in FIG. 7 and also indicated below.

NMR (CDCl$_3$) δ (ppm): 4.60 (4H, s), 7.83 (2H, s)

EXAMPLE 12

<Synthetic example of N-(p-toluyl)-N,N-diphenylamine) (structural formula (36)-6)>

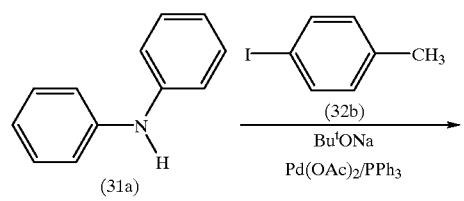

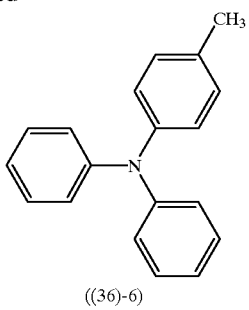

((36)-6)

9.70 g (57.3 mmols) of N,N-diphenylamine (31a), 12.5 g (57.3 mmols) of 4-iodotoluene (32b), 6.61 g (68.8 mmols) of t-BuONa, 260 mg (1.15 mmols) of Pd(CH$_3$COO)$_2$ and 1.20 g (4.58 mmols) of triphenylphosphine were dissolved in xylene and refluxed in an atmosphere of nitrogen for 4 hours.

Figure 8:
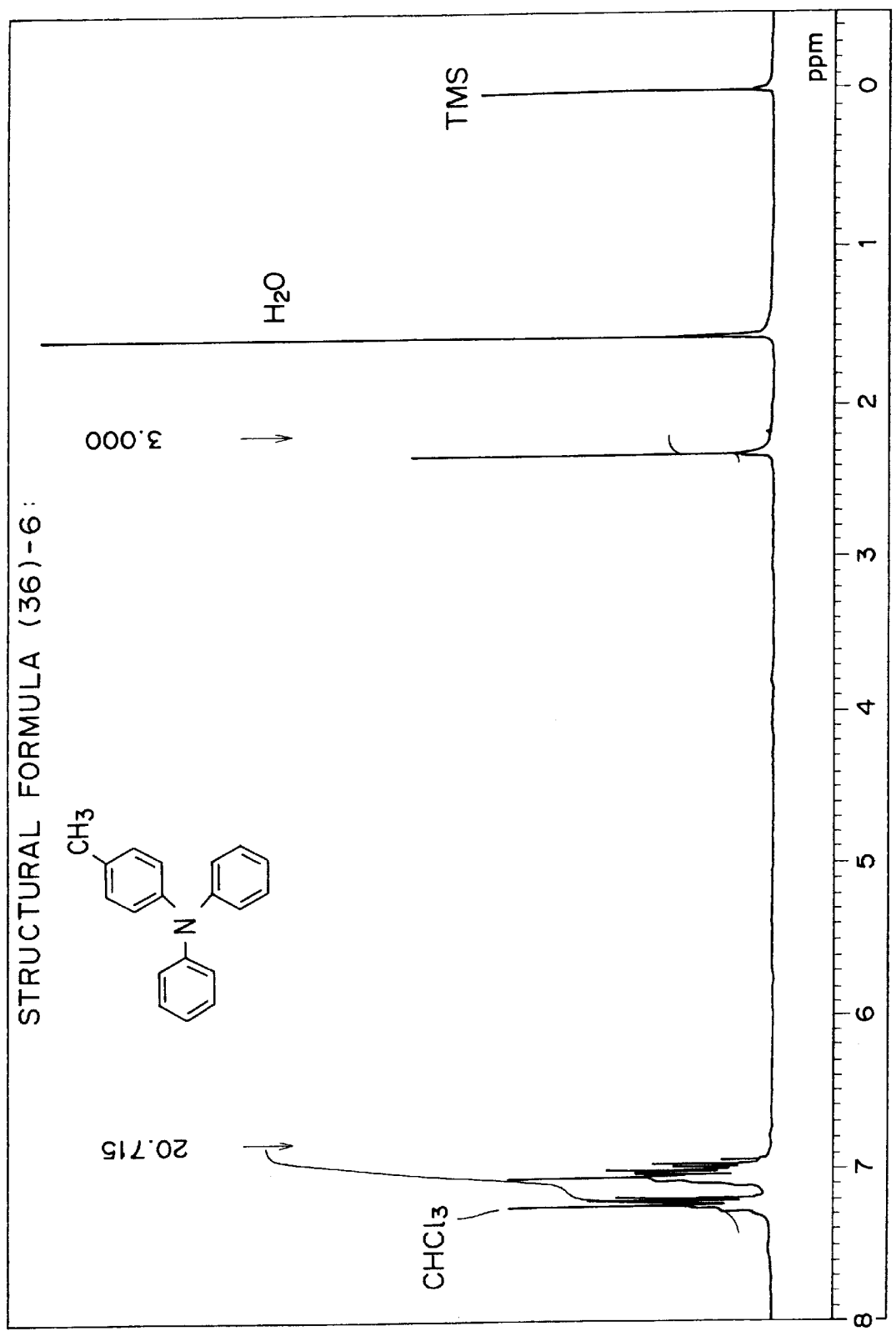
FIG. 8 is an $^1$HNMR spectral diagram of N-(p-toluyl)-N, N-diphenylamine of structural formula (36)-6 which is a synthetic intermediate of the invention.

The resultant insoluble matter was separated by filtration and purified through alumina chromatography (300 mesh-sized neutral alumina, tetrahydrofuran:hexane=1:4), and the resulting eluate was recrystallized from acetone/hexane to quantitatively obtain a compound ((36)-6). The $^1$HNMR spectra of this product ((36)-6) were shown in FIG. 8 and also indicated below.

NMR (CDCl$_3$) δ (ppm): 2.31 (3H, s), 6.94–7.27 (14H, m)

EXAMPLE 13

<Synthetic example of 4-[N-(p-toluyl)-N-phenylamino] benzaldehyde (structural formula (27)-6)>

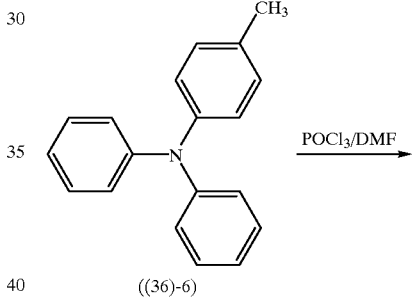

((36)-6)

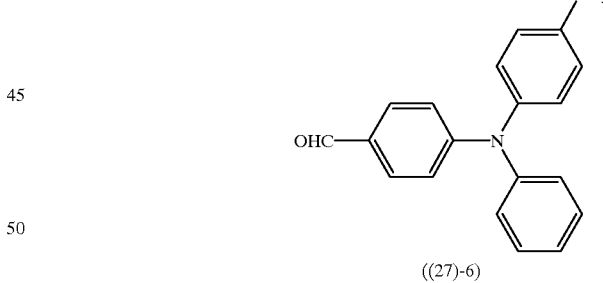

((27)-6)

5.96 g (38.9 mmols) of phosphorus oxychloride was dropped in 50 ml of anhydrous dimethylformamide (DMF) under agitation at room temperature, in which 50 ml of anhydrous dimethylformamide (DMF) solution of 5.04 g (19.4 mmols) of N-(p-toluyl)-N,N-diphenylamine ((36)-6) was further dropped, following by raising the reaction temperature and agitating at 70° C. for 90 minutes.

Figure 9:
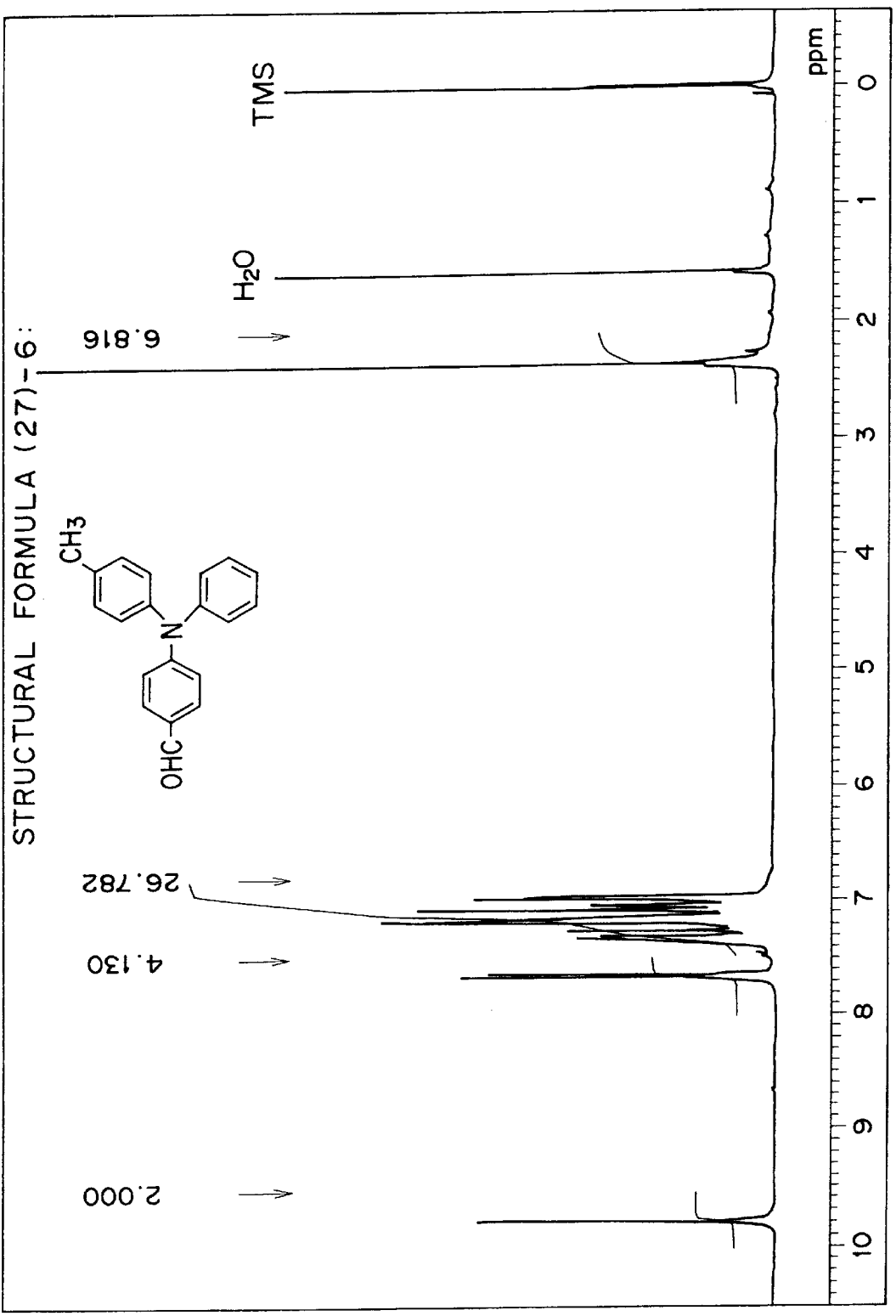
FIG. 9 is an $^1$HNMR spectral diagram of 4-[N-(p-toluyl)-N-diphenylamino]benzaldehyde of structural formula (27)-6 which is a synthetic intermediate of the invention.

The resultant solution was cooled down to room temperature and quenched with a small amount of ice, followed by purification through silica gel chromatography (WAKO-gel C-300, tetrahydrofuran:hexane=1:4) to obtain an oily substance ((27)-6) substantially quantitatively. The $^1$HNMR spectra of this product were shown in FIG. 9 and also indicated below.

NMR (CDCl$_3$) δ (ppm): 2.35 (3H, s), 6.96–7.64 (11H, m), 7.66 (2H, d), 9.80 (1H, s)

EXAMPLE 14

<Synthetic example of bis(aminostyryl)benzene compound (structural formula (16)-6)>

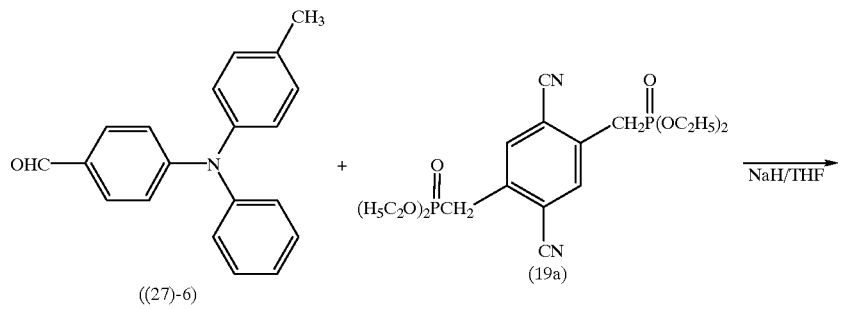

14.5 mmols of sodium hydride was suspended in 20 ml of anhydrous tetrahydrofuran, in which the anhydrous tetrahydrofuran solution of diphosphonic acid ester (19a) (corresponding to 2.33 mmols) was dropped in an atmosphere of nitrogen, followed by agitation for 60 minutes. Subsequently, an anhydrous tetrahydrofuran solution (40 ml) of 1.34 g (4.66 mmols) of 4-[N-(p-toluyl)-N-phenylamino]benzaldehyde ((27)-6) was further dropped in the mixture in 15 minutes, and agitated at room temperature for 12 hours.

Figure 10:
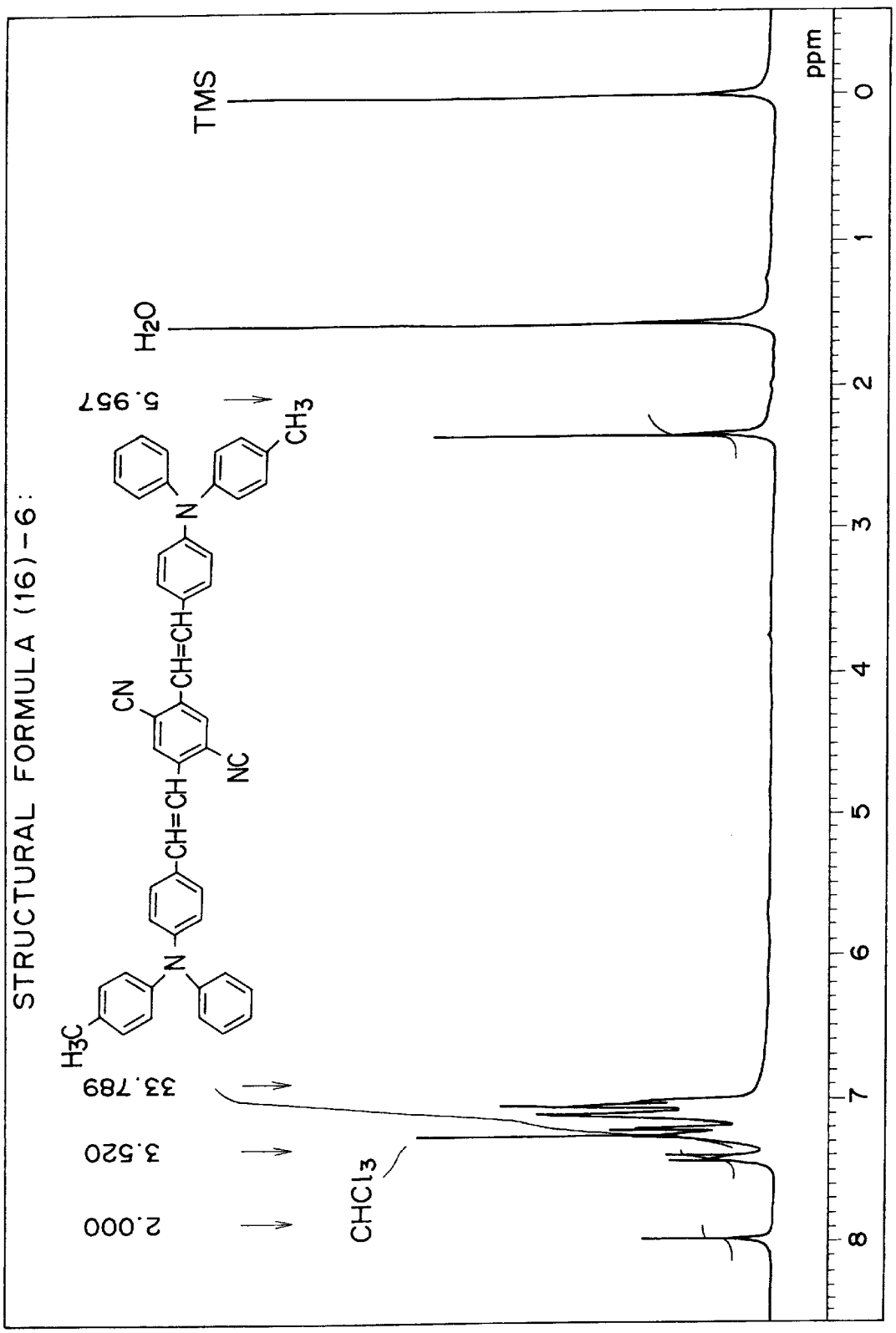
FIG. 10 is an $^1$HNMR spectral diagram of a bis (aminostyryl)benzene compound of structural formula (16)-6 of the invention.

The reaction mixture was quenched with a small amount of ice, washed with a saturated saline solution and dried over anhydrous sodium sulfate. 0.787 g of the bis(aminostyryl) benzene compound ((16)-6) was obtained by purification through silica gel chromatography (WAKO-gel C-300, tetrahydrofuran:hexane=1:4→1:1) and recrystallization from acetone/hexane. The yield was found to be at 49%, and the $^1$HNMR spectra of the solution were shown in FIG. 10 and indicated below.

NMR (CDCl$_3$) δ (ppm): 2.34 (6H, s), 7.01–7.30 (26H, m), 7.42 (4H, d), 7.99 (2H, s)

The visible light absorption maximum of a tetrahydrofuran solution of this substance ((16)-6) was at 469 nm and the fluorescent maximum wavelength was at 568 nm.

EXAMPLE 15

<Synthetic example of N,N-di(p-toluyl-N-phenylamine (structural formula (36)-7)>

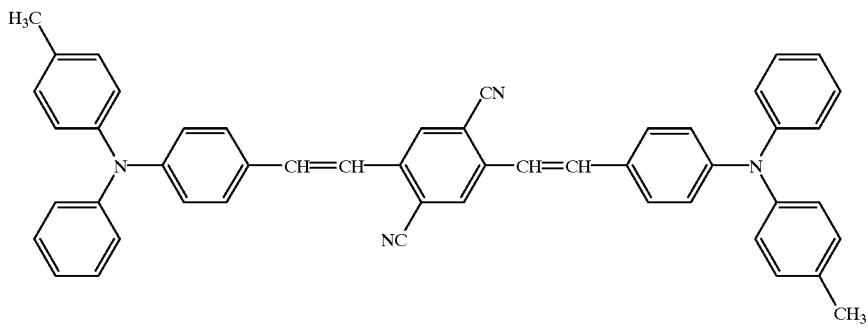

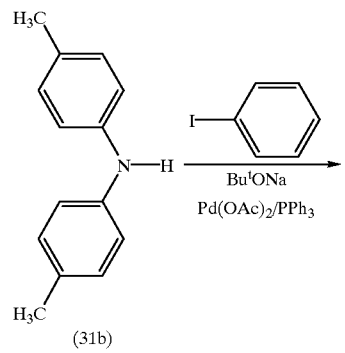

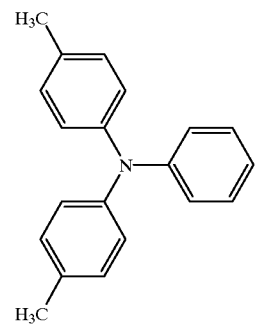

10.0 g (50.7 mmols) of N,N-di(p-toluyl)amine (31b), 10.3 g (50.7 mmols) of 4-iodobenzene, 5.85 g (60.8 mmols) of t-BuONa, 300 mg (1.34 mmols) of Pd(CH$_3$COO)$_2$ and 1.50 g (5.71 mmols) of triphenylphosphine were dissolved in 500 ml of xylene and refluxed in an atmosphere of nitrogen for 4 hours.

Figure 11:
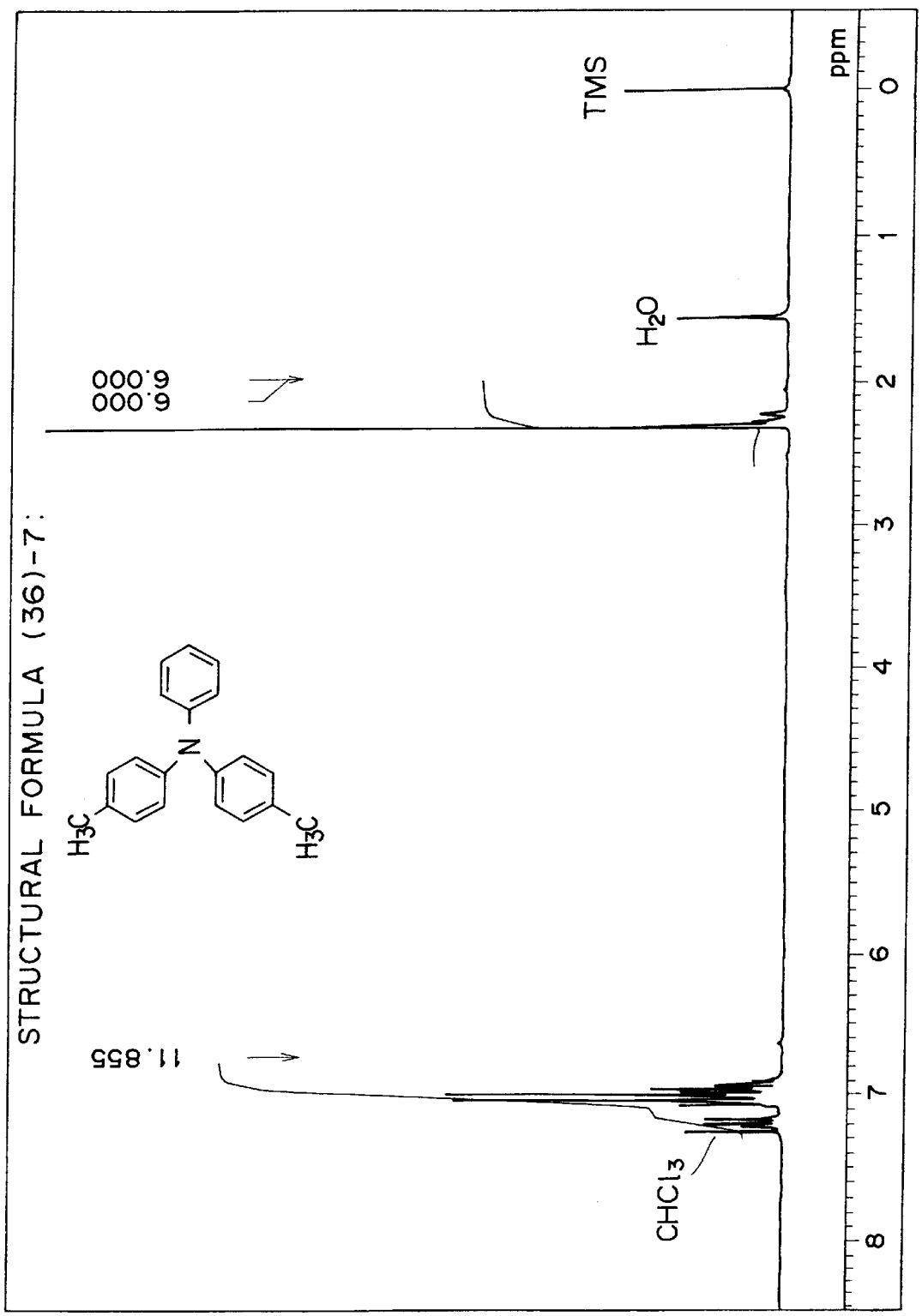
FIG. 11 is an $^1$HNMR spectral diagram of N,N-(p-toluyl-N-phenylamine) of structural formula (36)-7 which is a synthetic intermediate of the invention.

The resultant insoluble matter was separated by filtration and purified through alumina chromatography (300 mesh-sized neutral alumina, tetrahydrofuran:hexane=1:4), and the resulting eluate was recrystallized from acetone/hexane to quantitatively obtain the intended compound ((36)-7). The $^1$HNMR spectra of this product were shown in FIG. 11 and also indicated below.

NMR (CDCl$_3$) δ (ppm): 2.30 (6H, s), 6.90–7.07 (11H, m), 7.16–7.22 (2H, m)

EXAMPLE 16

<Synthetic example of 4-[N,N-di(p-toluyl) amino] benzaldehyde (structural formula (27)-7)>

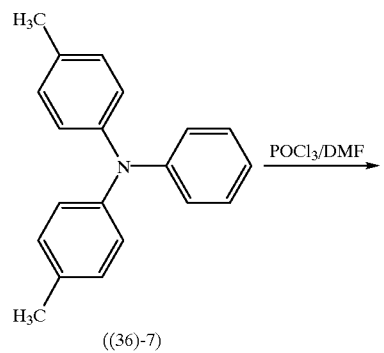

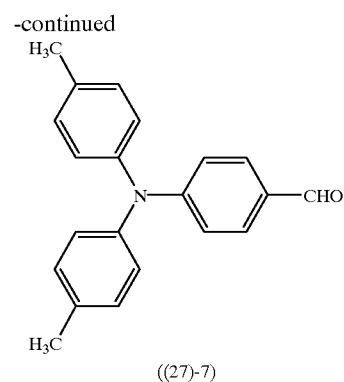

5.90 g (38.4 mmols) of phosphorus oxychloride was dropped in 20 ml of anhydrous dimethylformamide (DMF) under agitation at room temperature, in which 50 ml of anhydrous dimethylformamide solution of 7.00 g (25.6 mmols) of N,N-di(p-toluyl)-N-phenylamine ((36)-7) was further dropped, following by agitation at room temperature for 90 minutes.

Figure 12:
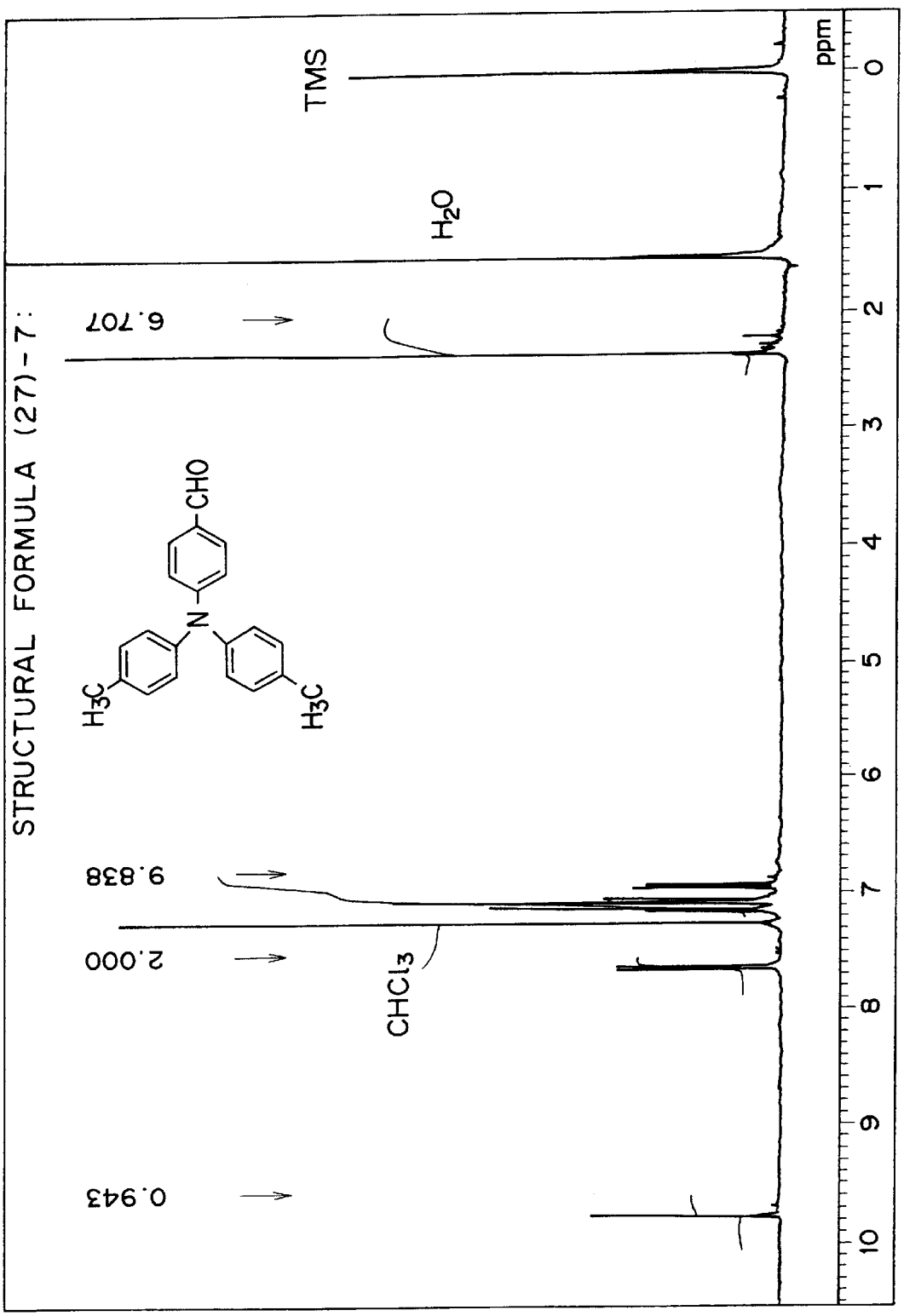
FIG. 12 is an $^1$HNMR spectral diagram of 4-[N,N-di(p-toluyl)amino]benzaldehyde of structural formula (27)-7 which is a synthetic intermediate of the invention.

The resultant reaction mixture was quenched with a small amount of ice, extracted with toluene, washed with a saturated saline solution and dried over Na$_2$SO$_4$, followed by purification through silica gel chromatography (WAKO-gel C-300, tetrahydrofuran:hexane=1:4) to obtain an oily substance ((27)-7) substantially quantitatively. The $^1$HNMR spectra of this product were shown in FIG. 12 and also indicated below.

NMR (CDCl$_3$) δ (ppm): 2.35 (6H, s), 6.93 (2H, d), 7.06 (4H, d), 7,15 (4H, d), 7.64 (4H, d), 9.78 (1H, s)

EXAMPLE 17

<Synthetic example of bis(aminostyryl)benzene compound (structural formula (16)-7)>

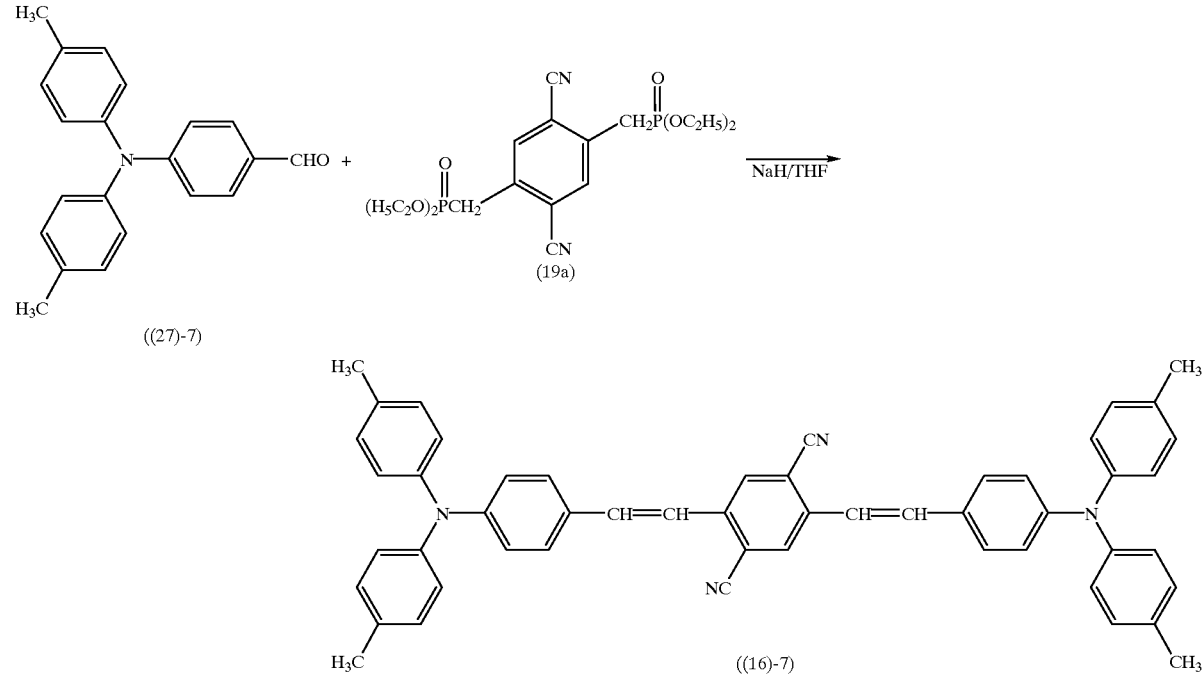

14.3 mmols of sodium hydride was suspended in 20 ml of anhydrous tetrahydrofuran (THF), in which 20 ml of an anhydrous tetrahydrofuran solution of diphosphonic acid ester (19a) (corresponding to 2.39 mmols) was dropped in an atmosphere of nitrogen, followed by further dropping of 25 ml of an anhydrous tetrahydrofuran solution of 4-[N,N-di (p-toluyl)amino]benzaldehyde ((27)-7) (corresponding to 2.39 mmols) and agitation for 48 hours.

Figure 13:
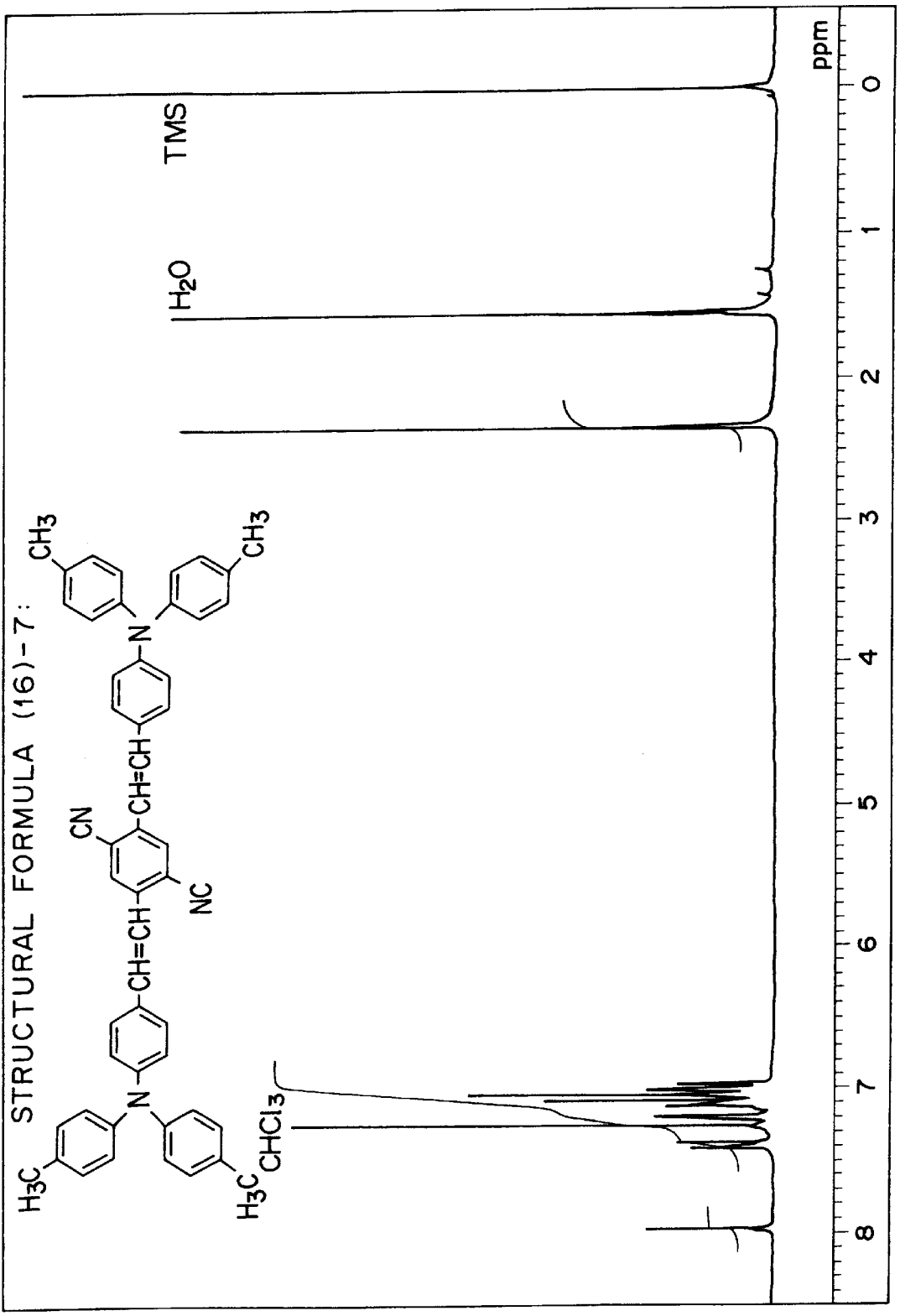
FIG. 13 is an $^1$HNMR spectral diagram of a bis (aminostyryl)benzene compound of structural formula (16)-7 of the invention.

The reaction mixture was quenched with a small amount of ice, washed with a saturated saline solution and dried over anhydrous sodium sulfate. 431 mg of the bis(aminostyryl) benzene compound ((16)-7) was obtained by purification through silica gel chromatography (WAKO-gel C-300, tetrahydrofuran:hexane=1:4→1:1) and recrystallization from acetone/hexane. The yield was found to be at 25%, and the $^1$HNMR spectra of the solution were shown in FIG. 13 and indicated below.

NMR (CDCl$_3$) δ (ppm): 2.33 (6H, s), 6.97–7.21 (24H, m), 7.39 (4H, d), 7.97 (2H, s)

The visible light absorption maximum of a tetrahydrofuran solution of this substance ((16)-7) was at 476 nm and the fluorescent maximum wavelength was at 590 nm.

EXAMPLE 18

This example illustrates fabrication of an organic electroluminescent device having a single hetero structure using, as a hole transport luminescent material, a compound of the following structural formula (16)-1, which is a compound of the general formula (I) wherein $R^1$ and $R^4$ independently represent a 3-ethoxyphenyl group, and $R^6$ and $R^8$ independently represent a cyano group:

Structural formula (16)-1:

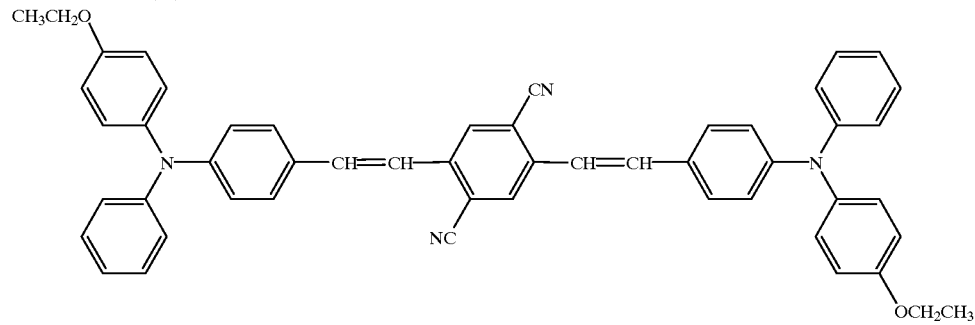

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. The compound of the above structural formula (16)-1 was subjected to vacuum deposition at a vacuum of 10$^{-4}$ Pa or below to form, for example, a 50 nm thick hole transport layer (serving also as a luminescent layer). The deposition rate was at 0.1 nm/second.

Further, Alq$_3$ (tris(8-quinolinol)aluminium) of the following structural formula was provided as an electron transport material and was deposited in contact with the hole transport layer. The electron transport layer made of Alq$_3$ was set at a thickness, for example, of 50 nm, and the deposition rate was at 0.2 nm/second.

Alq$_3$:

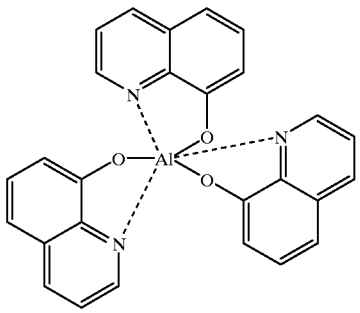

A built-up film of Mg and Ag provided as a cathode material was used. To this end, Mg and Ag were, respectively, vacuum deposited at a deposition rate of 1 nm/second to form, for example, a 50 nm thick Mg film and a 150 nm thick Ag film. In this way, an organic electroluminescent device as shown in FIG. 34 was fabricated in Example 18.

Figure 16:
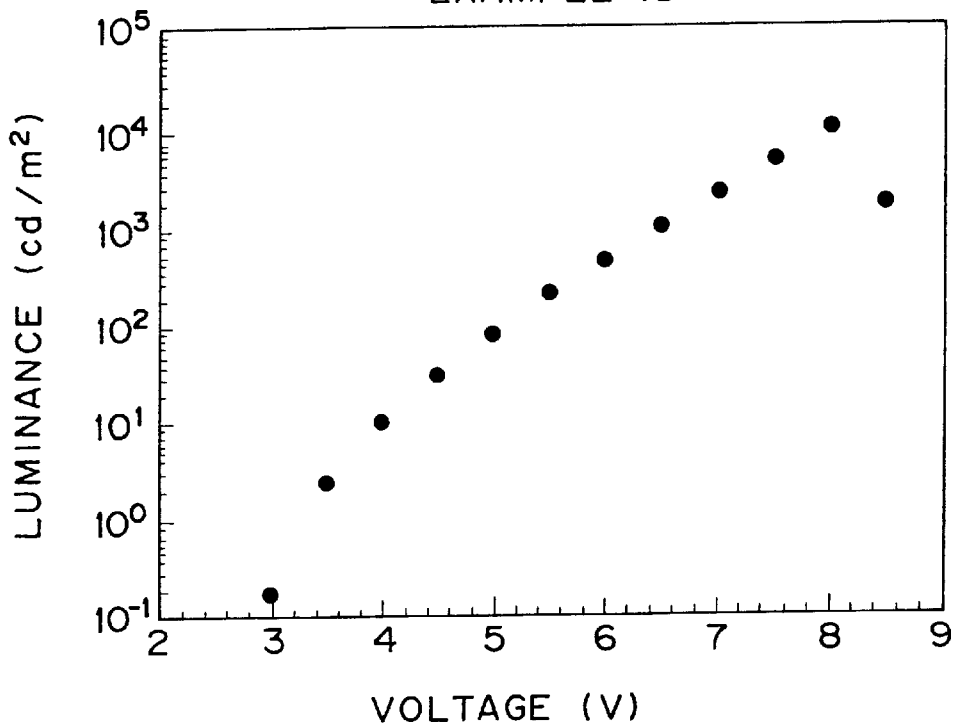
FIG. 16 is a graph showing a voltage-luminance characteristic of the organic electroluminescent device of Example 18 of the invention.

Luminescent characteristics of the device were evaluated by applying a forward bias DC voltage to the thus fabricated organic electroluminescent device of Example 18 in an atmosphere of nitrogen. The luminescent color was red, and the device was then subjected to spectral measurement, with the result that, as shown in FIG. 14, spectra having a luminescent peak at 620 nm were obtained. The spectral measurement was performed by use of a spectroscope made by Otuska Electronic Co., Ltd. and using a photodiode array as a detector. Moreover, when the device was subjected to voltage-luminance measurement, there could be obtained a luminance of 10,000 cd/m$^2$ at 8 V as is particularly shown in FIG. 16.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 4,000 hours before the luminance was reduced to half.

This example illustrates fabrication of an organic electroluminescent device having a single hetero structure using, as an electron transport luminescent material, a compound of the structural formula (16)-1, which is a compound of the general formula (I) wherein $R^1$ and $R^4$ independently represent a 3-ethyoxyphenyl group, and $R^6$ and $R^8$ independently represent a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. α-NPD (α-naphthylphenyldiamine) of the following structural formula was subjected to vacuum deposition at a vacuum of $10^{-4}$ Pa or below to form, for example, a 50 nm thick hole transport layer. The deposition rate was at 0.1 nm/second.

a-NPD:

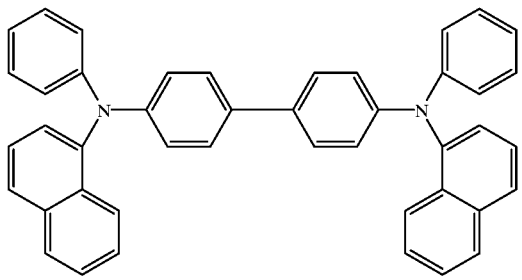

Further, the compound of the structural formula (16)-1 used as an electron transport material was vacuum deposited in contact with the hole transport layer. The thickness of the electron transport layer (serving also as a luminescent layer) composed of the compound of the structural formula (16)-1 was set, for example, at 50 nm, and the deposition rate was at 0.2 nm/second.

A built-up film of Mg and Ag provided as a cathode material was used. More particularly, Mg and Ag were, respectively, vacuum deposited at a deposition rate of 1 nm/second to form, for example, a 50 nm thick Mg film and a 150 nm thick Ag film. In this way, an organic electroluminescent device of Example 19 as shown in FIG. 34 was fabricated.

Figure 17:
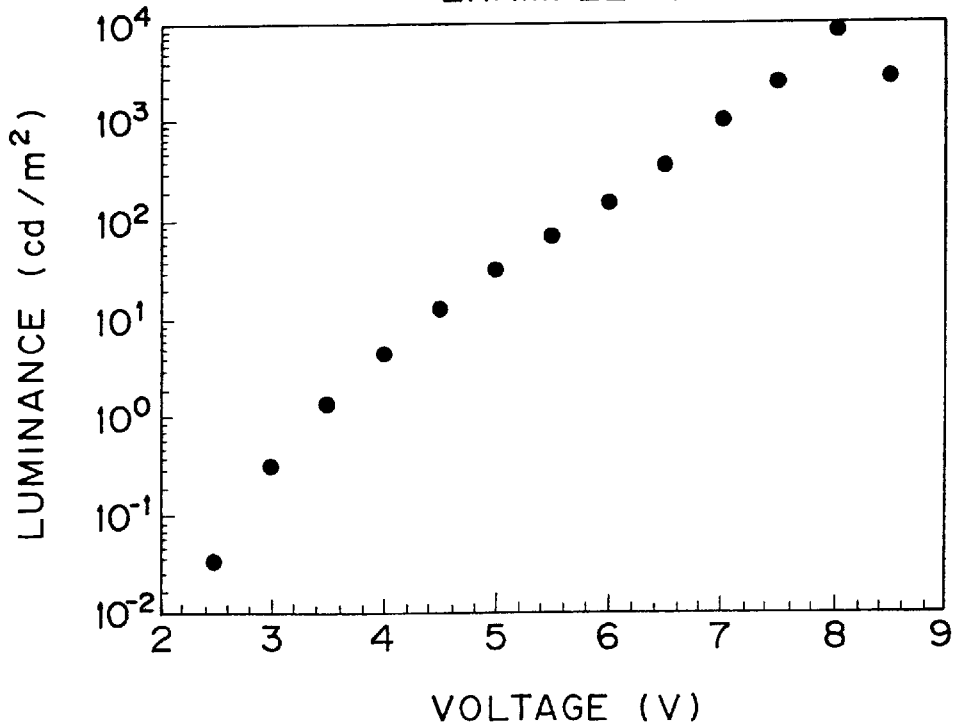
FIG. 17 is a graph showing a voltage-luminance characteristic of the organic electroluminescent device of Example 19 of the invention.

Luminescent characteristics were evaluated by applying a forward bias DC voltage to the thus fabricated organic electroluminescent device of Example 19 in an atmosphere of nitrogen. The luminescent color was red, and the device was then subjected to spectral measurement as in Example 18, with the result that, as shown in FIG. 15, spectra having a luminescent peak at 620 nm were obtained. Moreover, when the device was subjected to voltage-luminance measurement, there could be obtained a luminance of 8000 cd/m$^2$ at 8 V as is particularly shown in FIG. 17.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while keeping a current at a given level. As a consequence, it took 3,500 hours before the luminance was reduced to half.

EXAMPLE 20

This example illustrates fabrication of an organic electroluminescent device having a double hetero structure using, as a luminescent material, a compound of the structural formula (16)-1, which is a compound of the general formula (I) wherein $R^1$ and $R^4$ independently represent a 3-ethyoxyphenyl group, and $R^6$ and $R^8$ independently represent a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, near the substrate, followed by subjecting α-NPD of the afore-indicated structural formula to vacuum deposition at a vacuum of $10^{-4}$ Pa or below to form, for example, a 30 nm thick hole transport layer. The deposition rate was at 0.2 nm/second.

Further, the compound of the afore-indicated structural formula (16)-1 used as a luminescent material was vacuum deposited in contact with the hole transport layer. The thickness of the luminescent layer composed of the compound of the structural formula (16)-1 was set, for example, at 30 nm, and the deposition rate was at 0.2 nm/second.

Alq$_3$ of the afore-indicated structural formula used as an electron transport material was vacuum deposited in contact with the luminescent layer. The thickness of the Alq$_3$ layer was set, for example, at 30 nm, and the deposition rate was at 0.2 nm/second.

A built-up film of Mg and Ag provided as a cathode material was used. More particularly, Mg and Ag were, respectively, vacuum deposited at a deposition rate of 1 nm/second to form, for example, a 50 nm thick Mg film and a 150 nm thick Ag film. In this way, an organic electroluminescent device of Example 20 as shown in FIG. 35 was fabricated.

Luminescent characteristics were evaluated by applying a forward bias DC voltage to the thus fabricated organic electroluminescent device of Example 20 in an atmosphere of nitrogen. The luminescent color was red, and the device was subjected to spectral measurement, with the result that spectra having a luminescent peak at 620 nm were obtained. Moreover, when the device was subjected to voltage-luminance measurement, there could be obtained a luminance of 11,000 cd/m$^2$ at 8 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while passing a current at a given level. As a consequence, it took 5,000 hours before the luminance was reduced to half.

EXAMPLE 21

Example 19 was repeated with respect to the layer arrangement and the film formation procedures except that TPD (triphenyldiamine derivative) of the following structural formula was used as a hole transport material in place of α-NPD, thereby fabricating an organic electroluminescent device.

TPD:

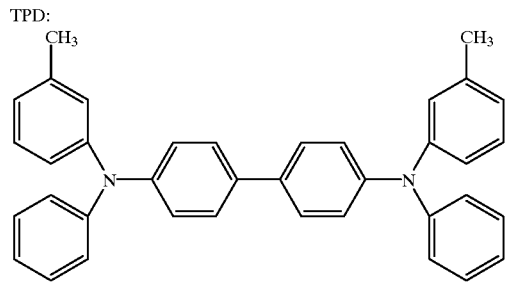

The organic electroluminescent device of this example assumed red luminescence, like Example 19. The results of spectral measurement reveal that spectra were in coincidence with those of the organic electroluminescent device of Example 19.

EXAMPLE 22

The general procedure of Example 18 was repeated using, as a hole transport luminescent material, the compound of the following structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{21}$ independently represent a cyano group, thereby fabricating an organic electroluminescent device having a single hetero structure.

Structural formula (16)-2:

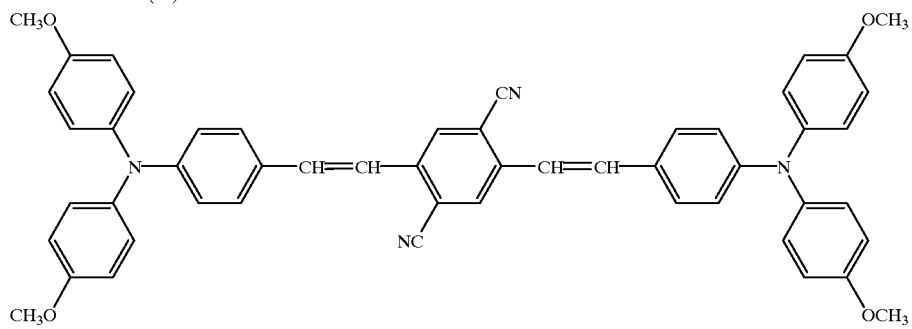

Figure 18:
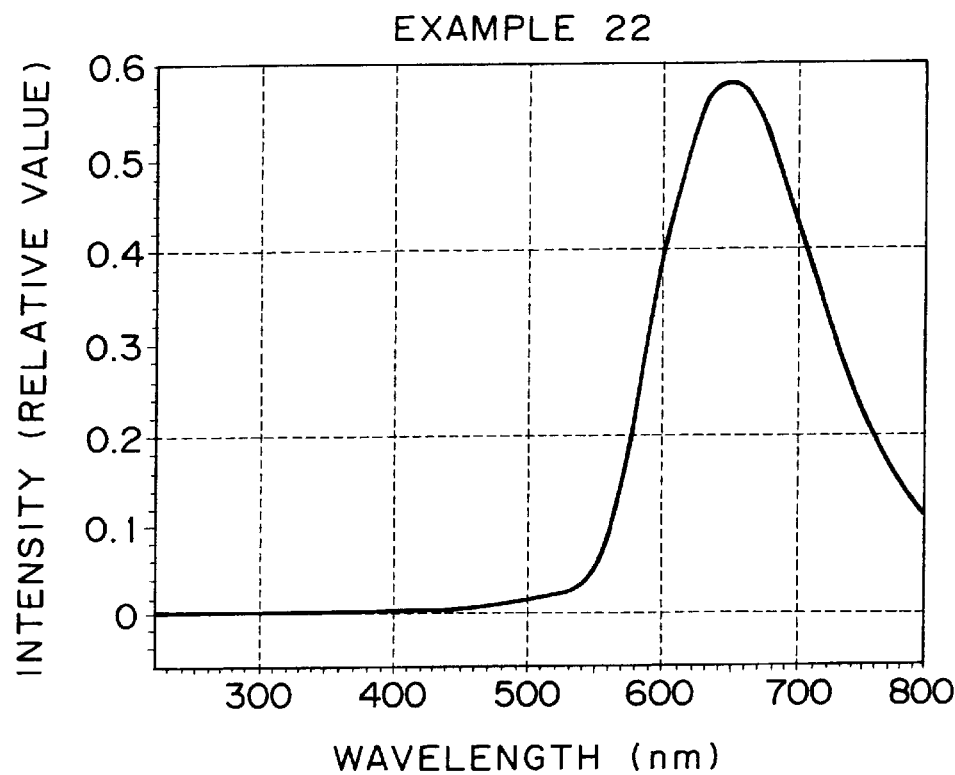
FIG. 18 is an emission spectrogram of an organic electroluminescent device of Example 22 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 650 nm were obtained as shown in FIG. 18. Moreover, when the device was subjected to voltage-luminance measurement, there could be obtained a luminance of 1,200 cd/m² at 9.5 V as is particularly sown in FIG. 20.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 200 cd/m² while passing a current at a given level. As a consequence, it took 1,000 hours before the luminance was reduced to half.

EXAMPLE 23

The general procedure of Example 19 was repeated using, as a hole transport luminescent material, the compound of the afore-indicated structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{21}$ independently represent a cyano group, thereby fabricating an organic electroluminescent device having a single hetero structure.

Figure 19:
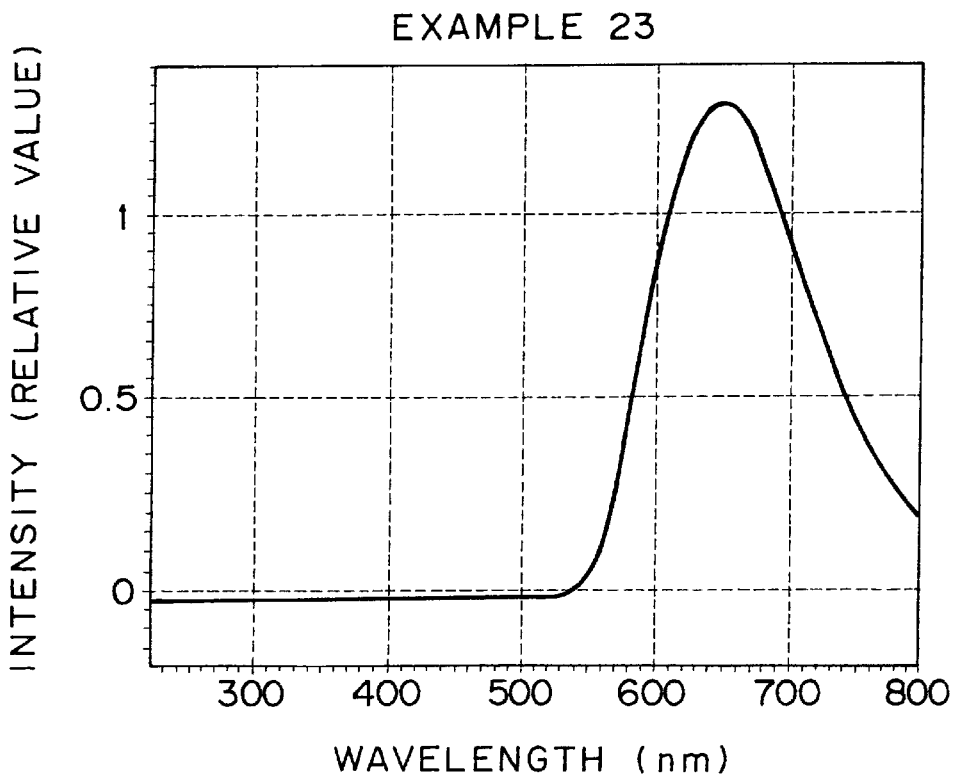
FIG. 19 is an emission spectrogram of an organic electroluminescent device of Example 23 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement in the same manner as in Example 19, with the result that spectra having a luminescent peak at 650 nm were obtained as shown in FIG. 19. Moreover, when the device was subjected to voltage-luminance measurement, there could be obtained a luminance of 600 cd/m² at 10.5 V as is particularly sown in FIG. 21.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 200 cd/m² while passing a current at a given level. As a consequence, it took 700 hours before the luminance was reduced to half.

EXAMPLE 24

The general procedure of Example 20 was repeated using, as a luminescent material, the compound of the afore-indicated structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{21}$ independently represent a cyano group, thereby fabricating an organic electroluminescent device having a double hetero structure.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 650 nm were obtained as shown in FIG. 19. Moreover, when the device was subjected to voltage-luminance measurement, there could be obtained a luminance of 1,800 cd/m² at 8.5 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 200 cd/m² while passing a current at a given level. As a consequence, it took 1,500 hours before the luminance was reduced to half.

EXAMPLE 25

Example 23 was repeated with respect to the layer arrangement and the film formation procedures except that TPD (triphenyldiamine derivative) of the afore-indicated structural formula was used as a hole transport material in place of α-NPD, thereby fabricating an organic electroluminescent device.

The organic electroluminescent device of this example assumed red luminescence, like Example 23. The results of spectral measurement reveal that spectra were in coincidence with those of the organic electroluminescent device of Example 19.

EXAMPLE 26

The general procedure of Example 18 was repeated using, as a hole transport luminescent material, the compound of the following structural formula (16)-3, which corresponds to a compound of the general formula (III) wherein $R^{27}$ and $R^{30}$ independently represent a 3-methoxyphenyl group, and $R^{32}$ and $R^{34}$ independently represent a cyano group, thereby fabricating an organic electroluminescent device having a single hetero structure:

Structural formula (16)-3:

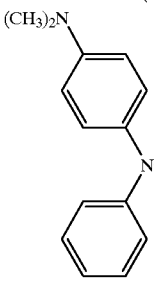
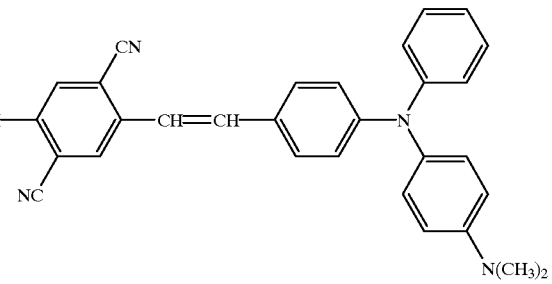

Figure 22:
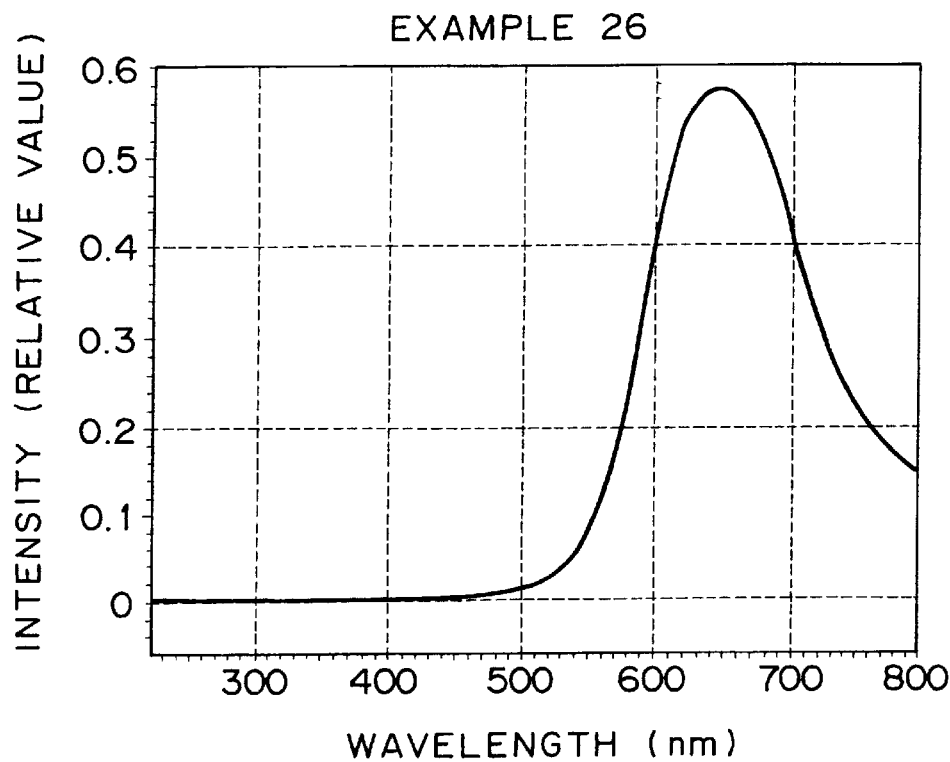
FIG. 22 is an emission spectrogram of an organic electroluminescent device of Example 26 of the invention.
Figure 24:
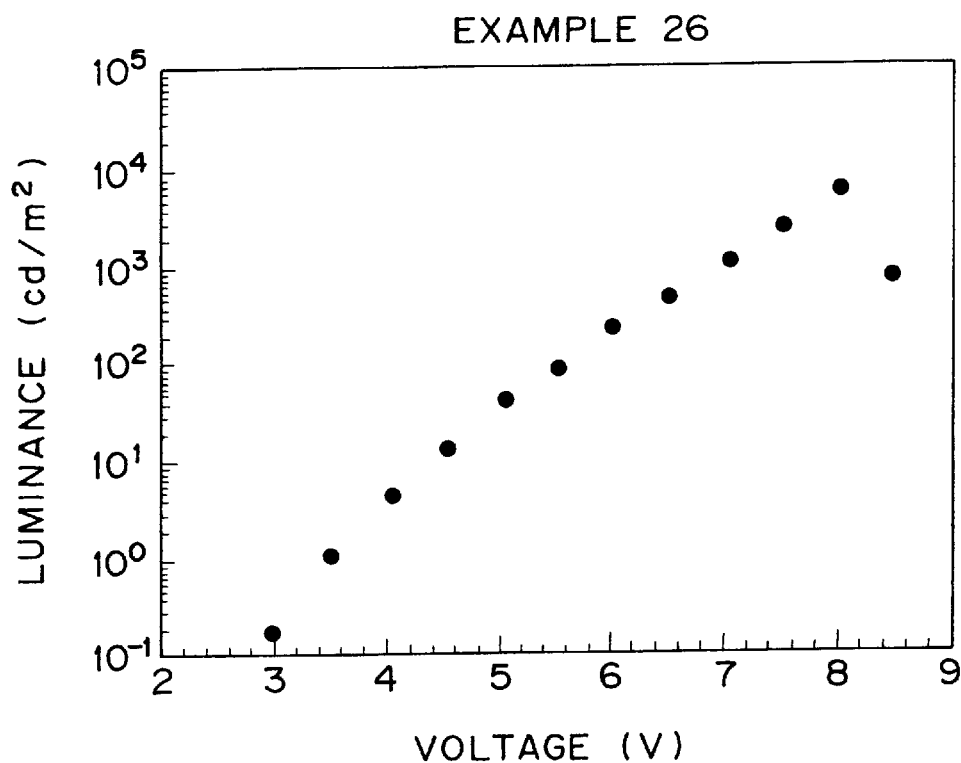
FIG. 24 is a graph showing a voltage-luminance characteristic of the organic electroluminescent device of Example 26 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 640 nm were obtained as shown in FIG. 22. The spectral measurement was performed by use of a spectroscope made by Otuska Electronic Co., Ltd. and using a photodiode array as a detector. Moreover, when the device was subjected to voltage-luminance measurement, there could be obtained a luminance of 6,000 cd/m² at 8 V, as shown in FIG. 24.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 3,800 hours before the luminance was reduced to half.

EXAMPLE 27

The general procedure of Example 19 was repeated using, as an electron transport luminescent material, the compound of the afore-indicated structural formula (16)-3, which corresponds to a compound of the general formula (III) wherein $R^{27}$ and $R^{30}$ independently represent a 3-dimethylaminophenyl group, and $R^{32}$ and $R^{34}$ independently represent a cyano group, thereby fabricating an organic electroluminescent device having a single hetero structure.

Figure 23:
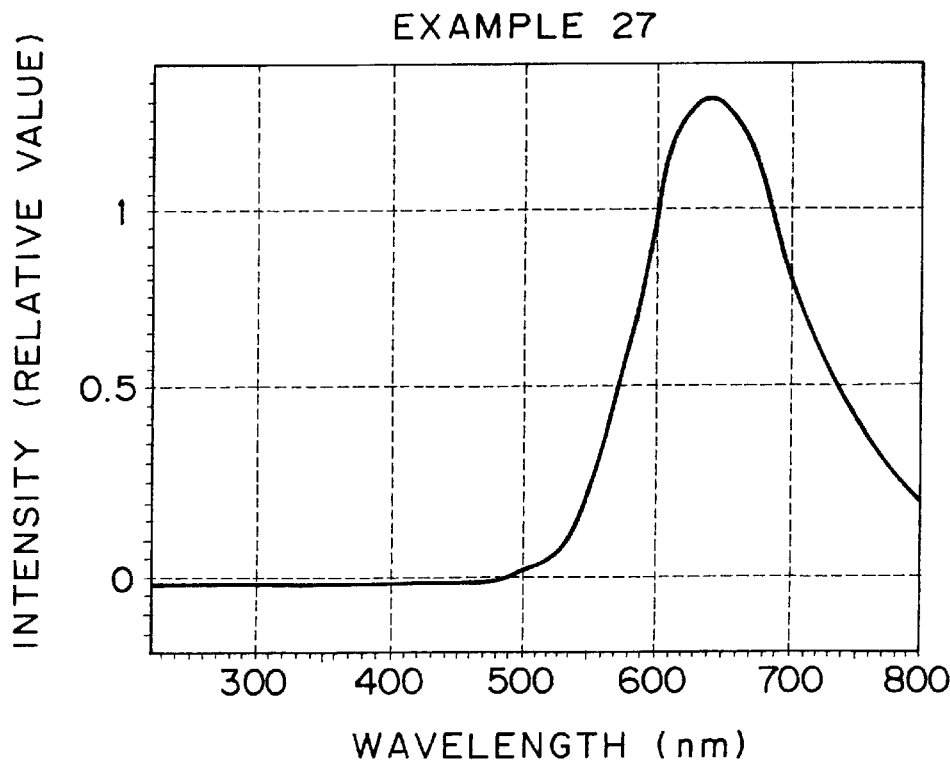
FIG. 23 is an emission spectrogram of an organic electroluminescent device of Example 27 of the invention.
Figure 25:
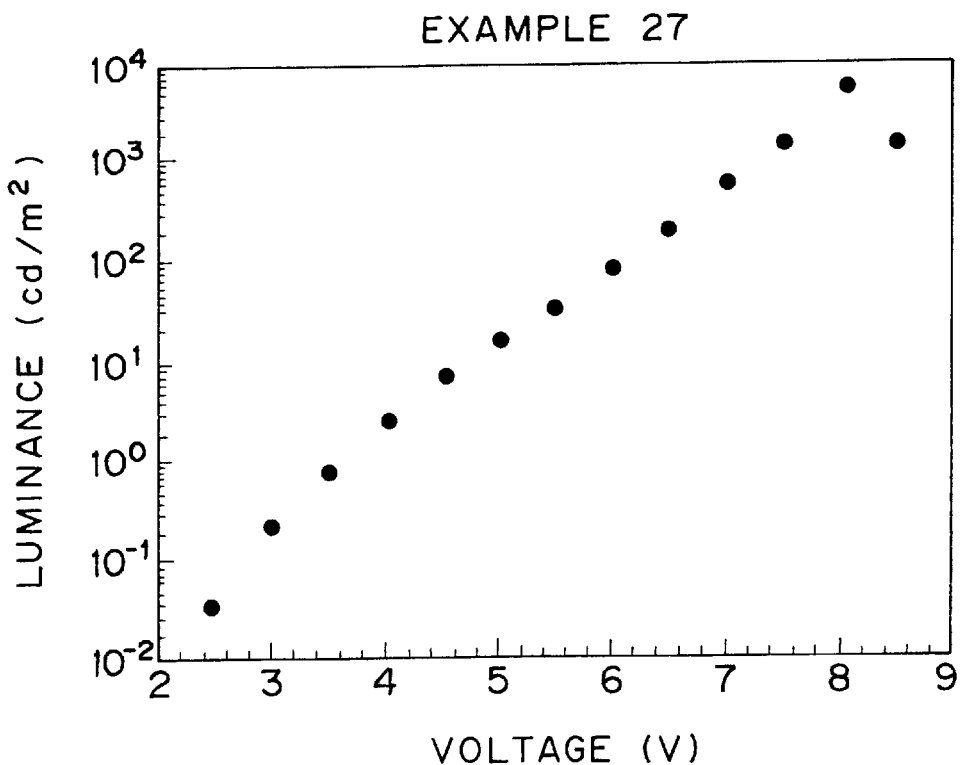
FIG. 25 is a graph showing a voltage-luminance characteristic of the organic electroluminescent device of Example 27 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement in the same manner as in Example 19, with the result that spectra having a luminescent peak at 640 nm were obtained as shown in FIG. 23. Moreover, when the device was subjected to voltage-luminance measurement, there could be obtained a luminance of 5,300 cd/m² at 8 V, as shown in FIG. 25.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 3,200 hours before the luminance was reduced to half.

EXAMPLE 28

The general procedure of Example 20 was repeated using, as a luminescent material, the compound of the afore-indicated structural formula (16)-3, which corresponds to a compound of the general formula (III) wherein $R^{27}$ and $R^{30}$ independently represent a 3-dimethylaminophenyl group, and $R^{32}$ and $R^{34}$ independently represent a cyano group, thereby fabricating an organic electroluminescent device having a double hetero structure.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 640 nm were obtained. Moreover, when the device was subjected to voltage-luminance measurement, there could be obtained a luminance of 6,800 cd/m² at 8 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 4,500 hours before the luminance was reduced to half.

EXAMPLE 29

Example 27 was repeated with respect to the layer arrangement and the film formation procedures, but TPD (triphenyldiamine derivative) of the afore-indicated structural formula was used as a hole transport material in place of α-NPD, thereby fabricating an organic electroluminescent device.

The organic electroluminescent device of this example assumed red luminescence, like Example 27. The results of spectral measurement reveal that spectra were in coincidence with those of the organic electroluminescent device of Example 27.

EXAMPLE 30

The general procedure of Example 18 was repeated using, as a hole transport luminescent material, a compound of the following structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a single hetero structure:

Structural formula (16)-4:

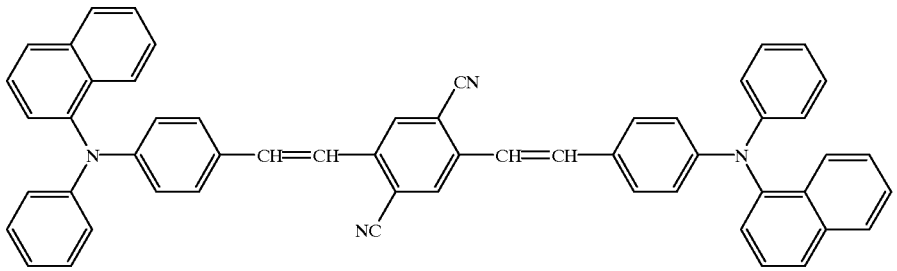

Figure 26:
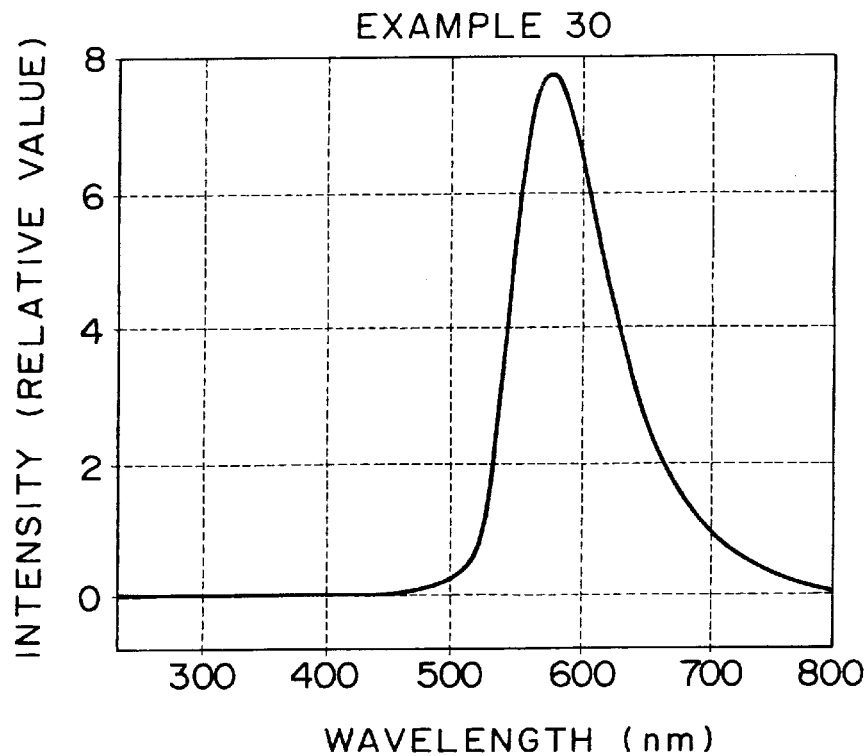
FIG. 26 is an emission spectrogram of an organic electroluminescent device of Example 30 of the invention.
Figure 29:
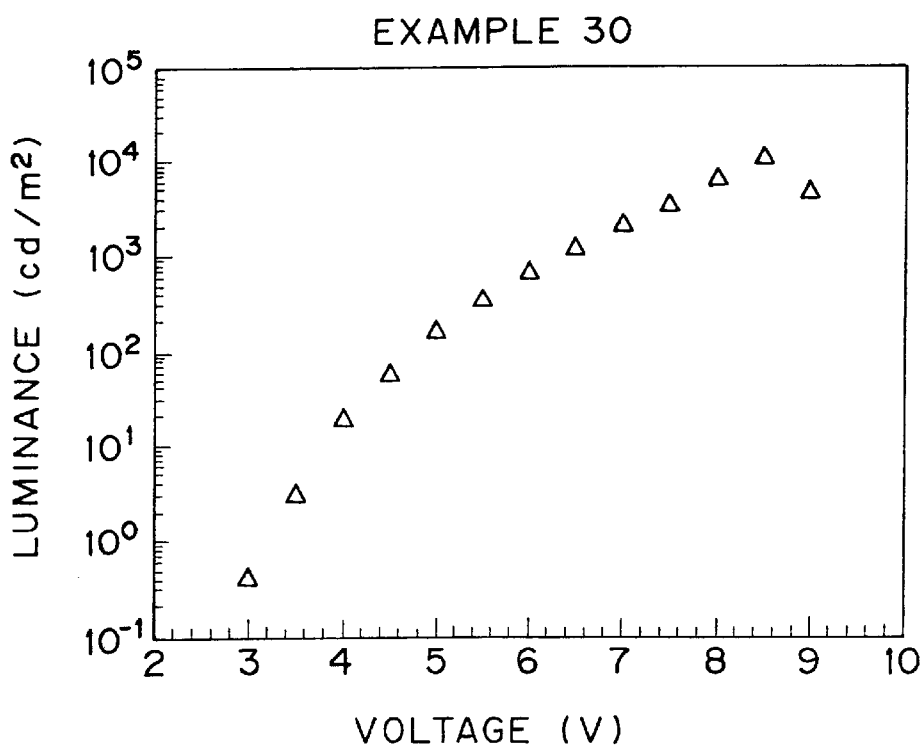
FIG. 29 is a graph showing a voltage-luminance characteristic of the organic electroluminescent device of Example 30 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement, with the result that, as shown in FIG. 26, spectra having a luminescent peak at 578 nm were obtained. The spectral measurement was performed by use of a spectroscope made by Otuska Electronic Co., Ltd. and using a photodiode array as a detector. Moreover, when the device was subjected to voltage-luminance measurement, there could be obtained a luminance of 6,500 cd/m$^2$ at 8 V as is particularly shown in FIG. 29.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 4,000 hours before the luminance was reduced to half.

EXAMPLE 31

The general procedure of Example 30 was repeated using, as an electron transport luminescent material, a compound of the afore-indicated structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a single hetero structure.

Figure 27:
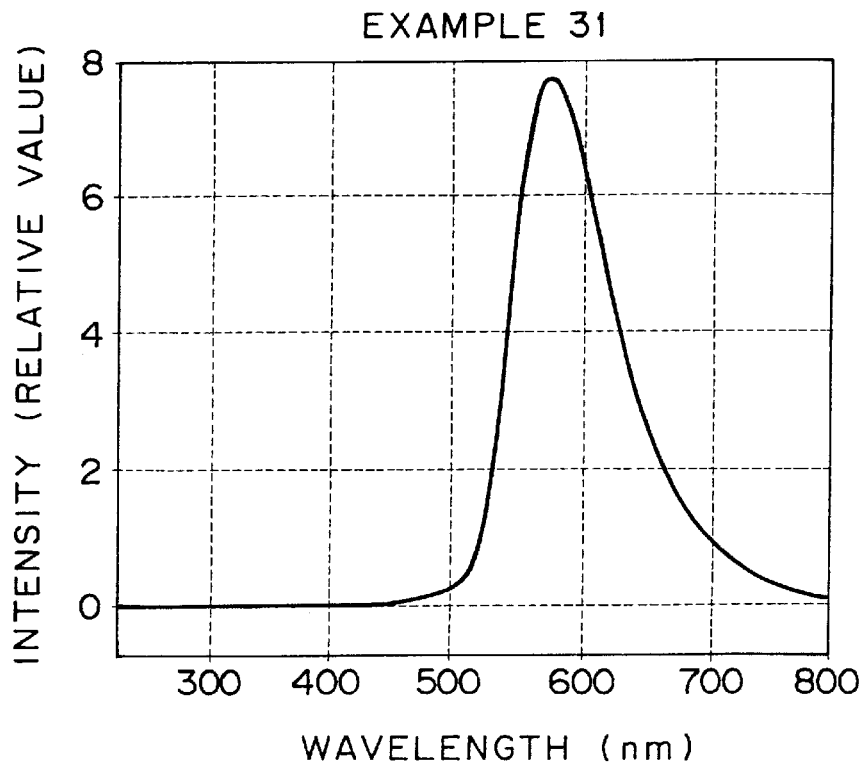
FIG. 27 is an emission spectrogram of an organic electroluminescent device of Example 31 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement, with the result that, as shown in FIG. 27, spectra having a luminescent peak at 578 nm were obtained. Moreover, when the device was subjected to voltage-luminance measurement, there could be obtained a luminance of 5,900 cd/m$^2$ at 8 V as is particularly shown in FIG. 30.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 3,500 hours before the luminance was reduced to half.

EXAMPLE 32

The general procedure of Example 24 was repeated using, as a luminescent material, a compound of the afore-indicated structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a double hetero structure.

Figure 28:
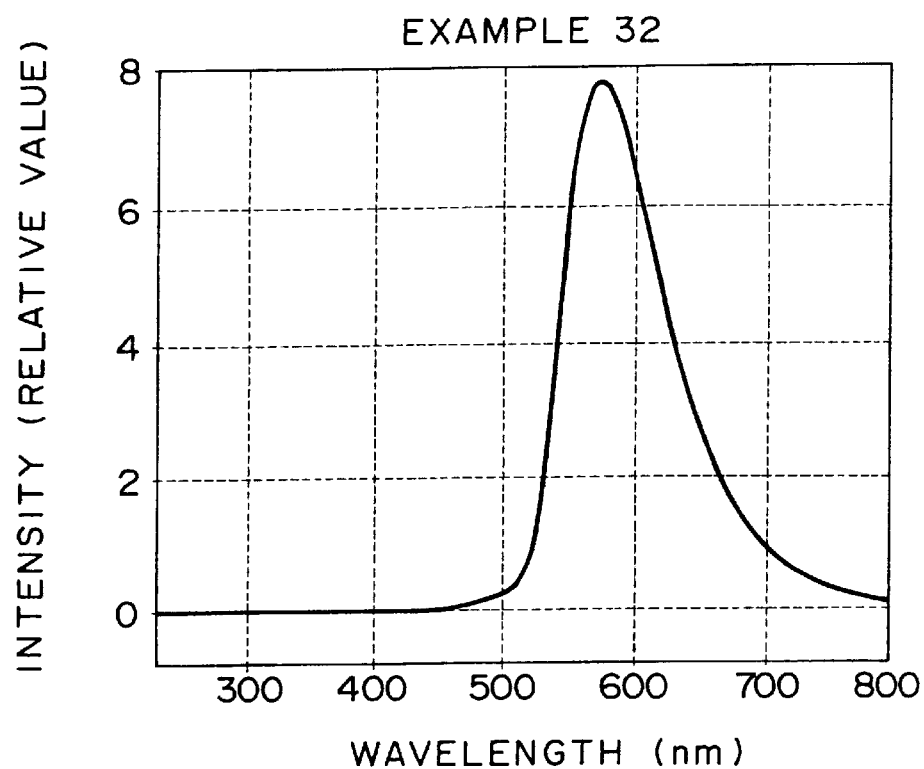
FIG. 28 is an emission spectrogram of an organic electroluminescent device of Example 32 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement, with the result that, as shown in FIG. 28, spectra having a luminescent peak at 578 nm were obtained. Moreover, when the device was subjected to voltage-luminance measurement, there could be obtained a luminance of 7,500 cd/m$^2$ at 8 V as is particularly shown in FIG. 31.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 5,000 hours before the luminance was reduced to half.

EXAMPLE 33

Example 31 was repeated with respect to the layer arrangement and the film formation procedures except that TPD (triphenyldiamine derivative) of the afore-indicated structural formula was used as a hole transport material in place of α-NPD, thereby fabricating an organic electroluminescent device.

The organic electroluminescent device of this example assumed yellow luminescence, like Example 31. The results of spectral measurement reveal that spectra were in coincidence with those of the organic electroluminescent device of Example 31.

As will be seen from the foregoing, the compounds of the invention can be effectively utilized as an organic luminescent material capable of exhibiting intense yellow to red luminescent colors, which depend on the types of introduced and have high glass transition point and melting point. In addition, the compounds are excellent in heat resistance and are electrically, thermally or chemically stable, and can readily form an amorphous vitreous state. Moreover, they are sublimable in nature and are able to form a uniform amorphous film when subjected, for example to vacuum deposition. The compounds of the invention can be prepared in an ordinary and highly efficient manner through synthetic intermediates.

What is claimed is:

1. A bis(aminostyryl)benzene compound of formula [I], [II], [III], or [IV]:

wherein Formula [I] is:

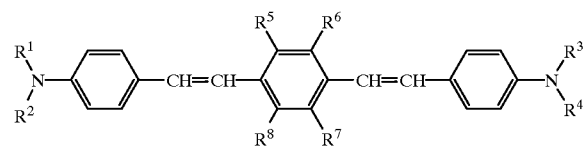

and wherein $R^2$ and $R^3$ independently represent an unsubstituted aryl group, and $R^1$ and $R^4$ independently represent an aryl group represented by the following formula (1):

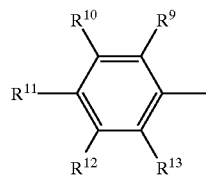

and wherein $R^9$, $R^{10}$, $R^{11}$, $R^{12}$, and $R^{13}$ may be the same or different, with the proviso that at least one of them is selected from the group consisting of ethoxy, propoxy, butoxy, cyclohexyloxy, phenoxy, methyl, ethyl, propyl, butyl, cyclohexyl, and phenyl, and the others are hydrogen atom, and wherein $R^5$, $R^6$, $R^7$, and $R^8$ are independently selected from the group consisting of hydrogen, cyano, nitro or halogen, with the proviso that at least one of them is cyano, nitro or halogen;

wherein Formula [II] is:

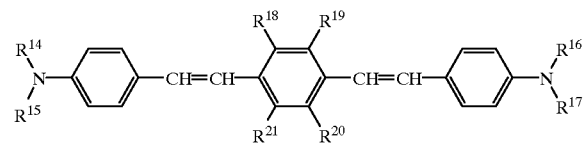

and wherein $R^{14}$, $R^{15}$, $R^{16}$, and $R^{17}$ may be the same or different and independently represent an aryl group of the following formula (2):

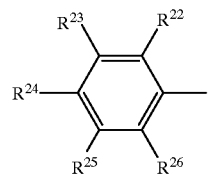

and wherein $R^{22}$, $R^{23}$, $R^{24}$, $R^{25}$, and $R^{26}$ may be the same or different, with the proviso that at least one of them is selected from the group consisting of ethoxy, propoxy, butoxy, cyclohexyloxy, phenoxy, methyl, ethyl, propyl, butyl, cyclohexyl, and phenyl, and the others are hydrogen atoms and wherein $R^{18}$, $R^{19}$, $R^{20}$, and $R^{21}$ and independently selected from the group consisting of hydrogen, cyano, nitro, or halogen, with the proviso that at least one of them is cyano, nitro or halogen;

wherein Formula [III] is:

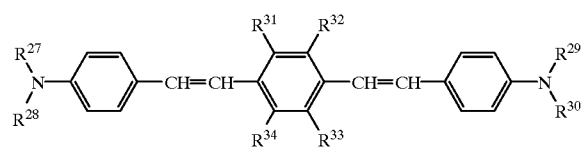

and wherein at least one of $R^{27}$, $R^{28}$, $R^{29}$, and $R^{30}$ represents an aryl group of formula (3) and the others represent an unsubstituted aryl group wherein formula (3) is:

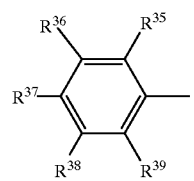

and wherein $R^{35}$, $R^{36}$, $R^{37}$, $R^{38}$, and $R^{39}$ may be the same or different, with the proviso that at least one of them is selected from the group consisting of amino, dimethylamino, diethylamino, dipropylamino, dibutylamino, dicyclohexylamino, and diphenylamino, and the others are hydrogen atoms, and wherein $R^{31}$, $R^{32}$, $R^{33}$, and $R^{34}$ are independently selected from the group consisting of hydrogen, cyano, nitro or halogen, with the proviso that at least one of them is cyano, nitro or halogen;

wherein Formula [IV] is:

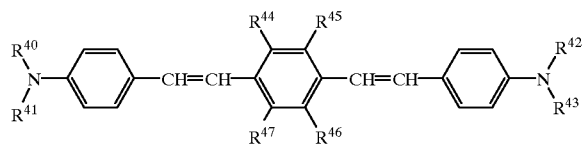

and wherein $R^{41}$ and $R^{42}$ may be the same or different and independently represent an aryl group of formula (4):

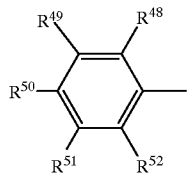

and wherein $R^{48}$, $R^{49}$, $R^{50}$, $R^{51}$, and $R^{52}$ may be the same or different, with the proviso that at least one of them is selected from the group consisting of methoxy, ethoxy, propoxy, butoxy, cyclohexyloxy, phenoxy, methyl, ethyl, propyl, butyl, cyclohexyl, and phenyl, and the others are hydrogen atoms, and $R^{40}$ and $R^{43}$ may be the same or different and independently represent an aryl group of the following formula (5):

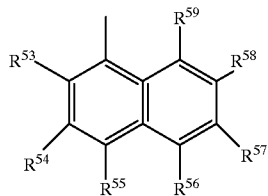

and wherein $R^{53}$, $R^{54}$, $R^{55}$, $R^{56}$, $R^{57}$, $R^{58}$, and $R^{59}$ may be the same or different, with the proviso that at least one of them is selected from the group consisting of methoxy, ethoxy, propoxy, butoxy, cyclohexyloxy, phenoxy, methyl, ethyl, propyl, butyl, cyclohexyl, and phenyl, and the others are hydrogen atoms, and wherein $R^{44}$, $R^{45}$, $R^{46}$, and $R^{47}$ are independently selected from the group consisting of hydrogen, cyano, nitro, or halogen, with the proviso that when $R^5$ and $R^7$ are both Cl or $R^6$ and $R^8$ are both Cl, then $R^{11}$ is not —CH$_2$CH$_2$CO$_2$CH$_3$;

with the further proviso that when $R^5$, $R^6$, $R^7$, and $R^8$ are all hydrogen, and when one of $R^9$ or $R^{13}$ is an alkyl group, an aryl group, or an alkoxy group, all of which may be optionally substituted, then the other of $R^9$ or $R^{13}$ is not hydrogen.

2. A bis(aminostyryl)benzene compound according to claim 1, wherein said compound is of the following formula:

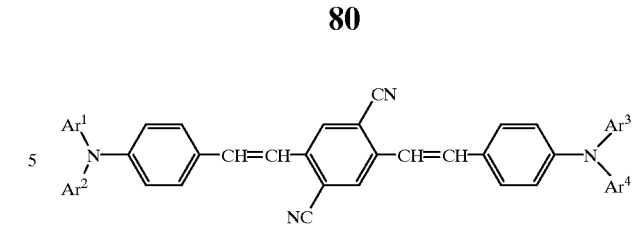

wherein $Ar^1$, $Ar^2$, $Ar^3$, and $Ar^4$ may be the same or different and independently represent an aryl group which may have a substituent, and if a substituent is present, such an aryl group is one selected from those aryl groups of the following formulas (6), (7), (8), and (9):

Formula (6)

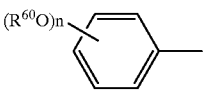

Formula (7)

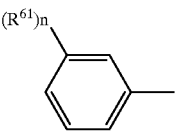

wherein $R^{60}$ is selected from the group consisting of methyl, ethyl, propyl, butyl, cyclohexyl, or phenyl, provided that where $Ar^1$, $Ar^2$, $Ar^3$, and $Ar^4$ are all the same aryl group of the general formula (6), $R^{60}$ is selected from the group consisting of ethyl, propyl, butyl, cyclohexyl, or phenyl, $R^{61}$, $R^{63}$, and $R^{64}$ may be the same or different and independently be selected from the group consisting of methyl, ethyl, propyl, butyl, cyclohexyl, or phenyl, $R^{62}$ is independently selected from hydrogen, methyl, ethyl, propyl, butyl, cyclohexyl, or phenyl, n is an integer of 0 to 5, m is an integer of 0 to 3, and l is an integer of 0 to 4.

3. A bis(aminostyryl)benzene compound according to claim 2, wherein said compound is of the following formula (10), (11), (12), (13), (14), or (15):

Formula (10):

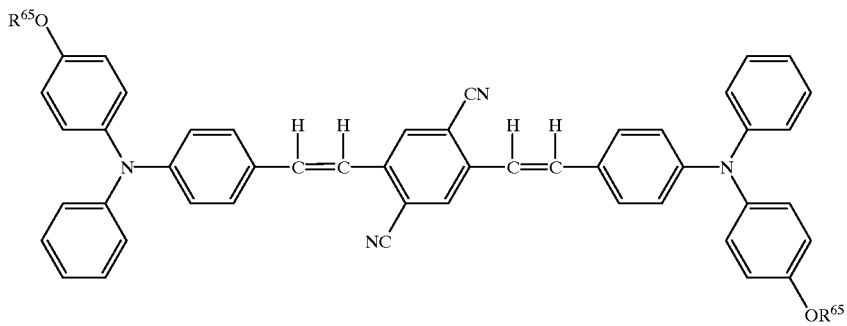

wherein $R^{65}$ is selected from the group consisting of methyl, ethyl, propyl, or butyl:
Formula (11):
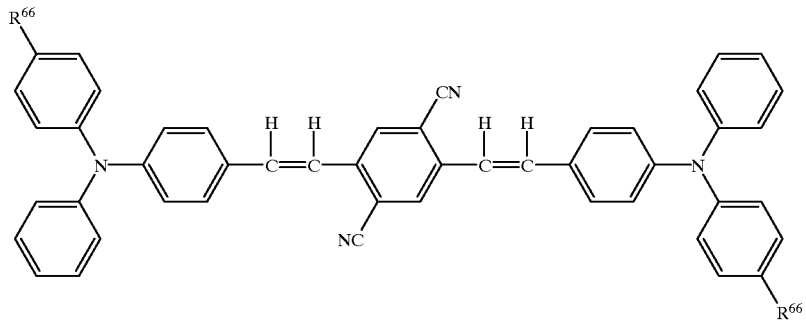
wherein $R^{66}$ is selected from the group consisting of methyl, ethyl, propyl, or butyl:
Formula (12):
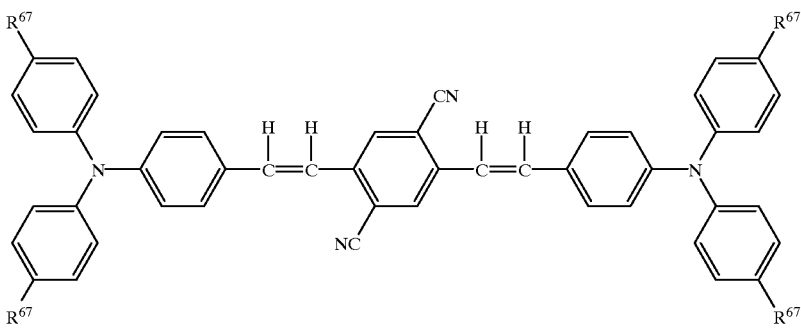
wherein $R^{67}$ is selected from the group consisting of methyl, ethyl, propyl, or butyl:
Formula (13):
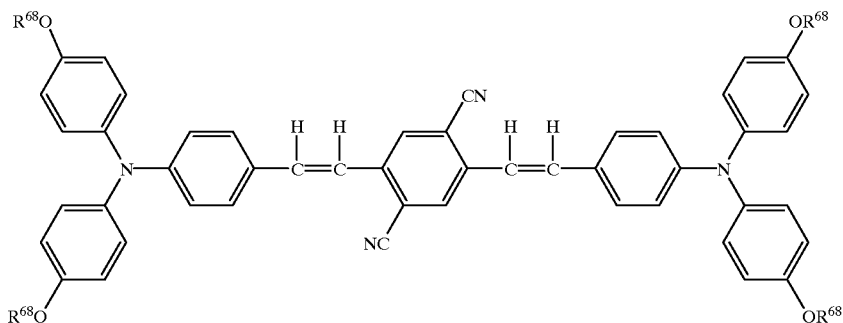
wherein $R^{68}$ is selected from the group consisting of methyl, ethyl, propyl, or butyl:

Formula (14):
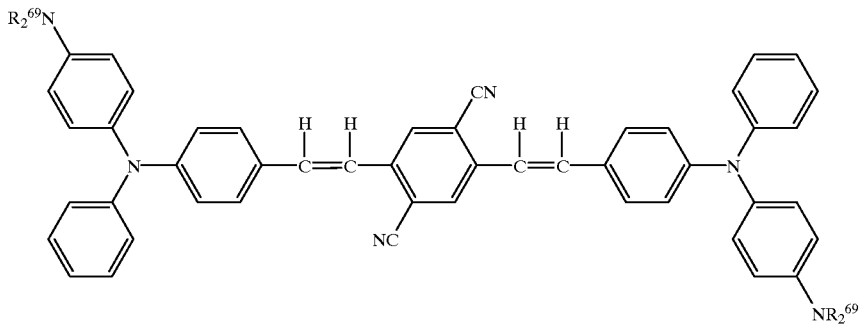
wherein $R^{69}$ is selected from the group consisting of methyl, ethyl, propyl, or butyl:
Formula (15):
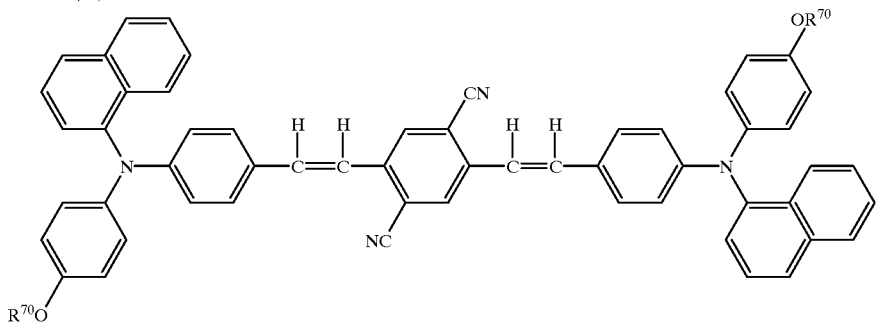
wherein $R^{70}$ is selected from the group consisting of methyl, ethyl, propyl, or butyl.
4. A bis(aminostyryl)benzene compound according to claim 2 wherein said compound is of the following formula: (16)-1, (16)-2, (16)-3, (16)-4, (16)-5, (16)-6 or (16)-7:
formula (16)-1:
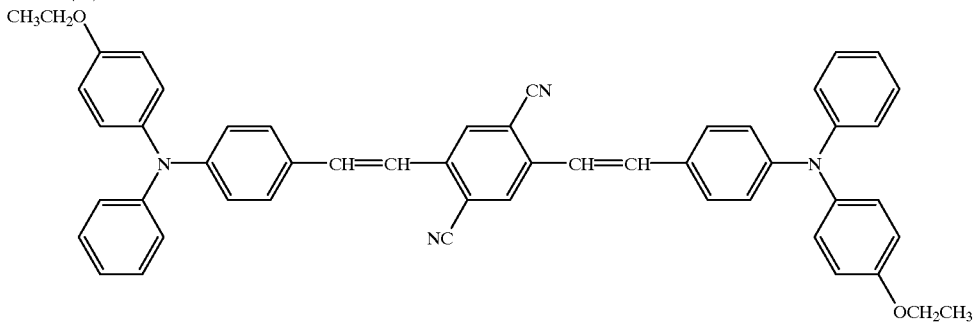

-continued
formula (16)-2:
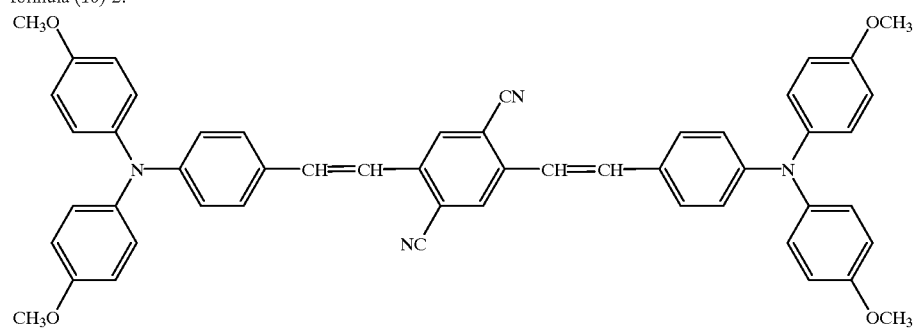
formula (16)-3:
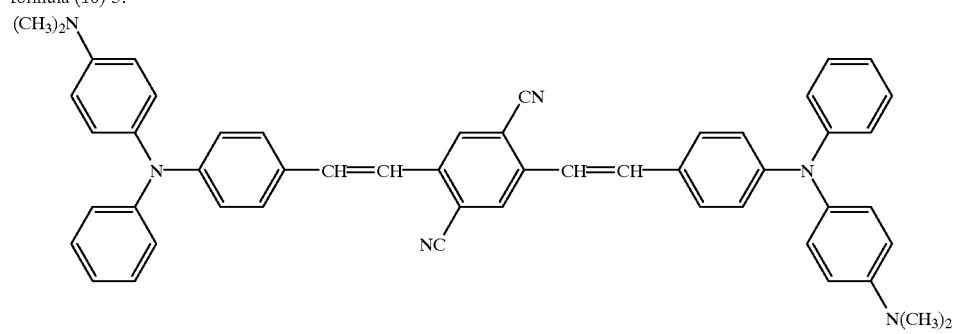
formula (16)-4:
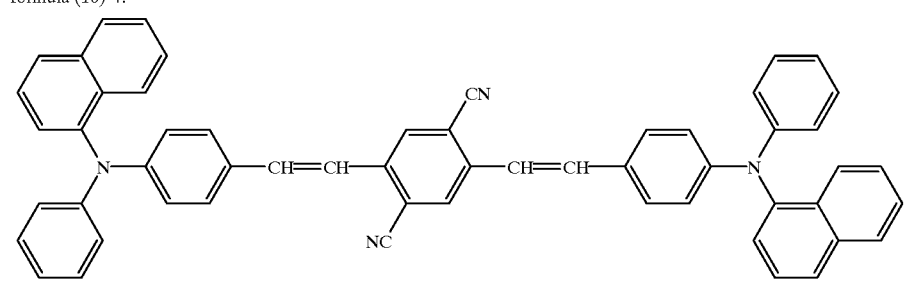
formula (16)-5:
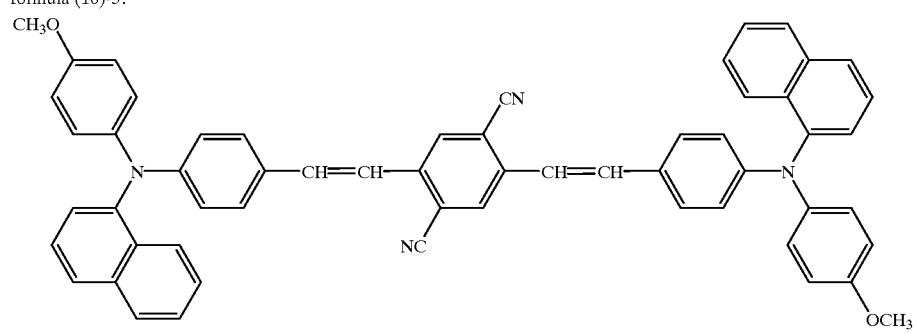
formula (16)-6:
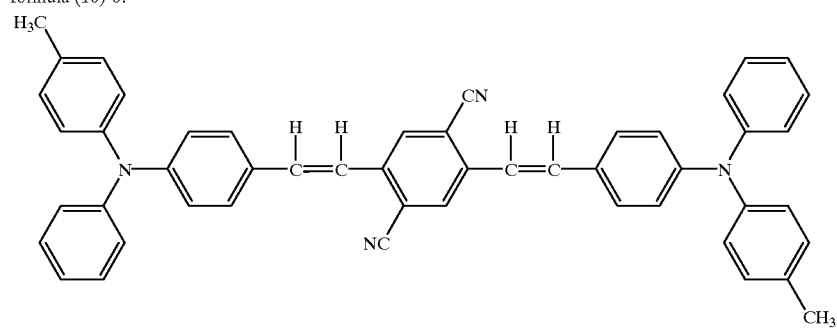

formula (16)-7:
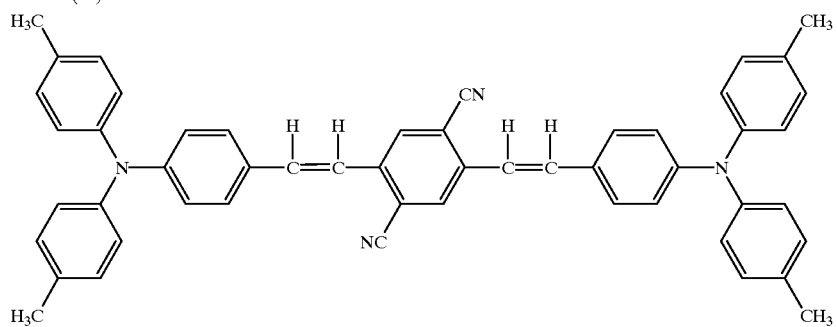
* * * * *

UNITED STATES PATENT AND TRADEMARK OFFICE
CERTIFICATE OF CORRECTION

PATENT NO. : 6,337,167 B1 Page 1 of 1
DATED : January 8, 2002
INVENTOR(S) : Mari Ichimura et al.

It is certified that error appears in the above-identified patent and that said Letters Patent is hereby corrected as shown below:

<u>Title page,</u>
Item [75], Inventor, delete fourth inventor "Ichinori Takada"
Item [30], Foreign Application Priority Data, delete second foreign priority date and number "Nov. 2, 1999 (JP)......11-312069"

Signed and Sealed this

Tenth Day of June, 2003

JAMES E. ROGAN
*Director of the United States Patent and Trademark Office*